US012570653B2

(12) United States Patent
Xu et al.

(10) Patent No.: US 12,570,653 B2
(45) Date of Patent: Mar. 10, 2026

(54) PYRIMIDINE RING COMPOUND

(71) Applicant: MEDSHINE DISCOVERY INC., Suzhou (CN)

(72) Inventors: Zhaobing Xu, Shanghai (CN); Wen Jiang, Shanghai (CN); Lihong Hu, Shanghai (CN); Charles Z. Ding, Shanghai (CN); Guoping Hu, Shanghai (CN); Jian Li, Shanghai (CN); Shuhui Chen, Shanghai (CN); Ping Chen, Shanghai (CN); Xiaobing Yan, Shanghai (CN); Yingchun Liu, Shanghai (CN)

(73) Assignee: Zhejiang Yangli Pharmaceutical Technology Co., Ltd., Zhejiang (CN)

( * ) Notice: Subject to any disclaimer, the term of this patent is extended or adjusted under 35 U.S.C. 154(b) by 489 days.

(21) Appl. No.: 18/041,540

(22) PCT Filed: Aug. 17, 2021

(86) PCT No.: PCT/CN2021/113112
§ 371 (c)(1),
(2) Date: Feb. 13, 2023

(87) PCT Pub. No.: WO2022/037592
PCT Pub. Date: Feb. 24, 2022

(65) Prior Publication Data
US 2023/0303564 A1 Sep. 28, 2023

(30) Foreign Application Priority Data

Aug. 17, 2020 (CN) ......................... 202010826692.0
Jul. 30, 2021 (CN) ......................... 202110873055.3

(51) Int. Cl.
*C07D 471/04* (2006.01)
*C07D 487/04* (2006.01)

(52) U.S. Cl.
CPC ......... *C07D 471/04* (2013.01); *C07D 487/04* (2013.01)

(58) Field of Classification Search
None
See application file for complete search history.

(56) References Cited

U.S. PATENT DOCUMENTS 9,409,907 B2 * 8/2016 Hoelder ............... C07D 405/04
9,834,552 B2 * 12/2017 Hoelder ............... C07D 401/14
9,890,157 B2 * 2/2018 Hoelder ............... C07D 471/04
10,124,004 B2 11/2018 Mizuno et al.
10,172,868 B2 1/2019 Qian et al.
11,084,814 B2 8/2021 Mizuno et al.
11,207,321 B2 * 12/2021 Martin ................. A61K 31/138
11,897,877 B2 * 2/2024 Hoelder ............... C07D 471/04
2012/0046270 A1 2/2012 Ettmayer
2018/0161329 A1 * 6/2018 Mizuno .............. A61K 31/5377
2020/0138815 A1 5/2020 Martin et al.

FOREIGN PATENT DOCUMENTS

CN 105682661 A 6/2016
CN 107614499 A 1/2018
CN 110036012 A 7/2019
WO 2010094695 A1 8/2010
WO WO-2014037750 A1 * 3/2014 .............. A61P 35/00
WO WO-2016194831 A1 * 12/2016 ........... A61K 31/541
WO WO-2018234780 A1 * 12/2018 ........... A61K 31/437
WO 2019223766 A1 11/2019

OTHER PUBLICATIONS

Nov. 18, 2021 International Search Report issued in International Patent Application No. PCT/CN2021/113112.
Nov. 18, 2021 Written Opinion of the International Searching Authority issued in International Patent Application No. PCT/CN2021/113112.
Mar. 19, 2025 Chinese First Office Action issued in Chinese Patent Application No. 2021800506473.
Mar. 19, 2025 First Search Report issued in Chinese Patent Application No. 2021800506473.

* cited by examiner

*Primary Examiner* — Andrew D Kosar
(74) *Attorney, Agent, or Firm* — Houston Beshining Law Office PLLC; Liangang Ye

(57) ABSTRACT

A pyrimidine ring compound represented by formula (III), or a pharmaceutically acceptable salt thereof, and an application thereof in preparation of a medication for treating related diseases.

(III)

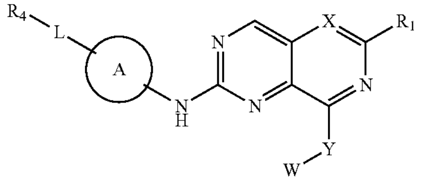

20 Claims, No Drawings

PYRIMIDINE RING COMPOUND

The present application is a National Stage of International Application No. PCT/CN2021/113112, filed on Aug. 17, 2021, which claims priorities of the Chinese Patents Application No. CN202010826692.0 filed on Aug. 17, 2020 and Application No. CN202110873055.3 filed on Jul. 30, 2021, the contents of which are incorporated herein by reference in their entireties.

TECHNICAL FIELD

The present disclosure relates to pyrimidine ring compounds, specifically discloses compounds represented by formula (III) or pharmaceutically acceptable salts thereof, pharmaceutical compositions containing them and use thereof in the preparation of a medicament for treating cancer.

BACKGROUND

Cyclin-dependent kinase (CDKs) are a class of cellular enzymes that play an important role in regulating the division and proliferation of eukaryotic cells, which participate in physiological processes such as cell proliferation and transcription. Clinical studies show that the occurrence of various cancers is closely related to cell cycle regulation. For example, the activation of proto-oncogenes or the inactivation of anti-oncogenes often lead to abnormal cell cycle regulation, resulting in infinite proliferation of cells and tumor formation. Therefore, inducing cell cycle arrest can effectively inhibit tumor growth. According to the different functions of CDKs, they can be divided into two categories: 1) one category of CDK is involved in cell cycle regulation, mainly including CDK1, CDK2, CDK4, CDK6, etc.; 2) the other category of CDK is involved in transcriptional regulation, mainly including CDK7, CDK8, CDK9, CDK10, CDK11, etc. Among them, CDK4/6 is a key regulator of the cell cycle, and the CDK4/6-cyclin D complex formed by combining with cyclin D can phosphorylate a series of substrates including retinoblastoma protein (Rb), which releases and activates the pre-bound transcription factor E2F, making the cells be transformed from G1 phase to S phase, causing cells growth and proliferation, and finally leading to the formation of tumors. CDK4/6 are abnormally activated in a variety of tumors, and inhibiting the activity of CDK4/6 can theoretically inhibit tumor growth.

CDK4/6 inhibitor is arising anti-cancer "magic drug" in the past three to five years, it is rapidly changing the treatment pattern of hormone receptor (HR) positive, human epidermal growth factor receptor 2 (HER2) negative (HR+ HER2−) advanced breast cancer. They effectively overcome or delay the emergence of endocrine resistance, and strive for more survival time for advanced patients. However, like other kinases, the effect of these inhibitors may be limited by the development of primary and secondary drug resistance over time. An important reason for the drug resistance produced by CDK4/6 inhibitors is the amplification or overexpression of cyclin E (J. Clin. Oncol. 2019, 37, 1148-1150). In ER+ breast cancer cells, the high expression of Cyclin E2 is often accompanied by hormone therapy drug resistance (Mol. Cancer Ther., 2012, 11, 1488-1499), and the poor prognosis of breast cancer is closely related to the amplification or overexpression of Cyclin E (N. Engl. J. Med, 2002, 347, 1566-1575). In HER2+ breast cancer, the amplification of Cyclin E has also been reported to have a certain contribution to the drug resistance of Trastuzumab (Proc. Natl. Acad. Sci., 2011, 108, 3671-3676). It is also reported that the overexpression of Cyclin E also plays an important role in the progression of triple-negative breast cancer (Breast Care, 2011, 6, 273-278) or inflammatory breast cancer (Oncotarget, 2017, 8, 14897-14911). Therefore, the development of CDK2 inhibitors may benefit patients with primary and secondary drug resistance to CDK4/6 inhibitors.

Currently, a few number of small molecule inhibitors of CDK2 are in the clinical trial stage. For example, Dinaciclib can inhibit CDK1, CDK2, CDK5 and CDK9, and is in clinical development for breast cancer and blood cancer. In addition, Seliciclib can inhibit CDK2, CDK7 and CDK9, and is conducting clinical research on advanced solid tumors in combination with chemotherapy drugs. However, up to now, no CDK2 inhibitor has been approved, so it is urgent to develop novel, safe and effective CDK2 inhibitors that can treat a variety of cancers, especially small molecule inhibitors that selectively target CDK2, which may have better safety.

CONTENT OF THE PRESENT INVENTION

The present disclosure provides a compound represented by formula (III) or a pharmaceutically acceptable salt thereof, (III)

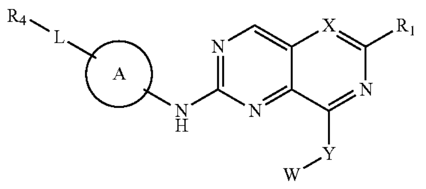

wherein, ring A is selected from $C_{3-8}$ cycloalkyl, 3-10 membered heterocycloalkyl, $C_{3-8}$ cycloalkenyl and 3-10 membered heterocycloalkenyl, and the $C_{3-8}$ cycloalkyl, 3-10 membered heterocycloalkyl, $C_{3-8}$ cycloalkenyl and 3-10 membered heterocycloalkenyl are independently and optionally substituted by 1, 2, or 3 $R_a$;

W is selected from

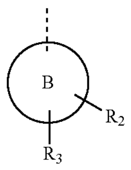

and $R_5$;

ring B is selected from $C_{3-8}$ cycloalkyl, 5-6 membered heteroaryl and 3-10 membered heterocycloalkyl, and the $C_{3-4}$ cycloalkyl, 5-6 membered heteroaryl and 3-10 membered heterocycloalkyl are independently and optionally substituted by 1, 2, or 3 $R_b$;

X is selected from $C(R_c)$ and N;

Y is selected from single bond, —NH— and —O—;

L is selected from single bond and $—S(=O)_2—$;

$R_1$ is selected from H, halogen, $C_{1-3}$ alkyl, $C_{1-3}$ alkoxy and $—C(=O)—C_{1-3}$ alkyl, and the $C_{1-3}$ alkyl, $C_{1-3}$ alkoxy and —C(=O)—$C_{1-3}$ alkyl are independently and optionally substituted by 1, 2, or 3 $R_d$;

$R_2$ and $R_3$ are independently selected from H, halogen, OH, CN, $NH_2$ and $C_{1-8}$ alkyl, and the $C_{1-8}$ alkyl is optionally substituted by 1, 2, or 3 $R_e$;

$R_4$ is selected from $NH_2$, —NH—$C_{1-6}$ alkyl, —NH(CN), —NH(OH), $C_{1-6}$ alkyl, —N(CN)—$C_{1-6}$ alkyl and —N(OH)—$C_{1-6}$ alkyl, and the —NH—$C_{1-6}$ alkyl, $C_{1-6}$ alkyl, —N(CN)—$C_{1-6}$ alkyl and —N(OH)—$C_{1-6}$ alkyl are independently and optionally substituted by 1, 2, or 3 $R_f$;

$R_5$ is selected from $C_{1-3}$ alkyl optionally substituted by 1, 2, or 3 $R_g$;

$R_c$ is selected from H, F, Cl, Br, I and $CH_3$;

$R_d$ is independently selected from F, Cl, Br, I, $CH_3$, $OCH_3$, OH, $NH_2$, CN, COOH;

$R_a$, $R_b$, $R_e$ and $R_f$ are independently selected from F, Cl, Br, I, OH, CN, $CH_3$, $CH_3CH_2$, $CH_3CH_2CH_2$, $CH(CH_3)_2$, $OCH_3$, $OCF_3$, $CHF_2$, $CH_2F$ and $NH_2$;

$R_g$ is independently selected from F, Cl, Br, I, OH, CN and $CH_3$;

the 3-10 membered heterocycloalkyl, 5-6 membered heteroaryl and 3-10 membered heterocycloalkenyl are respectively containing 1, 2, or 3 heteroatoms or heteroatomic groups independently selected from —NH—, —O—, —S— and N.

The present disclosure also provides a compound represented by formula (I) or a pharmaceutically acceptable salt thereof,

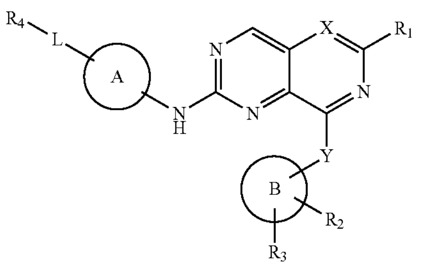

(I)

wherein, ring A is selected from $C_{3-8}$ cycloalkyl, 3-10 membered heterocycloalkyl, $C_{3-8}$ cycloalkenyl and 3-10 membered heterocycloalkenyl, and the $C_{3-8}$ cycloalkyl, 3-10 membered heterocycloalkyl, $C_{3-8}$ cycloalkenyl and 3-10 membered heterocycloalkenyl are independently and optionally substituted by 1, 2, or 3 $R_a$;

ring B is selected from $C_{3-8}$ cycloalkyl and 3-10 membered heterocycloalkyl, and the $C_{3-8}$ cycloalkyl and 3-10 membered heterocycloalkyl are optionally substituted by 1, 2, or 3 $R_b$;

X is selected from $C(R_c)$ and N;

Y is selected from single bond, —NH— and —O—;

L is selected from single bond and —$S(=O)_2$—;

$R_1$ is selected from H, halogen, $C_{1-3}$ alkyl, $C_{1-3}$ alkoxy and —C(=O)—$C_{1-3}$ alkyl, and the $C_{1-3}$ alkyl, $C_{1-3}$ alkoxy and —C(=O)—$C_{1-3}$ alkyl are independently and optionally substituted by 1, 2, or 3 $R_d$;

$R_2$ and $R_3$ are independently selected from H, OH, CN, $NH_2$ and $C_{1-8}$ alkyl, and the $C_{1-8}$ alkyl is optionally substituted by 1, 2, or 3 $R_e$;

$R_4$ is selected from —NH(CN), —NH(OH), $C_{1-6}$ alkyl, —N(CN)—$C_{1-6}$ alkyl and —N(OH)—$C_{1-6}$ alkyl, and the $C_{1-6}$ alkyl, —N(CN)—$C_{1-6}$ alkyl and —N(OH)—$C_{1-6}$ alkyl are independently and optionally substituted by 1, 2, or 3 $R_f$;

$R_c$ is selected from H, F, Cl, Br, I and $CH_3$;

$R_d$ is independently selected from F, Cl, Br, I, $CH_3$, $OCH_3$, OH, $NH_2$, CN, COOH;

$R_a$, $R_b$, $R_e$ and $R_f$ are independently selected from F, Cl, Br, I, OH, CN, $CH_3$, $CH_3CH_2$, $CH_3CH_2CH_2$, $CH(CH_3)_2$, $OCH_3$, $OCF_3$, $CHF_2$, $CH_2F$ and $NH_2$.

The 3-10 membered heterocycloalkyl and 3-10 membered heterocycloalkenyl are respectively containing 1, 2 or 3 heteroatoms or heteroatomic groups independently selected from —NH—, —O—, —S— and N.

In some embodiments of the present disclosure, the $R_1$ is selected from H, Cl, $CHF_2$, $CF_3$ and $CH_3$, and other variables are as defined in the present disclosure.

In some embodiments of the present disclosure, the $R_1$ is selected from H, Cl, $CHF_2$ and $CH_3$, and other variables are as defined in the present disclosure.

In some embodiments of the present disclosure, the $R_2$ and $R_3$ are independently selected from H, OH, CN, $NH_2$ and $C_{1-6}$ alkyl, and the $C_{1-8}$ alkyl is optionally substituted by 1, 2, or 3 $R_e$.

In some embodiments of the present disclosure, the $R_2$ and $R_3$ are independently selected from H, F, Cl, OH and $CH_3$, and other variables are as defined in the present disclosure.

In some embodiments of the present disclosure, the $R_2$ and $R_3$ are independently selected from H, OH and $CH_3$, and other variables are as defined in the present disclosure.

In some embodiments of the present disclosure, the $R_4$ is selected from $CH_3$, $NH_2$ and —$NH(CH_3)$, and other variables are as defined in the present disclosure.

In some embodiments of the present disclosure, the $R_4$ is selected from $CH_3$, and other variables are as defined in the present disclosure.

In some embodiments of the present disclosure, the X is selected from CH, CF, CCl, CBr, $CCH_3$ and N, and other variables are as defined in the present disclosure.

In some embodiments of the present disclosure, the X is selected from CH, CCl, CBr, $CCH_3$ and N, and other variables are as defined in the present disclosure.

In some embodiments of the present disclosure, the ring A is selected from 5-6 membered heterocycloalkyl, and the 5-6 membered heterocycloalkyl is optionally substituted by 1, 2, or 3 $R_a$, and other variables are as defined in the present disclosure.

In some embodiments of the present disclosure, the ring A is selected from piperidinyl, and the piperidinyl is optionally substituted by 1, 2, or 3 $R_a$, and other variables are as defined in the present disclosure.

In some embodiments of the present disclosure, the ring A is selected from

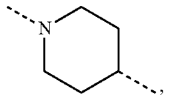,

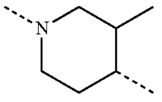

and

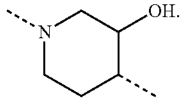.

In some embodiments of the present disclosure, the ring A is selected from

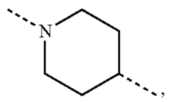

, and other variables are as defined in the present disclosure.

In some embodiments of the present disclosure, the ring B is selected from $C_{5-6}$ cycloalkyl, 5-6 membered heterocycloalkyl and 5-6 membered heteroaryl, and the $C_{5-6}$ cycloalkyl, 5-6 membered heterocycloalkyl and 5-6 membered heteroaryl are independently and optionally substituted by 1, 2, or 3 $R_b$, and other variables are as defined in the present disclosure.

In some embodiments of the present disclosure, the ring B is selected from cyclopentyl, pyrrolidinyl and pyrazolyl, and the cyclopentyl, pyrrolidinyl and pyrazolyl are independently and optionally substituted by 1, 2, or 3 $R_b$, and other variables are as defined in the present disclosure.

In some embodiments of the present disclosure, the ring B is selected from $C_{3-6}$ cycloalkyl, and the $C_{3-6}$ cycloalkyl is optionally substituted by 1, 2, or 3 $R_b$, and other variables are as defined in the present disclosure.

In some embodiments of the present disclosure, the ring B is selected from cyclopentyl, and the cyclopentyl is optionally substituted by 1, 2, or 3 $R_b$, and other variables are as defined in the present disclosure.

In some embodiments of the present disclosure, the structural unit

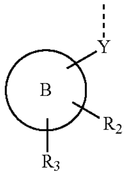

is selected from

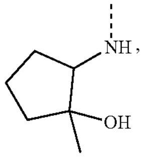 , 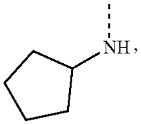 , 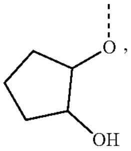 ,

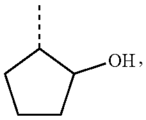 , 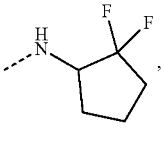 , 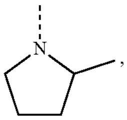 ,

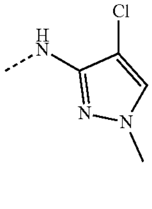 and 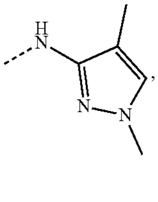 , and other variables are as defined in the present disclosure.

In some embodiments of the present disclosure, the structural unit

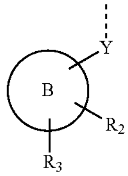

is selected from

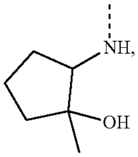 , 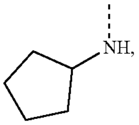 , 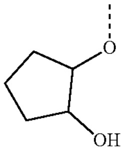 and

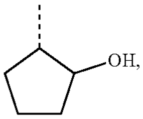 , and other variables are as defined in the present disclosure.

In some embodiments of the present disclosure, the structural unit —Y—W is selected from

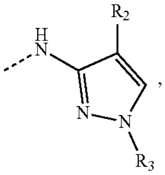 , 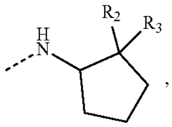 ,

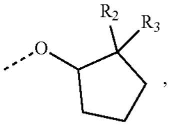 , 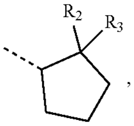 , 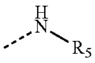 and

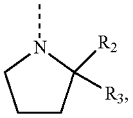 , and other variables are as defined in the present disclosure.

In some embodiments of the present disclosure, the structural unit —Y—W is selected from

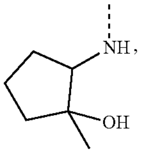 , 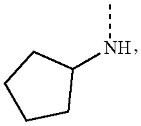 , 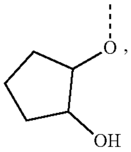 ,

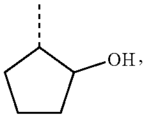 , 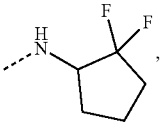 , 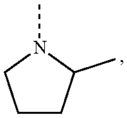 ,

-continued

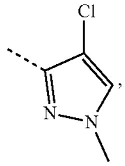,

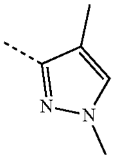

and

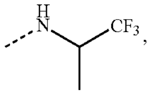, and other variables are as defined in the present disclosure.

In some embodiments of the present disclosure, the structural unit

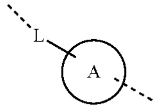

is selected from

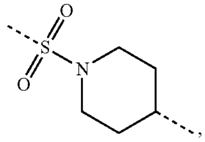, and other variables are as defined in the present disclosure.

In some embodiments of the present disclosure, the $R_5$ is selected from

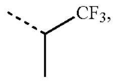, and other variables are as defined in the present disclosure.

In some embodiments of the present disclosure, the compound is selected from (I-2)

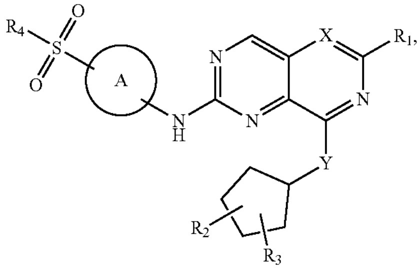,

-continued (III-1)

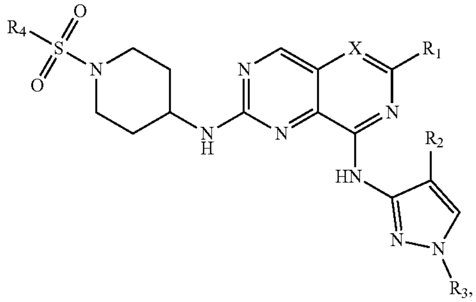, (III-2)

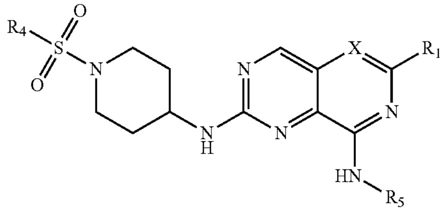

and (III-3)

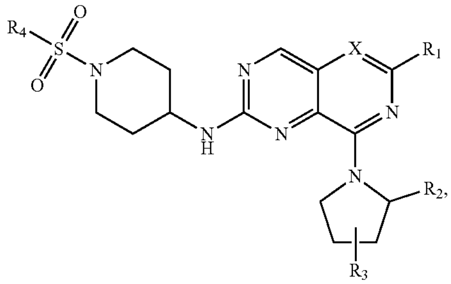

wherein, $R_1$, $R_2$, $R_3$, $R_4$, $R_5$, X, Y and ring Aare as defined in the present disclosure.

In some embodiments of the present disclosure, the compound is selected from (III-4)

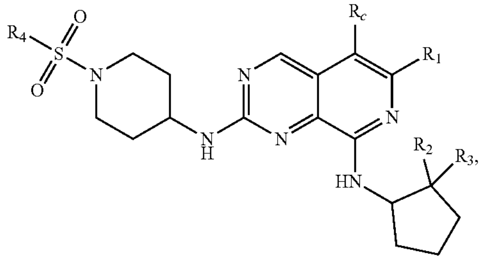, (III-5)

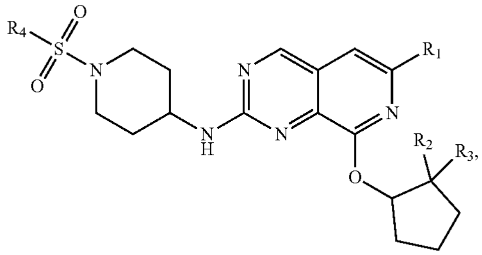,

-continued (III-6)

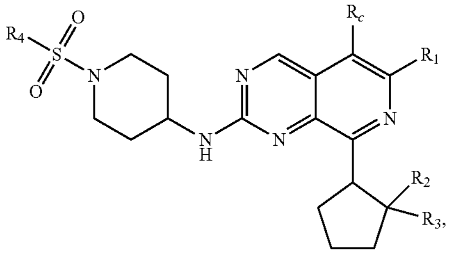

(III-7)

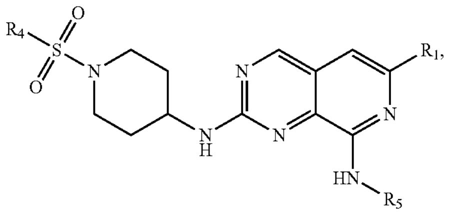

(III-8)

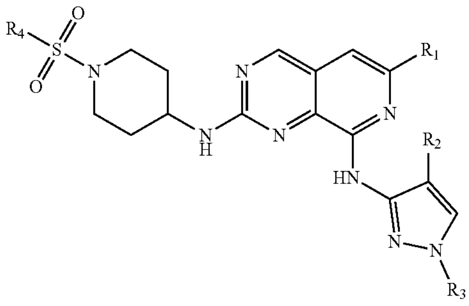

and (III-9)

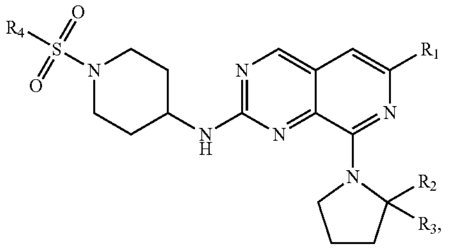

wherein, $R_1$, $R_2$, $R_3$, $R_4$, $R_5$ and $R_c$ are as defined in the present disclosure.

In some embodiments of the present disclosure, the compound is selected from (I-2)

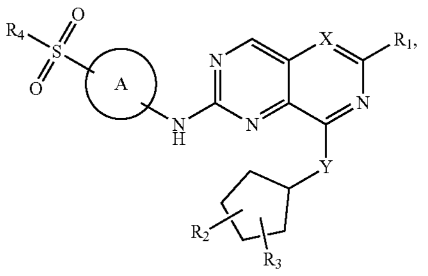

wherein, $R_1$, $R_2$, $R_3$, $R_4$, X, Y and ring A are as defined in the present disclosure.

In some embodiments of the present disclosure, the compound is selected from (I-3)

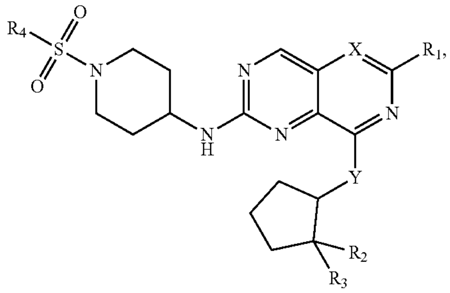

wherein, $R_1$, $R_2$, $R_3$, $R_4$, X and Y are as defined in the present disclosure.

The present disclosure also provides a compound or a pharmaceutically acceptable salt thereof, wherein, the compound selected from:

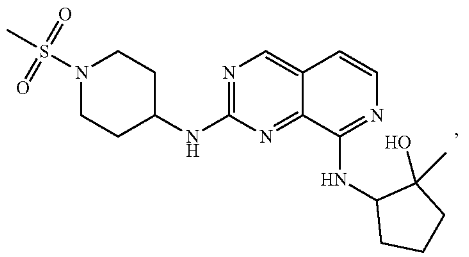

,

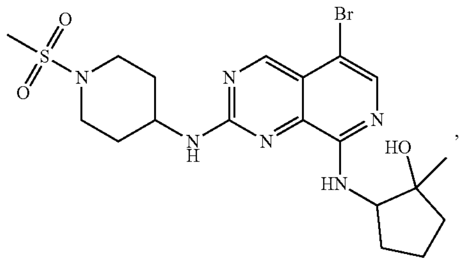

,

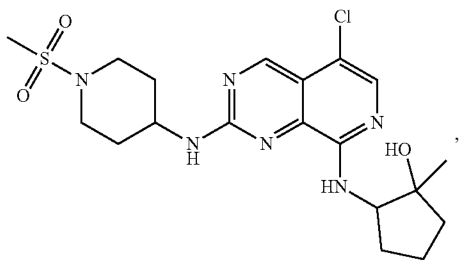

,

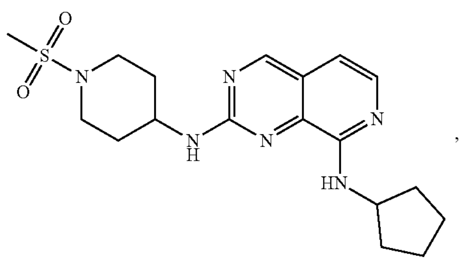

,

-continued
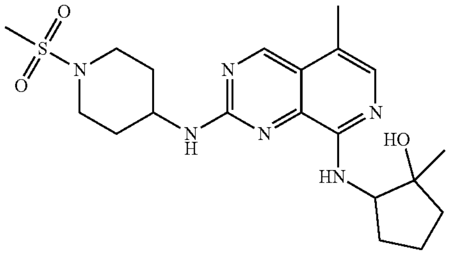
,
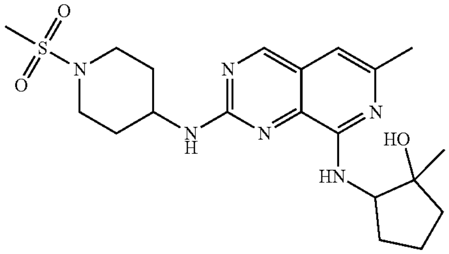
,
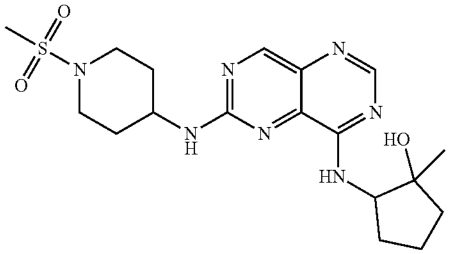
,
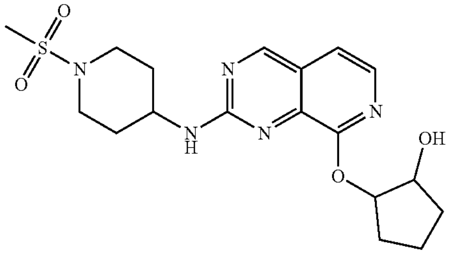
,
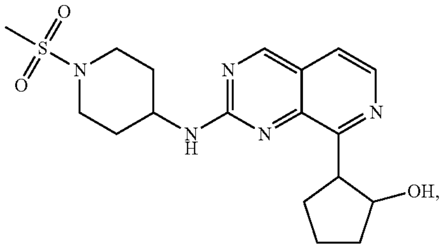
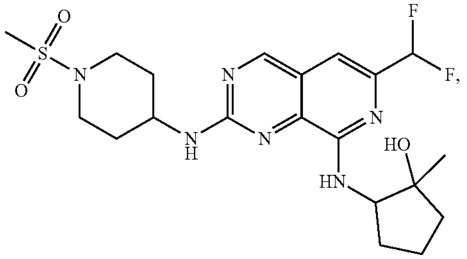
-continued
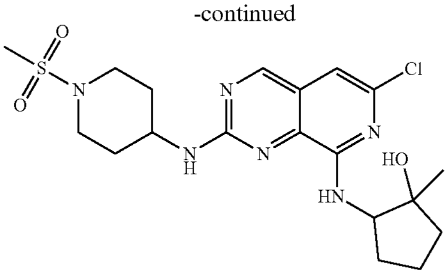
,
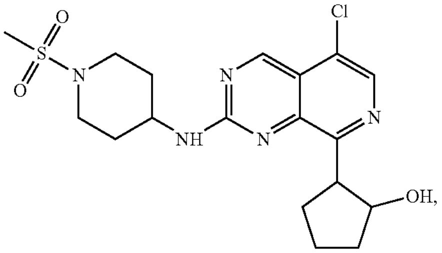
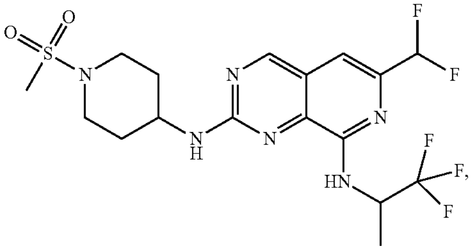
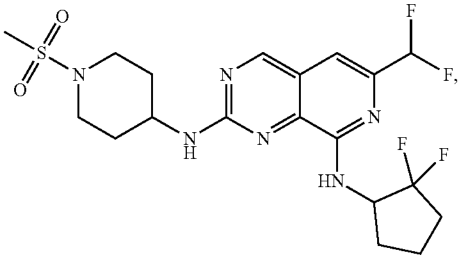
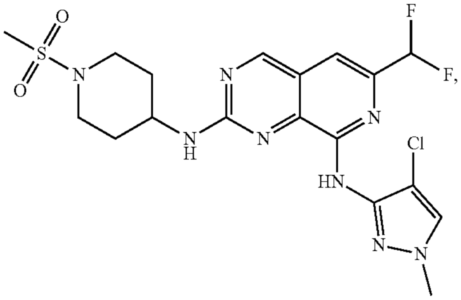
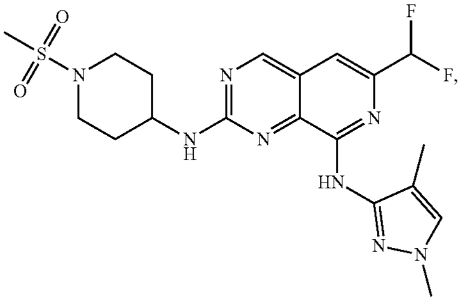

-continued
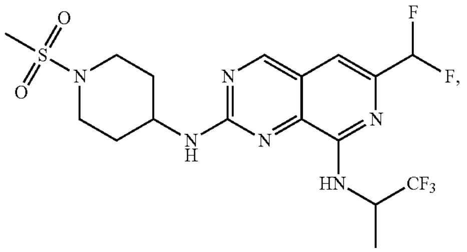
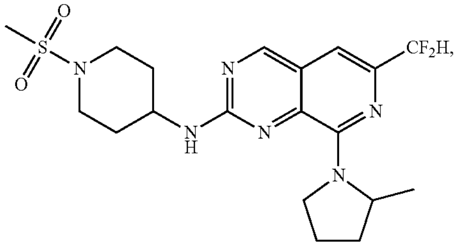
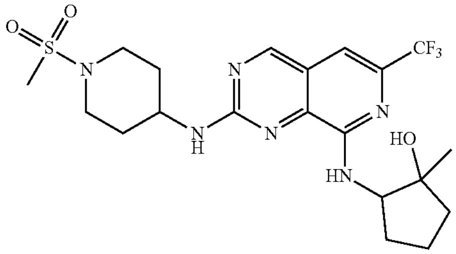
,
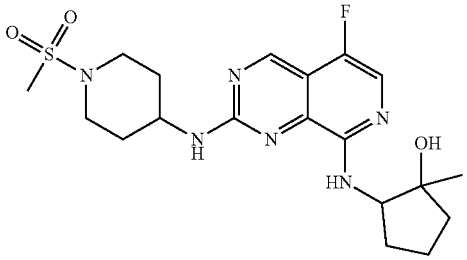
,
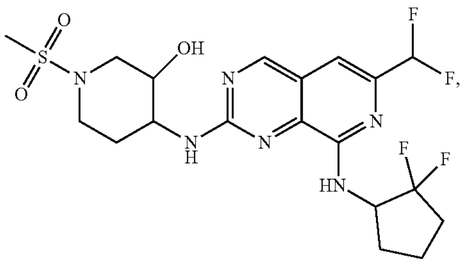
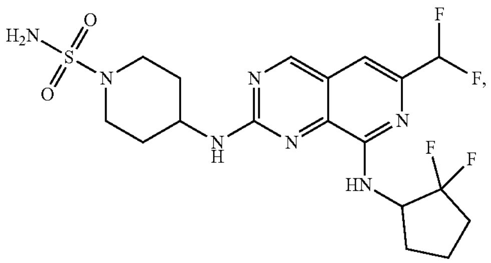
-continued
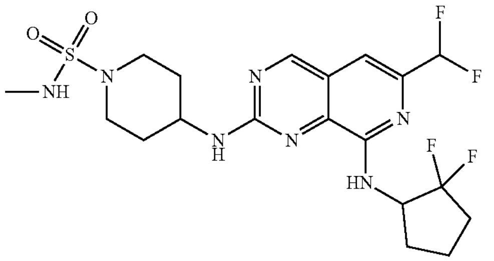
and
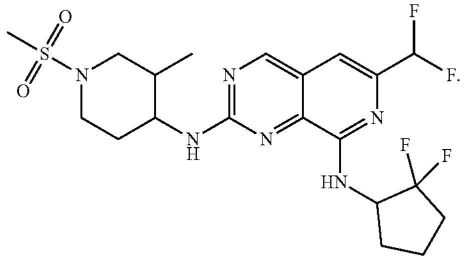
In some embodiments of the present disclosure, the compound is selected from
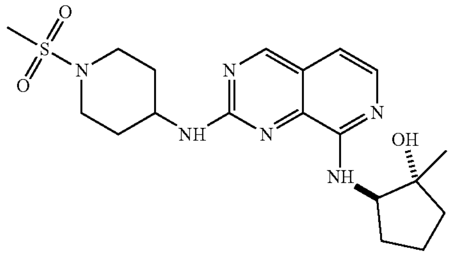
,
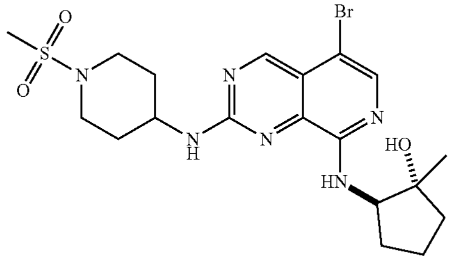
,
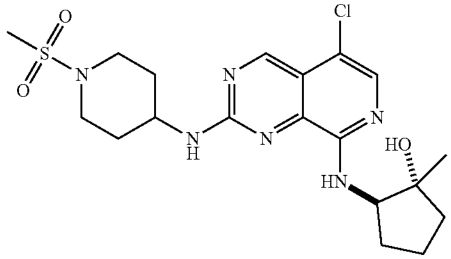
,
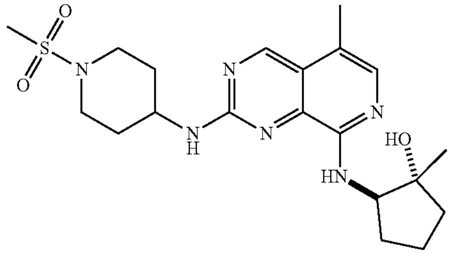
, -continued
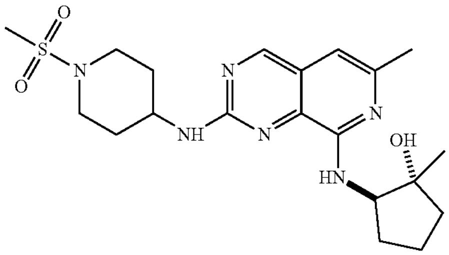
,
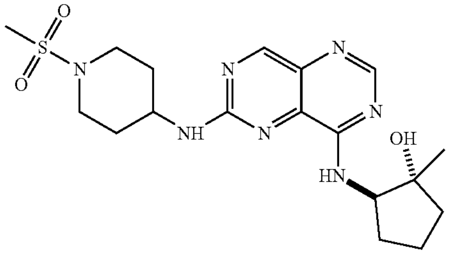
,
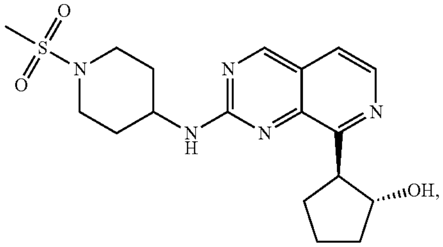
,
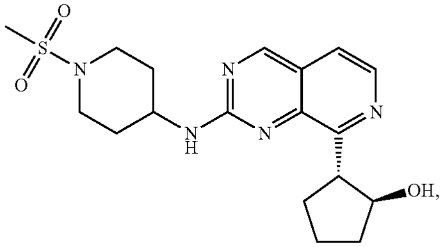
,
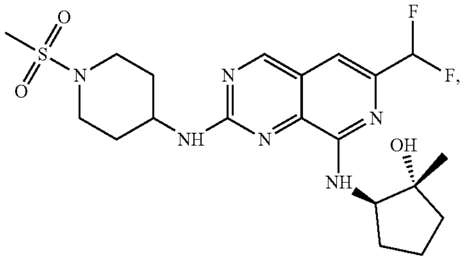
,
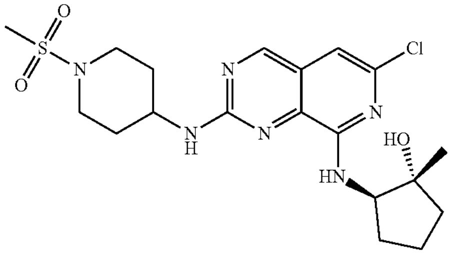
,
-continued
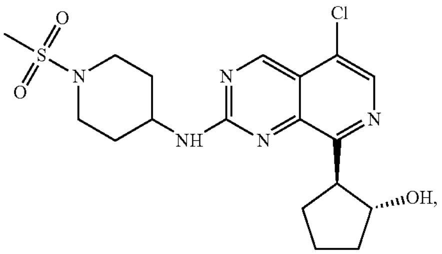
,
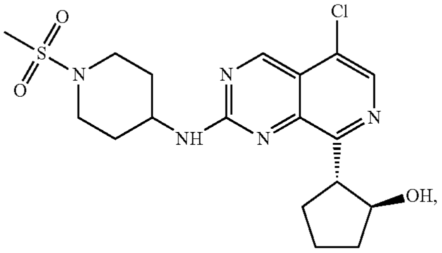
,
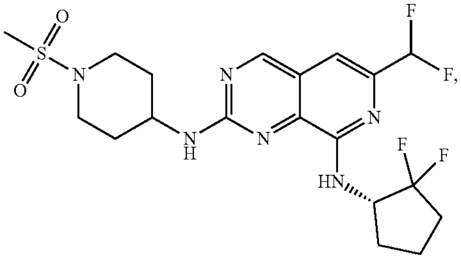
,
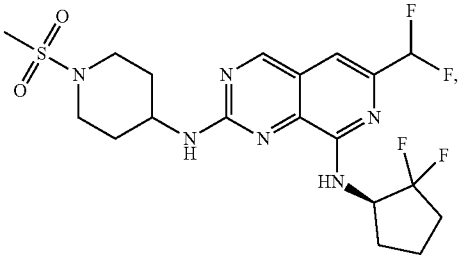
,
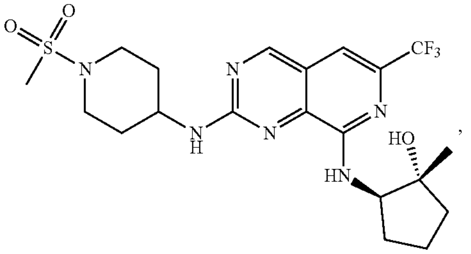
,
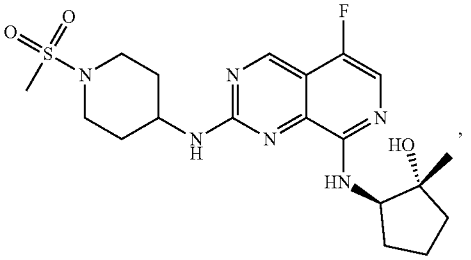
, -continued
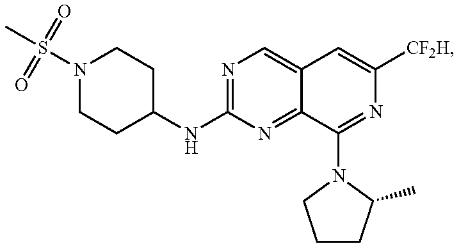
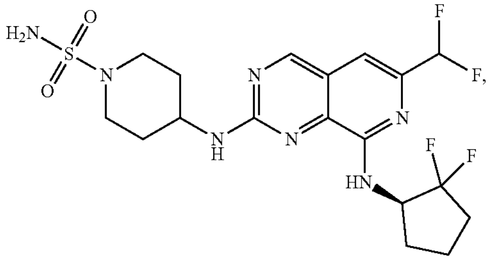
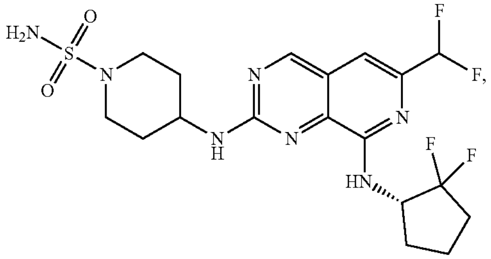
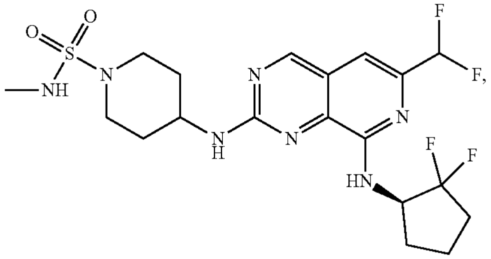
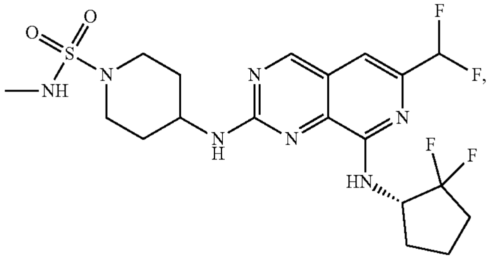
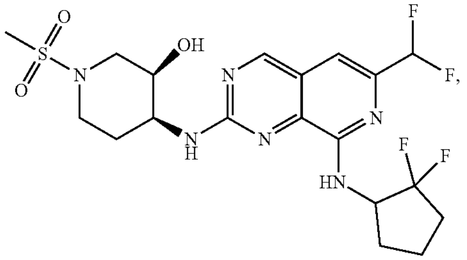
-continued
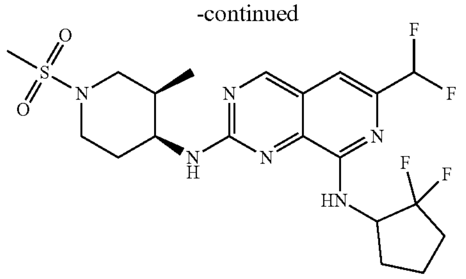
and
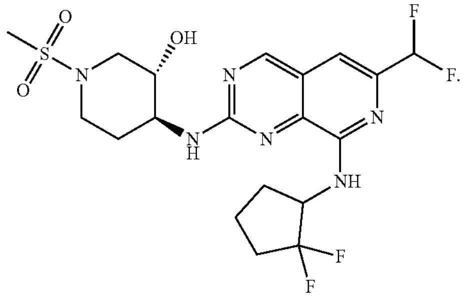
In some embodiments of the present disclosure, the compound is selected from
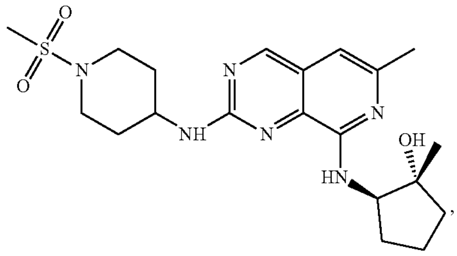
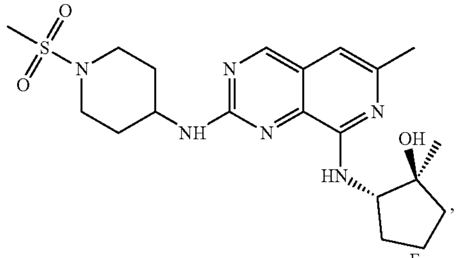
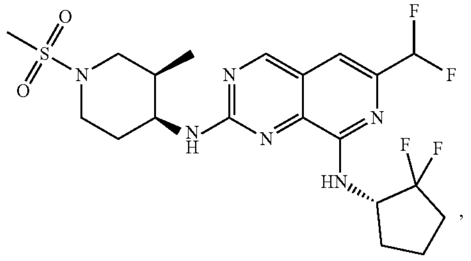
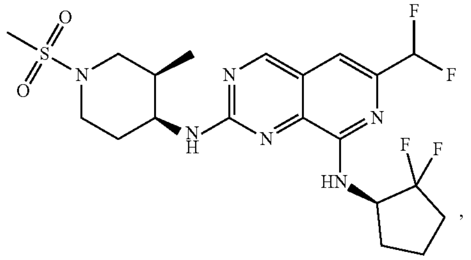

-continued

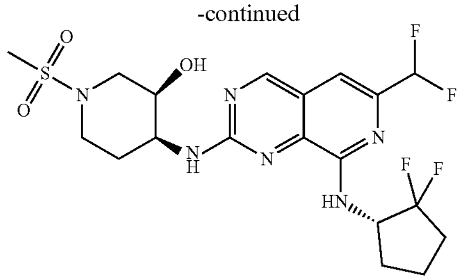

and

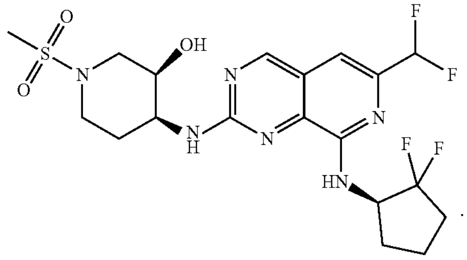

.

The present disclosure also provides a use of the compound in the manufacture of a medicament for the treatment of breast cancer.

The present disclosure also provides some embodiments derived from any combination of above variables.

Technical Effect

The compound of the present disclosure has significant inhibitory effect on CDK2.

Definition and Description

Unless otherwise specified, the following terms and phrases used herein have the following meanings. A specific term or phrase should not be considered indefinite or unclear in the absence of a particular definition, but should be understood according to the common meaning. When a trade name appears herein, it is intended to refer to its corresponding commercial product or active ingredient thereof.

The term "pharmaceutically acceptable" is used herein in terms of those compounds, materials, compositions, and/or dosage forms, which are suitable for use in contact with human and animal tissues within the scope of reliable medical judgment, without excessive toxicity, irritation, anaphylactic reaction or other problems or complications, commensurate with a reasonable benefit/risk ratio.

The term "pharmaceutically acceptable salt" refers to a salt of the compound of the present disclosure that is prepared by reacting the compound having a specific substituent of the present disclosure with a relatively non-toxic acid or base. When the compound of the present disclosure contains a relatively acidic functional group, a base addition salt can be obtained by contacting the compound with a sufficient amount of a base in a pure solution or a suitable inert solvent. The pharmaceutically acceptable base addition salt includes a salt of sodium, potassium, calcium, ammonium, organic amine or magnesium, or similar salts. When the compound of the present disclosure contains a relatively basic functional group, an acid addition salt can be obtained by contacting the compound with a sufficient amount of acid in a pure solution or a suitable inert solvent. Examples of the pharmaceutically acceptable acid addition salt include an inorganic acid salt, wherein the inorganic acid includes, for example, hydrochloric acid, hydrobromic acid, nitric acid, carbonic acid, bicarbonate, phosphoric acid, monohydrogen phosphate, dihydrogen phosphate, sulfuric acid, hydrogen sulfate, hydroiodic acid, phosphorous acid, and the like; and an organic acid salt, wherein the organic acid includes, for example, acetic acid, propionic acid, isobutyric acid, maleic acid, malonic acid, benzoic acid, succinic acid, suberic acid, fumaric acid, lactic acid, mandelic acid, phthalic acid, benzenesulfonic acid, p-toluenesulfonic acid, citric acid, tartaric acid, and methanesulfonic acid, and the like; and salts of amino acid (such as arginine and the like), and a salt of an organic acid such as glucuronic acid and the like. Certain specific compounds of the present disclosure contain both basic and acidic functional groups, thus can be converted to any base or acid addition salt.

The pharmaceutically acceptable salt of the present disclosure can be prepared from the parent compound that contains an acidic or basic moiety by conventional chemical method. Generally, such salt can be prepared by reacting the free acid or base form of the compound with a stoichiometric amount of an appropriate base or acid in water or an organic solvent or a mixture thereof.

The compounds of the present disclosure may exist in specific geometric or stereoisomeric forms. The present disclosure contemplates all such compounds, including cis and trans isomers, (−)- and (+)-enantiomers, (R)- and (S)-enantiomers, diastereoisomers, (D)-isomers, (L)-isomers, and racemic and other mixtures thereof, such as enantiomers or diastereomer enriched mixtures, all of which are within the scope of the present disclosure. Additional asymmetric carbon atoms may be present in substituents such as alkyl. All these isomers and their mixtures are encompassed within the scope of the present disclosure.

Unless otherwise specified, the term "enantiomer" or "optical isomer" refers to stereoisomers that are mirror images of each other.

Unless otherwise specified, the term "cis-trans isomer" or "geometric isomer" is caused by the inability to rotate freely of double bonds or single bonds of ring-forming carbon atoms.

Unless otherwise specified, the term "diastereomer" refers to a stereoisomer in which a molecule has two or more chiral centers and the relationship between the molecules is not mirror images.

Unless otherwise specified, "(D)" or "(+)" refers to dextrorotation, "(L)" or "(−)" refers to levorotation, and "(DL)" or "(±)" refers to racemic.

Unless otherwise specified, the absolute configuration of a stereogenic center is represented by a wedged solid bond () and a wedged dashed bond (), and the relative configuration of a stereogenic center is represented by a straight solid bond () and a straight dashed bond (), a wave line () is used to represent a wedged solid bond () or a wedged dashed bond (), or the wave line () is used to represent a straight solid bond () or a straight dashed bond ().

The compounds of the present disclosure may exist in specific. Unless otherwise specified, the term "tautomer" or "tautomeric form" means that at room temperature, the isomers of different functional groups are in dynamic equilibrium and can be transformed into each other quickly. If tautomers possibly exist (such as in solution), the chemical equilibrium of tautomers can be reached. For example, proton tautomer (also called prototropic tautomer) includes interconversion through proton migration, such as keto-enol isomerization and imine-enamine isomerization. Valence tautomer includes some recombination of bonding electrons for mutual transformation. A specific example of keto-enol tautomerization is the tautomerism between two tautomers of pentane-2,4-dione and 4-hydroxypent-3-en-2-one.

Unless otherwise specified, the terms "enriched in one isomer", "enriched in isomers", "enriched in one enantiomer" or "enriched in enantiomers" refer to the content of one of the isomers or enantiomers is less than 100%, and the content of the isomer or enantiomer is greater than or equal to 60%, or greater than or equal to 70%, or greater than or equal to 80%, or greater than or equal to 90%, or greater than or equal to 95%, or greater than or equal to 96%, or greater than or equal to 97%, or greater than or equal to 98%, or greater than or equal to 99%, or greater than or equal to 99.5%, or greater than or equal to 99.6%, or greater than or equal to 99.7%, or greater than or equal to 99.8%, or greater than or equal to 99.9%.

Unless otherwise specified, the term "isomer excess" or "enantiomeric excess" refers to the difference between the relative percentages of two isomers or two enantiomers. For example, if the content of one isomer or enantiomer is 90%, and the content of the other isomer or enantiomer is 10%, the isomer or enantiomer excess (ee value) is 80%.

Optically active (R)- and (S)-isomer, or D and L isomer can be prepared using chiral synthesis or chiral reagents or other conventional techniques. If one kind of enantiomer of certain compound of the present disclosure is to be obtained, the pure desired enantiomer can be obtained by asymmetric synthesis or derivative action of chiral auxiliary followed by separating the resulting diastereomeric mixture and cleaving the auxiliary group. Alternatively, when the molecule contains a basic functional group (such as amino) or an acidic functional group (such as carboxyl), the compound reacts with an appropriate optically active acid or base to form a salt of the diastereomeric isomer which is then subjected to diastereomeric resolution through the conventional method in the art to give the pure enantiomer. In addition, the enantiomer and the diastereoisomer are generally isolated through chromatography which uses a chiral stationary phase and optionally combines with a chemical derivative method (such as carbamate generated from amine).

The term "optional" or "optionally" means that the subsequently described event or circumstance may, but does not necessarily, occur, and the description includes instances where the event or circumstance occurs and instances where it does not.

The term "substituted" means one or more than one hydrogen atom(s) on a specific atom are substituted by the substituent, including deuterium and hydrogen variables, as long as the valence of the specific atom is normal and the substituted compound is stable. When the substituent is an oxygen (i.e., =O), it means two hydrogen atoms are substituted. Positions on an aromatic ring cannot be substituted with a ketone. The term "optionally substituted" means an atom can be substituted with a substituent or not, unless otherwise specified, the type and number of the substituent may be arbitrary as long as being chemically achievable.

When any variable (such as R) occurs in the constitution or structure of the compound more than once, the definition of the variable at each occurrence is independent. Thus, for example, if a group is substituted by 0-2 R, the group can be optionally substituted by up to two R, wherein the definition of R at each occurrence is independent. Moreover, a combination of the substituent and/or the variant thereof is allowed only when the combination results in a stable compound.

When the number of a linking group is 0, such as $-(CRR)_0-$, it means that the linking group is a single bond, and $-C_0$alkyl-A means that the structure is actually -A.

When the number of a substituent is 0, it means that the substituent does not exist, for example, the structure of $-A-(R)_0$ is actually A.

When a substituent is vacant, it means that the substituent does not exist, for example, when X is vacant in A-X, the structure of A-X is actually A.

When one of the variables is selected from a single bond, it means that the two groups linked by the single bond are connected directly. For example, when L in A-L-Z represents a single bond, the structure of A-L-Z is actually A-Z.

When the bond of a substituent can be cross-connected to two or more atoms on a ring, the substituent can be bonded to any atom on the ring, for example, the structural unit

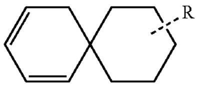

or

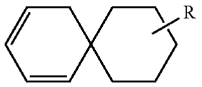

means that the substitution can take place with the substituent R at any position on cyclohexyl or cyclohexadiene. When the enumerative substituent does not indicate by which atom it is linked to the group to be substituted, such substituent can be bonded by any atom thereof. For example, when pyridyl acts as a substituent, it can be linked to the group to be substituted by any carbon atom on the pyridine ring.

When the enumerative linking group does not indicate the direction for linking, the direction for linking is arbitrary, for example, the linking group L contained in

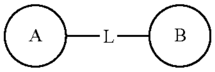

is -M-W—, then -M-W— can link ring A and ring B to form

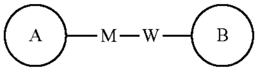

in the direction same as left-to-right reading order, and form

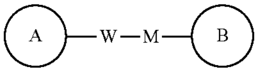

in the direction contrary to left-to-right reading order. A combination of the linking groups, substituents and/or variables thereof is allowed only when such combination can result in a stable compound.

Unless otherwise specified, when a group has one or more linkable sites, any one or more sites of the group can be linked to other groups through chemical bonds. The chemical bond between the site and other groups can be represented by a straight solid bond (), a straight dashed bond () or a wavy line

(  ).

For example, the straight solid bond in —$OCH_3$ means that it is linked to other groups through the oxygen atom in the group; the straight dashed bonds in

means that it is linked to other groups through the two ends of nitrogen atom in the group; the wave lines in

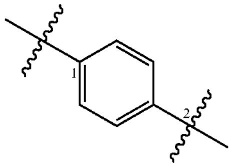 [SMILES: *c1ccc(*)cc1]

means that the phenyl group is linked to other groups through carbon atoms at position 1 and position 2.

Unless otherwise specified, the number of atoms in a ring is generally defined as the number of ring members, for example, "5-7 membered ring" refers to a "ring" with 5-7 atoms arranged around it.

Unless otherwise specified, the term "halo" or "halogen" by itself or as part of another substituent refers to fluorine, chlorine, bromine or iodine atom.

Unless otherwise specified, the term "$C_{1-8}$ alkyl" refers to a linear or branched saturated hydrocarbon group having 1 to 8 carbon atoms. The $C_{1-8}$ alkyl group includes $C_{1-6}$, $C_{1-5}$, $C_{1-4}$, $C_{1-3}$, $C_{1-2}$, $C_{2-6}$, $C_{2-4}$, $C_8$, $C_7$, $C_6$ and $C_5$ alkyl groups and the like; it can be monovalent (such as methyl), divalent (such as methylene) or multivalent (such as methine). Examples of $C_{1-8}$ alkyl include but are not limited to methyl (Me), ethyl (Et), propyl (including n-propyl and isopropyl), butyl (including n-butyl, isobutyl, s-butyl, and t-butyl), pentyl (including n-pentyl, isopentyl and neopentyl), hexyl, heptyl, octyl and the like.

Unless otherwise specified, the term "$C_{1-6}$ alkyl" refers to a linear or branched saturated hydrocarbon group having 1 to 6 carbon atoms. The $C_{1-6}$ alkyl group includes includes $C_{1-5}$, $C_{1-4}$, $C_{1-3}$, $C_{1-2}$, $C_{2-6}$, $C_{2-4}$, $C_6$ and $C_5$ alkyl groups and the like; it can be monovalent (such as methyl), divalent (such as methylene) or multivalent (such as methine). Examples of $C_{1-6}$ alkyl include but are not limited to methyl (Me), ethyl (Et), propyl (including n-propyl and isopropyl), butyl (including n-butyl, isobutyl, s-butyl, and t-butyl), pentyl (including n-pentyl, isopentyl and neopentyl), hexyl and the like.

Unless otherwise specified, the term "$C_{1-3}$ alkyl" refers to a linear or branched saturated hydrocarbon group having 1 to 3 carbon atoms. The $C_{1-3}$ alkyl includes $C_{1-2}$ and $C_{2-3}$ alkyl groups and the like; it can be monovalent (such as methyl), divalent (such as methylene) or multivalent (such as methine). Examples of $C_{1-3}$ alkyl include but are not limited to methyl (Me), ethyl (Et), propyl (including n- and isopropyl) and the like.

Unless otherwise specified, the term "$C_{1-6}$ alkoxy" refers to an alkyl group containing 1 to 6 carbon atoms that are connected to the rest of the molecule through an oxygen atom. The $C_{1-6}$ alkoxy includes $C_{1-4}$, $C_{1-3}$, $C_{1-2}$, $C_{2-6}$, $C_{2-4}$, $C_6$, $C_5$, $C_4$ and $C_3$ alkoxy groups and the like. Examples of $C_{1-6}$ alkoxy include but are not limited to methoxy, ethoxy, propoxy (including n-propoxy and isopropoxy), butoxy (including n-butoxy, isobutoxy group, s-butoxy and t-butoxy), pentyloxy (including n-pentyloxy, isopentyloxy and neopentyloxy), hexyloxy and the like.

Unless otherwise specified, the term "$C_{1-3}$ alkoxy" refers to an alkyl group containing 1 to 3 carbon atoms that are connected to the rest of the molecule through an oxygen atom. The $C_{1-3}$ alkoxy group includes $C_{1-2}$, $C_{2-3}$, $C_3$ and $C_2$ alkoxy groups and the like. Examples of $C_{1-3}$ alkoxy include but are not limited to methoxy, ethoxy, propoxy (including n-propoxy and isopropoxy) and the like.

Unless otherwise specified, the term "halo" or "halogen" by itself or as part of another substituent refers to fluorine, chlorine, bromine or iodine atom.

Unless otherwise specified, "$C_{3-8}$ cycloalkyl" means a saturated cyclic hydrocarbon group composed of 3 to 8 carbon atoms, which includes monocyclic and bicyclic systems, wherein bicyclic systems include spiro rings, fused rings and bridges ring. The $C_{3-8}$ cycloalkyl includes $C_{3-6}$, $C_{3-5}$, $C_{4-8}$, $C_{4-6}$, $C_{4-5}$, $C_{5-8}$ or $C_{5-6}$ cycloalkyl and the like; it can be monovalent, divalent or multivalent. Examples of $C_{3-8}$ cycloalkyl include but are not limited to cyclopropyl, cyclobutyl, cyclopentyl, cyclohexyl, cycloheptyl, norbornyl, [2.2.2]bicyclooctane and the like.

Unless otherwise specified, "$C_{3-6}$ cycloalkyl" means a saturated cyclic hydrocarbon group composed of 3 to 6 carbon atoms, which includes monocyclic and bicyclic systems, and the $C_{3-6}$ cycloalkyl includes $C_{3-5}$, $C_{4-5}$ and $C_{5-6}$ cycloalkyl and the like, it can be monovalent, divalent or multivalent. Examples of $C_{3-6}$ cycloalkyl include, but are not limited to, cyclopropyl, cyclobutyl, cyclopentyl, cyclohexyl and the like.

Unless otherwise specified, "$C_{3-8}$ cycloalkenyl" means a partially unsaturated cyclic hydrocarbon group consisting of 3 to 8 carbon atoms containing at least one carbon-carbon double bond, which includes monocyclic and bicyclic systems, wherein the bicyclic ring system includes spiro rings, fused rings and bridged rings, and any ring in this system is non-aromatic. The $C_{3-8}$ cycloalkenyl includes $C_{3-6}$, $C_{3-5}$, $C_{4-10}$, $C_{4-8}$, $C_{4-6}$, $C_{4-5}$, $C_{5-8}$ or $C_{5-6}$ cycloalkyl and the like; it can be monovalent, divalent or multivalent. Examples of $C_{3-8}$ cycloalkenyl groups include but are not limited to cyclopropenyl, cyclobutenyl, cyclopentenyl, cyclopentadienyl, cyclohexenyl, cyclohexadienyl and the like.

Unless otherwise specified, the term "3-10 membered heterocycloalkyl" by itself or in combination with other terms refers to a saturated cyclic group consisting of 3 to 10 ring atoms, wherein 1, 2, 3 or 4 ring atoms are heteroatoms independently selected from O, S and N, and the rest are carbon atoms, wherein nitrogen atoms are optionally quaternized, and nitrogen, carbon and sulfur heteroatoms can be optionally oxidized (i.e., C(═O), NO and S(O)p, p is 1 or 2). It includes monocyclic, bicyclic and tricyclic ring systems, wherein bicyclic and tricyclic ring systems include spiro, fused and bridged rings. In addition, with regard to the "3-10 membered heterocycloalkyl", a heteroatom may occupy the connection position of the heterocycloalkyl with the rest of the molecule. The 3-10 membered heterocycloalkyl group includes 3-8 membered, 3-6 membered, 3-5 membered, 4-6 membered, 5-6 membered, 4 membered, 5 membered and 6 membered heterocycloalkyl groups and the like. Examples of 3-10 membered heterocycloalkyl include but are not limited to azetidinyl, oxetanyl, thietanyl, pyrrolidinyl, pyrazolidinyl, imidazolidinyl, tetrahydrothiophenyl (including tetrahydrothiophen-2-yl, tetrahydrothiophen-3-yl and the like), tetrahydrofuranyl (including tetrahydrofuran-2-yl and the like), tetrahydropyranyl, piperidinyl (including 1-piperidinyl, 2-piperidinyl, 3-piperidinyl and the like), piperazinyl (including 1-piperazinyl, 2-piperazinyl and the like), morpholinyl (including 3-morpholinyl, 4-morpholinyl and the like), dioxanyl, dithianyl, isoxazolidinyl, isothiazolidinyl, 1,2-oxazinyl, 1,2-thiazinyl, hexahydropyridazinyl, homopiperazinyl, homopiperidyl or dioxepanyl and the like.

Unless otherwise specified, the term "5-6 membered heterocycloalkyl" by itself or in combination with other terms refers to a saturated cyclic group consisting of 5 to 6 ring atoms, wherein 1, 2, 3 or 4 ring atoms are heteroatoms independently selected from O, S and N, and the rest are carbon atoms, wherein nitrogen atoms are optionally quaternized, and carbon, nitrogen and sulfur heteroatoms can be optionally oxidized (i.e., (=), NO and S(O)p, p is 1 or 2). It includes monocyclic and bicyclic systems, wherein the bicyclic systems include spiro ring, fused ring and bridged ring. In addition, with regard to the "5-6 membered heterocycloalkyl", a heteroatom may occupy the connection position of the heterocycloalkyl with the rest of the molecule. The 5-6 membered heterocycloalkyl group includes 5 membered and 6 membered heterocycloalkyl groups. Examples of 5-6 membered heterocycloalkyl include but are not limited to pyrrolidinyl, pyrazolidinyl, imidazolidinyl, tetrahydrothiophenyl (including tetrahydrothiophen-2-yl, tetrahydrothiophen-3-yl and the like), tetrahydrofuranyl (including tetrahydrofuran-2-yl and the like), tetrahydropyranyl, piperidinyl (including 1-piperidinyl, 2-piperidinyl, 3-piperidinyl and the like), piperazinyl (including 1-piperazinyl, 2-piperazinyl and the like), morpholinyl (including 3-morpholinyl, 4-morpholinyl and the like), dioxanyl, dithianyl, isoxazolidinyl, isothiazolidinyl, 1,2-oxazinyl, 1,2-thiazinyl, hexahydropyridazinyl, homopiperazinyl or homopiperidyl and the like.

Unless otherwise specified, the term "3-10 membered heterocycloalkenyl" by itself or in combination with other terms refers to a partially unsaturated cyclic group consisting of 3 to 10 ring atoms containing at least one carbon-carbon double bond, wherein 1, 2, 3 or 4 ring atoms are heteroatoms independently selected from O, S and N, and the rest are carbon atoms, wherein nitrogen atoms are optionally quaternized, and nitrogen, carbon and sulfur heteroatoms can be optionally oxidized (i.e., C(=O), NO and S(O)p, p is 1 or 2). It includes monocyclic, bicyclic and tricyclic systems, wherein the bicyclic and tricyclic systems include spiro ring, fused ring and bridged ring, and at least one ring in this system is non-aromatic. In addition, with regard to the "3-10 membered heterocycloalkenyl", a heteroatom may occupy the connection position of the heterocycloalkenyl with the rest of the molecule. The 3-10 membered heterocycloalkenyl include 3-8 membered, 3-6 membered, 3-5 membered, 4-6 membered, 4-5 membered, 5-6 membered, 4 membered, 5 membered, 6 membered heterocycloalkenyl and the like. Examples of 3-10 membered heterocycloalkenyl include, but are not limited to

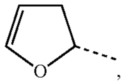
,
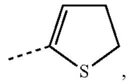
,

-continued

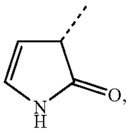
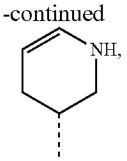
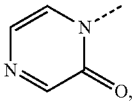
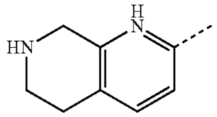
or
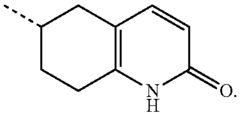

Unless otherwise specified, the terms "5-6 membered heteroaryl ring" and "5-6 membered heteroaryl" in the present disclosure can be used interchangeably, the term "5-6 membered heteroaryl" refers to a single-ring group consisting of 5-6 ring atoms with a conjugated a electron system, wherein 1, 2, 3 or 4 ring atoms are independently selected from O, S and N, and the rest are carbon atoms, wherein nitrogen atoms are optionally quaternized, and nitrogen, carbon and sulfur heteroatoms can be optionally oxidized (i.e., C(=O), NO and S(O)p, p is 1 or 2). A 5-6 membered heteroaryl can be linked to the rest of the molecule through a heteroatom or a carbon atom. The 5-6 membered heteroaryl includes 5 membered and 6 membered heteroaryl. Examples of the 5-6 membered heteroaryl include but are not limited to pyrrolyl (including N-pyrrolyl, 2-pyrrolyl, 3-pyrrolyl and the like), pyrazolyl (including 2-pyrazolyl, 3-pyrazolyl and the like), imidazolyl (including N-imidazolyl, 2-imidazolyl, 4-imidazolyl, 5-imidazolyl and the like), oxazolyl (including 2-oxazolyl, 4-oxazolyl, 5-oxazolyl and the like), triazolyl (1H-1,2,3-triazolyl, 2H-1,2,3-triazolyl, 1H-1,2,4-triazolyl, 4H-1, 2,4-triazolyl and the like), tetrazolyl, isoxazolyl (3-isoxazolyl, 4-isoxazolyl, 5-isoxazolyl and the like), thiazolyl (including 2-thiazolyl, 4-thiazolyl, 5-thiazolyl and the like), furyl (including 2-furyl, 3-furyl and the like), thienyl (including 2-thienyl, 3-thienyl and the like), pyridyl (including 2-pyridyl, 3-pyridyl, 4-pyridyl and the like), pyrazinyl or pyrimidyl (including 2-pyrimidyl, 4-pyrimidyl and the like).

The solvents used in the present disclosure are commercially available.

$IC_{50}$ refers to the concentration of a reagent that produces 50% of the maximum inhibition using the certain reagent.

The following abbreviations are used in the present disclosure: $Pd(t-Bu_3P)_2$ refers to bis(tri-tert-butylphosphine) palladium; $POCl_3$ refers to phosphorus oxychloride; DMAc refers to N,N-dimethylacetamide; m-CPBA refers to m-chloroperoxybenzoic acid; DMSO refers to dimethyl sulfoxide; DMF refers to N,N-dimethylformamide; NMP refers to N-methylpyrrolidone; DIPEA refers to N,N-diisopropylethylamine; DBU refers to 1.8-diazabicyclo[5.4.0]undec-7-ene; NBS refers to N-bromobisbutyrimide; NCS refers to N-chlorobisbutyrimide; p-TSA refers to p-toluenesulfonic acid; TBSCl refers to tert-butyldimethyl chlorosilane; $Pd(dppf)Cl_2$ refers to [1,1'-bis(diphenylphosphino)ferrocene]dichloropalladium; $Rh(PPh_3)_3Cl$ refers to tri(triphenylphosphine) rhodium chloride; DAST refers to diethylaminosulfur trifluoride; AIBN refers to azobisisobutyronitrile; NMO refers to N-methylmorpholine oxide.

The compounds of the present disclosure are named according to the conventional naming principles in the art or by ChemDraw® software, and the commercially available compounds use the supplier catalog names.

Unless otherwise specified, the proportions of solvents used in the silica gel column chromatography of the present disclosure are volume ratios.

DETAILED DESCRIPTION OF THE PREFERRED EMBODIMENT

The present disclosure is described in detail by the embodiments below, but it does not mean that there are any adverse restrictions on the present disclosure. The compounds of the present disclosure can be prepared by a variety of synthetic methods known to those skilled in the art, including the specific embodiments listed below, the embodiments formed by their combination with other chemical synthesis methods, and equivalent alternatives known to those skilled in the art, preferred embodiments include but are not limited to the embodiments of the present disclosure. It will be apparent to those skilled in the art that various variations and improvements can be made to specific embodiments of the present disclosure without departing from the spirit and scope of the present disclosure.

Synthesis of Intermediate A

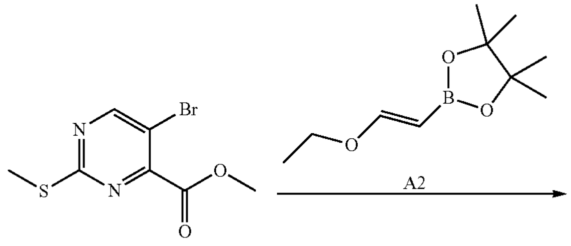

A1

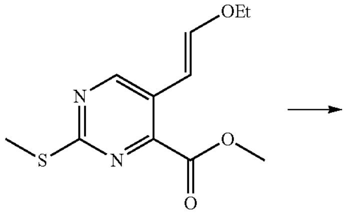

A3

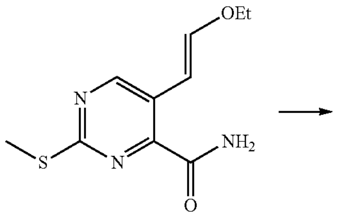

A4

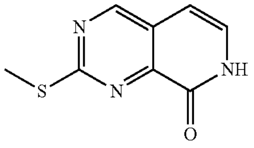

Intermediate A

Step 1:

Compound A1 (1.5 g, 5.70 mmol, 1 eq), compound A2 (1.69 g, 8.55 mmol, 1.5 eq), sodium carbonate (1.21 g, 11.40 mmol, 2 eq), and Pd(t-$Bu_3P)_2$ (145.68 mg, 285.05 μmol, 0.05 eq) were dissolved in a mixed solution of water (5 mL) and tetrahydrofuran (15 mL), and the resulting mixture was replaced with nitrogen three times and reacted at 65° C. for 16 hours. The reaction solution was concentrated under reduced pressure, diluted with water (50 mL), extracted with ethyl acetate (50 mL), and the organic phase was washed with saturated brine (50 mL), dried over anhydrous sodium sulfate, filtered and concentrated. The obtained residue was purified by silica gel column chromatography (petroleum ether/ethyl acetate=10/1) to obtain compound A3. LCMS (ESI) m/z: 255.1 (M+1).

Step 2:

Ammonia (7 mol/L, 30 mL, 47.60 eq) was passed into a solution of compound A3 (1.06 g, 4.41 mmol, 1 eq) in methanol (30 mL), the mixture was stirred in a seal-tube at 85° C. for 16 hours. The reaction solution was concentrated under reduced pressure to obtain compound A4. LCMS (ESI) m/z: 240.1 (M+1).

Step 3:

p-TSA (282 mg, 164 mmol, 0.437 eq) was added to a solution of compound A4 (897 mg, 3.75 mmol) in toluene (20 mL), the mixture was reacted at 90° C. for 1.5 hours. The reaction solution was concentrated under reduced pressure to obtain residue, and then washed with petroleum ether to obtain Intermediate A. LCMS (ESI) m/z: 194.1 (M+1).

Embodiment 1: Preparation of Compound 1

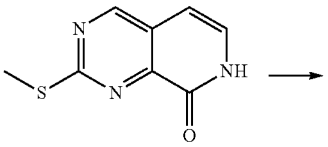

Intermediate A

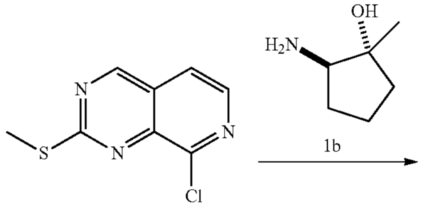

1a

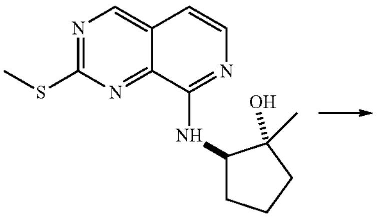

1c

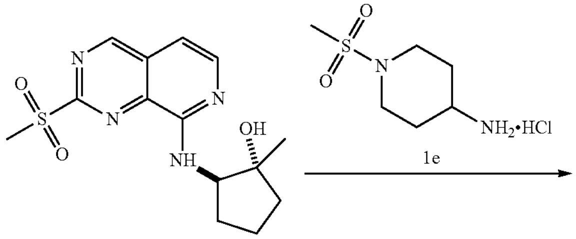

1d

-continued

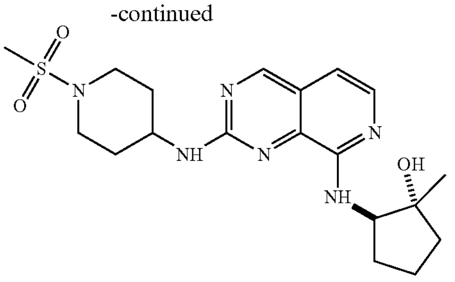

1

Step 1:

Intermediate A (890 mg, 4.61 mmol, 1 eq) was dissolved in $POCl_3$ (10 mL), and the resulting solution was replaced with nitrogen three times and reacted at 70° C. for 1.5 hours. The reaction solution was added dropwise to a mixture of water (50 mL) and ethyl acetate (50 mL), and the obtained organic phase was washed with saturated brine (50 mL), dried over anhydrous sodium sulfate and filtered, and the filtrate was concentrated to obtain compound 1a. LCMS (ESI) m/z: 211.8. (M+1).

Step 2:

Triethylamine (982.40 mg, 9.71 mmol, 1.35 mL, 3 eq) was added to a solution of compound 1a (685 mg, 3.24 mmol, 1 eq) and compound 1b (559.08 mg, 4.85 mmol, 1.5 eq) in DMAc (10 mL), the mixture was reacted at 130° C. for 16 hours. Then the reaction solution was added to the mixture of water (50 mL) and ethyl acetate (50 mL), and the obtained organic phase was washed with saturated brine (50 mL*5), dried over anhydrous sodium sulfate and filtered, and the filtrate was concentrated. The obtained residue was purified by silica gel column chromatography (petroleum ether/ethyl acetate=2/1) to obtain compound 1c. LCMS (ESI) m/z: 291.2 (M+1).

Step 3:

At 0° C., m-CPBA (647.77 mg, 3.75 mmol, 2.0 eq) was added to a solution of compound 1c (545 mg, 1.88 mmol, 1 eq) in dichloromethane (10 mL), and the reaction was carried out at 15° C. for 16 hours. A mixture of water (50 mL) and ethyl acetate (50 mL) was added to the reaction solution, and the obtained organic phase was washed with water (50 mL), dried over anhydrous sodium sulfate, filtered, and the filtrate was concentrated. The obtained residue was purified by preparative thin-layer chromatography silica-gel plate (petroleum ether/ethyl acetate=1/2) to obtain compound 1d. LCMS (ESI) m/z: 323.1 (M+1).

Step 4:

1e (255.55 mg, 1.19 μmol, 1.5 eq, hydrochloride salt) and DIPEA (512.75 mg, 3.97 mmol, 5 eq) were added to a solution of compound 1d (255.80 mg, 793.47 μmol, 1 eq) in DMSO (5 mL), the reaction solution was reacted at 60° C. for 23 hours. LC-MS showed that 30% of the starting material was remained, and the target product was detected. The reaction solution was stirred at 60° C. for another 2 hours. A mixture of water (50 mL) and ethyl acetate (50 mL) was added to the reaction solution, and the layers were separated, the obtained organic phase was washed with saturated brine (50 mL), dried over anhydrous sodium sulfate, filtered, and the filtrate was concentrated. The obtained residue was purified by preparative HPLC (chromatographic column: Waters Xbridge 150*25 mm*5 μm; mobile phase A: 10 mmol/L ammonium bicarbonate aqueous solution; mobile phase B: acetonitrile; gradient elution: 20%-50%, 10 minutes) to obtain compound 1. $^1H$ NMR (400 MHz, $CDCl_3$) δ 8.88 (s, 1H), 7.69 (d, J=6.2 Hz, 1H), 6.74 (d, J=6.0 Hz, 1H), 6.37 (d, J=2.8 Hz, 1H), 5.29 (d, J=3.6 Hz, 1H), 4.12-4.09 (m, 2H), 3.81-3.78 (m, 2H), 3.00 (m, 2H), 2.85 (s, 3H), 2.29-2.22 (m, 3H), 2.01-1.88 (m, 1H), 1.75-1.73 (m, 2H), 1.71-1.59 (m, 5H), 1.13 (s, 3H); LCMS (ESI) m/z: 421.3 (M+1).

Embodiment 2: Preparation of Compound 2

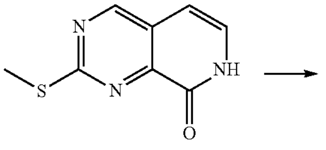

Intermediate A

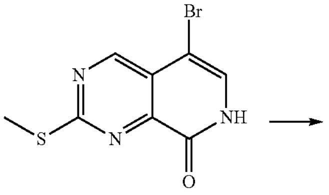

2a

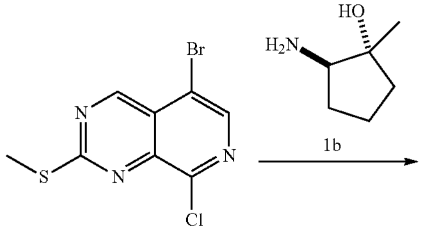

2b

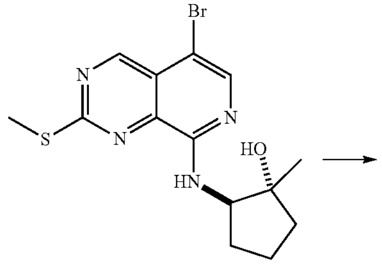

2c

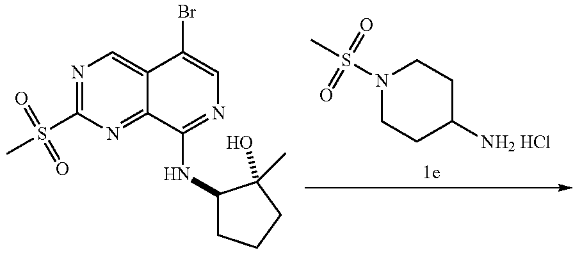

2d

-continued

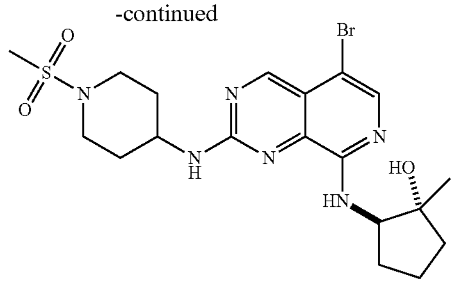

2

Step 1:

Intermediate A (0.64 g, 3.31 mmol, 1 eq) and NBS (648.47 mg, 3.64 mmol, 1.1 eq) were dissolved in DMF (10 mL), and the reaction solution was stirred at 25° C. for 0.5 h. The reaction solution was poured into water (30 mL), filtered, and the filter cake was dried to obtain compound 2a. LCMS (ESI) m/z: 274.0 (M+1).

Step 2:

Compound 2a (0.53 g, 1.95 mmol, 1 eq) was dissolved in $POCl_3$ (16.50 g, 107.61 mmol, 10 ml, 55.25 eq), and the resulting mixed solution was replaced with nitrogen three times and reacted at 70° C. for 1 hour. The reaction solution was quenched with water (10 mL), and extracted with ethyl acetate (10 mL*2). The combined organic phase was washed with saturated brine (10 mL), dried over sodium sulfate, filtered, and the filtrate was concentrated to obtain compound 2b. LCMS (ESI) m/z: 292.0 (M+1).

Step 3:

Triethylamine (710.43 mg, 7.02 mmol, 3 eq) was added to a solution of compound 2b (0.68 g, 2.34 mmol, 1 eq) and compound 1b (404.30 mg, 3.51 mmol, 1.5 eq) in DMAc (10 mL), and the mixture was reacted at 130° C. for 12 h. The reaction solution was diluted with water (10 mL), and extracted with ethyl acetate (5 mL*3). The combined organic phase was washed with saturated brine (10 mL), dried over sodium sulfate, filtered, and the filtrate was concentrated to obtain compound 2c. LCMS (ESI) m/z: 371.0 (M+1).

Step 4:

m-CPBA (1.23 g, 5.69 mmol, 2.5 eq) was added to a solution of compound 2c (0.84 g, 2.27 mmol, 1 eq) in dichloromethane (10 mL) at 0° C., and the reaction was reacted at 25° C. for 3 h. Saturated sodium sulfite aqueous solution (5 mL) was added to the reaction solution, and then extracted with dichloromethane (30 mL*3). The combined organic phase was washed with saturated brine (10 mL), dried over anhydrous sodium sulfate and filtered, and the filtrate was concentrated to give a residue, the residue was purified by preparative thin-layer chromatography silica-gel plate (petroleum ether/ethyl acetate=3/1), to obtain compound 2d. LCMS (ESI) m/z: 403.3 (M+1).

Step 5:

DIPEA (322.07 mg, 2.49 mmol, 5 eq) was added to a solution of compound 2d (0.2 g, 498.41 μmol, 1 eq) and compound 1e (160.52 mg, 747.61 μmol, hydrochloride salt, 1.5 eq) in DMSO (5 mL), and the reaction was carried out at 60° C. for 12 hours. The reaction solution was diluted with water (5 mL) and extracted with ethyl acetate (5 mL*3). The combined organic phase was washed with saturated brine (10 mL), dried over anhydrous sodium sulfate, filtered and concentrated. The obtained residue was purified by preparative HPLC (column: Xtimate C18 150*40 mm*10 μm; mobile phase A: water (containing 0.05% ammonia); mobile phase B: acetonitrile; gradient elution: 34%-64%, 10 minutes) to obtain compound 2. LCMS (ESI) m/z: 501.1 (M+1); $^1H$ NMR (400 MHz, $CD_3OD$) δ 9.07 (s, 1H), 7.70 (s, 1H), 4.62 (br s, 2H), 4.26-4.09 (m, 2H), 3.75 (br d, J=11.6 Hz, 2H), 3.02 (br t, J=11.4 Hz, 2H), 2.90 (s, 3H), 2.35 (br d, J=8.1 Hz, 1H), 2.18 (br d, J=9.9 Hz, 2H), 1.92-1.75 (m, 5H), 1.22 (s, 3H).

Embodiment 3: Preparation of Compound 3

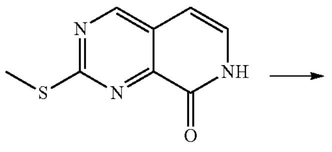

Intermediate A

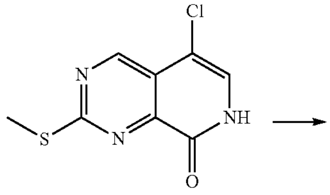

3a

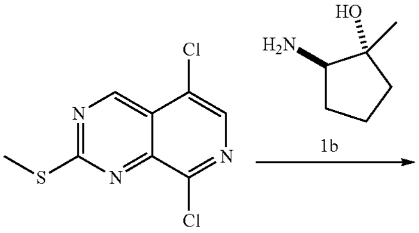

3b

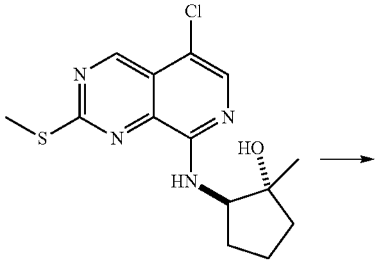

3c

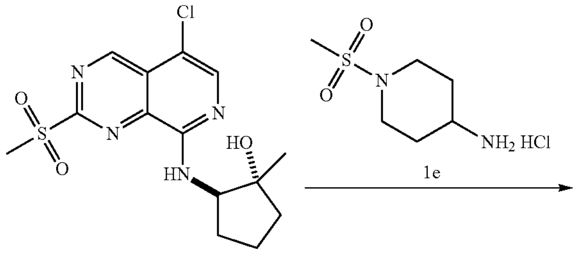

3d

-continued

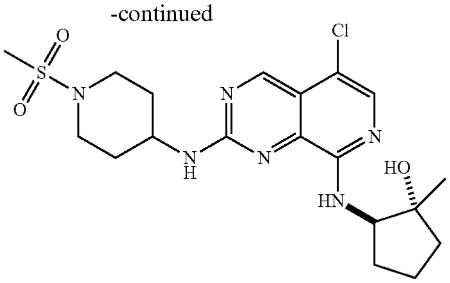

3

Step 1:

Intermediate A (0.5 g, 2.59 mmol, 1 eq) and NCS (380.09 mg, 2.85 mmol, 1.1 eq) were dissolved in DMF (5 mL) and the reaction solution was stirred at 25° C. for 0.5 h. The reaction solution was poured into water (30 mL), filtered, and the filter cake was dried to obtain compound 3a. LCMS (ESI) m/z: 228.0 (M+1).

Step 2:

Compound 3a (0.15 g, 658.85 mmol, 1 eq) was dissolved in $POCl_3$ (9.9 g, 64.57 mmol, 6 mL, 98 eq), and the resulting mixed solution was replaced with nitrogen three times and reacted at 70° C. for 1.5 hours. The reaction solution was quenched with water (10 mL) and extracted with ethyl acetate (50 mL*3). The combined organic phases was washed with saturated brine (10 mL), dried over sodium sulfate, filtered and the filtrate was concentrated to obtain compound 3b. LCMS (ESI) m/z: 246.0 (M+1).

Step 3:

Triethylamine (135.68 mg, 1.34 mmol, 3 eq) was added to a solution of compound 3b (0.11 g, 446.94 μmol, 1 eq) and compound 1b (51.48 mg, 446.94 μmol, 1 eq) in DMAc (5 mL), and the mixture was reacted at 130° C. for 12 h. The reaction solution was diluted with water (10 mL), and extracted with ethyl acetate (5 mL*3). The combined organic phase was washed with saturated brine (10 mL), dried over sodium sulfate, filtered and the filtrate was concentrated to obtain compound 3c. LCMS (ESI) m/z: 325.2 (M+1).

Step 4:

At 0° C., m-CPBA (467.50 mg, 2.71 mmol, 2 eq) was added to a solution of compound 3c (0.44 g, 1.35 mmol, 1 eq) in dichloromethane (5 mL), and the reaction was carried out at 25° C. for 3 h. The reaction solution was added with saturated sodium sulfite aqueous solution (5 mL) and extracted with dichloromethane (5 mL*3). The combined organic phase was washed with saturated brine (10 mL), dried over anhydrous sodium sulfate, filtered and the filtrate was concentrated. The residue was purified by preparative thin-layer chromatography silica-gel plate (petroleum ether/ethyl acetate=3/1), to obtain compound 3d. LCMS (ESI) m/z: 357.1 (M+1).

Step 5:

DIPEA (307.87 mg, 2.38 mmol, 5 eq) was added to a solution of compound 3d (0.17 g, 476.42 μmol, 1 eq) and compound 1e (153.44 mg, 714.63 μmol, 1.5 eq, hydrochloride salt) in DMSO (5 mL), and the reaction was carried out at 60° C. for 5 hours. The reaction solution was diluted with water (5 mL) and extracted with ethyl acetate (5 mL*3). The combined organic phase was washed with saturated brine (10 mL), dried over anhydrous sodium sulfate, filtered and the filtrate was concentrated. The residue was purified by preparative HPLC (column: Xtimate C18 150*40 mm*10 μm; mobile phase A: water (containing 0.05% ammonia); mobile phase B: acetonitrile; gradient elution: 33%-63%, 10 minutes) to obtain compound 3. LCMS (ESI) m/z: 455.1 (M+1); $^1H$ NMR (400 MHz, $CD_3OD$) δ 9.15 (s, 1H), 7.60 (s, 1H), 4.61 (br s, 2H), 4.22-4.08 (m, 2H), 3.82-3.69 (m, 2H), 3.02 (br t, J=10.8 Hz, 2H), 2.90 (s, 3H), 2.39-2.29 (m, 1H), 2.18 (br dd, J=2.6, 12.9 Hz, 2H), 1.85-1.70 (m, 5H), 1.22 (s, 3H).

Embodiment 4: Preparation of Compound 4

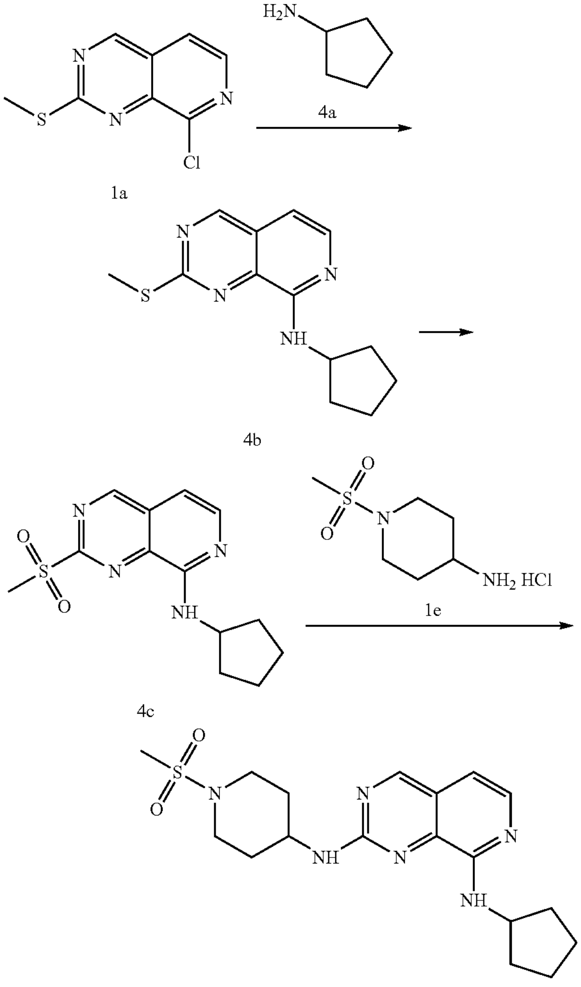

1a
4b
4c
4

Step 1:

Potassium carbonate (1.43 mg, 10.32 mmol, 3 eq) was added to a solution of compound 1a (728 mg, 3.44 mmol, 1 eq) and compound 4a (585.7 mg, 6.88 mmol, 678.67 μL, 2 eq) in DMAc (10 mL), and the mixture was reacted at 120° C. for 16 h. The reaction solution was added to a mixed solution of ethyl acetate (150 mL) and water (150 mL), the obtained organic phase was washed with water (150 mL), dried over anhydrous sodium sulfate, filtered and the filtrate was concentrated. The obtained residue was purified by silica gel column chromatography (petroleum ether/ethyl acetate=10/1) to obtain compound 4b. LCMS (ESI) m/z: 261.4 (M+1).

Step 2:

m-CPBA (0.838 g, 3.89 mmol, 2.2 eq) was added to a solution of compound 4b (0.46 g, 1.77 mmol, 1 eq) in dichloromethane (5 mL) at 0° C., and the reaction was carried out at 25° C. for 3 h. The reaction solution was added to a mixed solution of ethyl acetate (50 mL) and water (50 mL), and the obtained organic phase was washed with water (50 mL), dried over anhydrous sodium sulfate, filtered and the filtrate was concentrated. The residue was purified by preparative thin-layer chromatography silica-gel plate (petroleum ether/ethyl acetate=1/1) to obtain compound 4c. LCMS (ESI) m/z: 293.1 (M+1).

Step 3:

DIPEA (338.19 mg, 2.62 mmol, 3 eq) was added to a solution of compound 4c (0.255 g, 872.22 μmol, 1 eq) and compound 1e (280 mg, 1.3 μmol, 1.5 eq, hydrochloride salt) in DMSO (3 mL), and the reaction was carried out at 80° C. for 18 hours. The reaction solution was purified by preparative HPLC (column: Waters Xbridge 150*25 mm*5 μm; mobile phase A: 10 mmol/L ammonium bicarbonate aqueous solution; mobile phase B: acetonitrile; gradient elution: 35%-65%, 10 minutes) to obtain compound 4. LCMS (ESI) m/z: 391.3 (M+1); $^{1}$H NMR (400 MHz, CDCl3) δ 8.85 (s, 1H), 7.82 (d, J=5.60 Hz, 1H), 6.68 (d, J=5.60 Hz, 1H), 6.29 (d, J=5.60 Hz, 1H), 5.21 (d, J=5.60 Hz, 1H), 4.44-4.49 (m, 1H), 4.1-4.21 (m, 1H), 3.76-3.80 (m, 2H), 3.50 (s, 1H), 3.00-3.04 (m, 2H), 2.85 (s, 3H), 2.18-2.26 (m, 5H), 1.72-1.78 (m, 6H).

Embodiment 5: Preparation of Compound 5

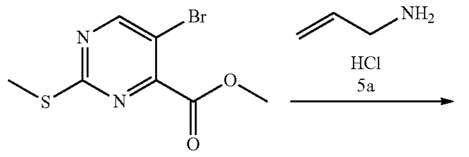

A1

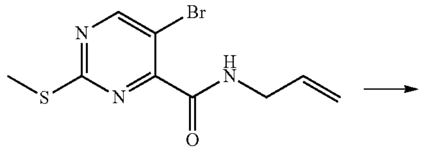

5b

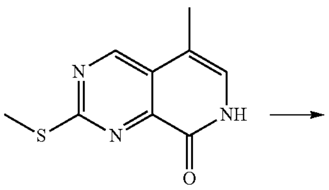

5c

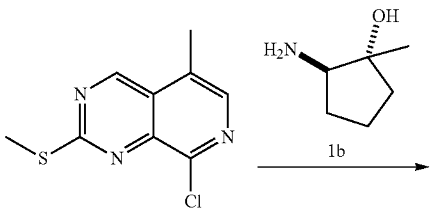

5d

-continued

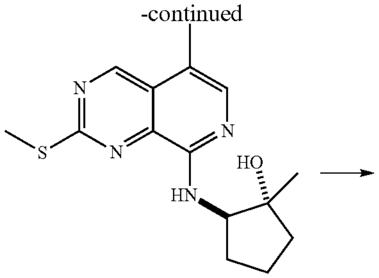

5e

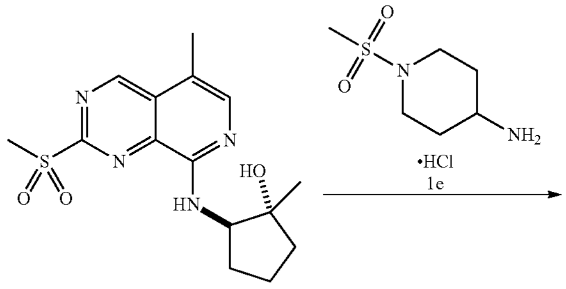

5f

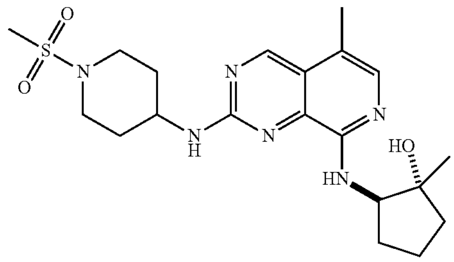

5

Step 1:

Compound A1 (6 g, 22.80 mmol, 1 eq), compound 5a (21.33 g, 228.04 mmol, 28.03 mL, 10 eq) and DBU (34.72 g, 228.04 mmol, 34.37 mL, 10 eq) were dissolved in methanol (40 mL), the reaction solution was reacted in a seal-tube at 90° C. for 18 hours. The reaction solution was concentrated under reduced pressure, and the residue was diluted with ethyl acetate (200 mL), the organic phase was washed with a solution (200 mL) of hydrochloric acid in water at pH 3, dried over anhydrous sodium sulfate, filtered and the filtrate was concentrated. The residue product was purified by silica gel column chromatography (petroleum ether/ethyl acetate=10/1) to obtain compound 5b. LCMS (ESI) m/z: 290.0 (M+1).

Step 2:

Compound 5b (2.6 g, 9.02 mmol, 1 eq), trans-di(acetato) bis[o-(di-o-tolylphosphino)benzyl]dipalladium(II) (169.20 mg, 180.45 mmol, 0.02 eq) and DIPEA (4.66 g, 36.09 mmol, 6.29 mL, 4 eq) were dissolved in DMAc (50 mL), the reaction solution was reacted in a seal-tube at 150° C. for 18 hours. LCMS showed the starting material was completely consumed. The reaction solution was added to a mixed solution of water (150 mL) and dichloromethane (150 mL), separated, the organic phase was washed with water (200 mL), and dried over anhydrous sodium sulfate, filtered and the filtrate was concentrated. The residue product was purified by silica gel column chromatography (dichloromethane/methanol=10/1) to obtain compound 5c. LCMS (ESI) m/z: 208.6 (M+1).

Step 3:

Compound 5c (0.96 g, 2.96 mmol, 1 eq) was dissolved in $POCl_3$ (25 mL), and the resulting mixed solution was reacted at 70° C. for 3 hours. The reaction solution was concentrated, and saturated sodium bicarbonate solution (250 mL) and ethyl acetate (250 mL) were added to the obtained residue, and extracted with ethyl acetate (250 mL). The combined organic phase was washed with saturated brine (250 mL), and dried over anhydrous sodium sulfate, filtered and the filtrate was concentrated. The residue product was purified by silica gel column chromatography (petroleum ether/ethyl acetate=10/1) to obtain compound 5d. LCMS (ESI) m/z: 226.4 (M+1).

Step 4:

Triethylamine (589.57 mg, 5.83 mmol, 810.96 μl, 5 eq) was added to a solution of compound 5d (263 mg, 1.17 mmol, 1 eq) and compound 1b (201.31 mg, 1.75 mmol, 1.5 eq) in NMP (3 mL), and the mixture was reacted at 130-150° C. for 44 h. The reaction solution was diluted with water (150 mL) and extracted with ethyl acetate (150 mL). The combined organic phase was washed with water (150 mL), dried over anhydrous sodium sulfate, filtered and the filtrate was concentrated. The residue was purified by silica gel chromatography plate (petroleum ether/ethyl acetate=2/1) to obtain compound 5e. LCMS (ESI) m/z: 305.2 (M+1).

Step 5:

m-CPBA (0.15 g, 0.87 mmol, 2.2 eq) was added to a solution of compound 5e (0.12 g, 0.39 mmol, 1 eq) in dichloromethane (3 mL), and the reaction was carried out at 25° C. for 2 h. A mixture of water (50 mL) and ethyl acetate (50 mL) was added to the reaction solution, and the organic phase was washed with water (50 mL), dried over anhydrous sodium sulfate, filtered and the filtrate was concentrated. The residue was purified by preparative silica-gel plate (petroleum ether/ethyl acetate=1/1), to obtain compound 5f. LCMS (ESI) m/z: 337.2 (M+1).

Step 6:

DIPEA (97.97 mg, 758.01 mmol, 5 eq) was added to a solution of compound 5f (51 mg, 151.6 μmol, 1 eq) and compound 1e (65.1 mg, 303.20 μmol, 1.5 eq, hydrochloride salt) in DMSO (1 mL), and the reaction was carried out at 100° C. for 72 h. The reaction solution was purified by preparative HPLC (column: Xtimate C18 150*40 mm*10 μm; mobile phase A: water (containing 0.05% ammonia); mobile phase B: acetonitrile; gradient elution: 27%-57%, 10 minutes) to obtain compound 5. $^1H$ NMR (400 MHz, $CDCl_3$) δ 8.88 (s, 1H), 7.70 (d, J=6.0 Hz, 1H), 6.74 (d, J=6.0 Hz, 1H), 6.38 (d, J=2.8 Hz, 1H), 5.39 (d, J=7.6 Hz, 1H), 4.12-4.01 (m, 2H), 3.81-3.78 (m, 2H), 3.00 (m, 2H), 2.85 (s, 3H), 2.29-2.01 (m, 3H), 1.89 (m, 1H), 1.76-1.74 (m, 2H), 1.73-1.65 (m, 6H), 1.14 (s, 3H); LCMS (ESI) m/z: 435.2 (M+1).

Embodiment 6: Preparation of Compound 6

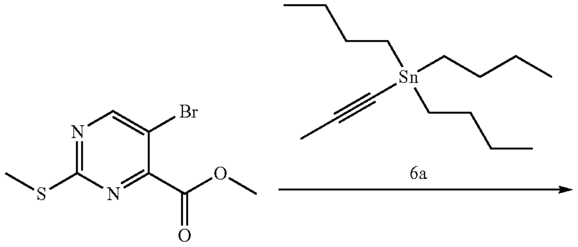

A1

-continued

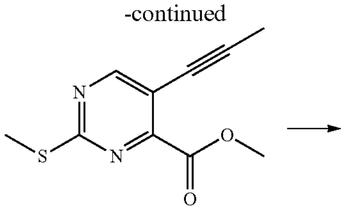

6b

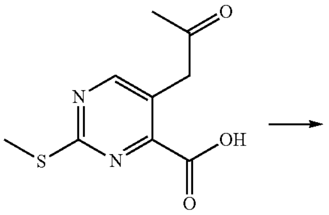

6c

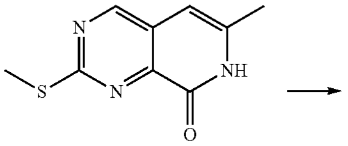

6d

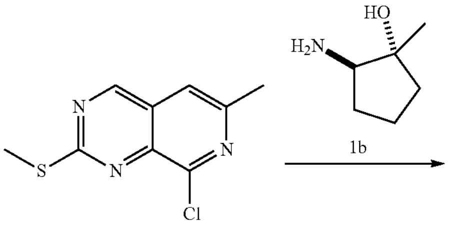

6e

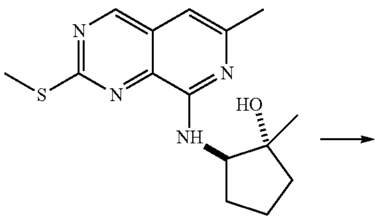

6f

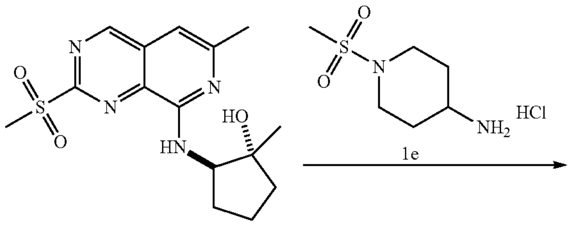

6g

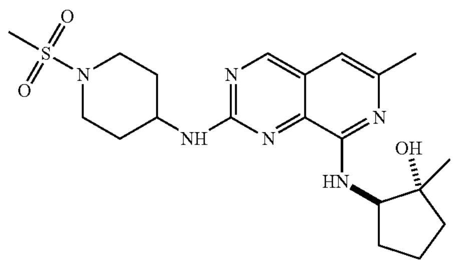

6

Step 1:

Compound A1 (10 g, 38.01 mmol, 1 eq), compound 6a (15.01 g, 45.61 mmol, 1.2 eq), and $Pd(1-Bu_3P)_2$ (971.17 mg, 1.90 mmol, 0.05 eq) was dissolved in DMF (100 mL), and the solution was stirred at 130° C. for 2 hours. The reaction mixture was cooled to 20° C., potassium fluoride (7 g) was added, and the resulting mixture was stirred at 20° C. for 15 minutes. The reaction mixture was filtered, water (100 mL) was added to the filtrate, and the mixture was extracted with ethyl acetate (100 mL*2). The combined organic phase was washed with saturated brine (100 mL*2), dried over anhydrous sodium sulfate, filtered and the filtrate was concentrated. The obtained residue was purified by silica gel column chromatography (petroleum ether/ethyl acetate=15/1-5/1) to obtain compound 6b. $^1$H NMR (400 MHz, $CDCl_3$) δ 8.66 (s, 1H), 4.04-3.97 (m, 3H), 2.65-2.55 (m, 3H), 2.13 (s, 3H). LCMS (ESI) m/z: 223.4 (M+1).

Step 2:

A mixture solution of compound 6b (5 g, 22.50 mmol, 1 eq), mercury sulfate (6.67 g, 22.50 mmol, 1 eq) and sulfuric acid (12 mol/L, 3.75 mL, 2 eq) in acetone (120 mL) and water (30 mL) was heated to 80° C. and stirred for 14 h. The reaction mixture was concentrated and water (100 mL) was added, and the mixture was filtered. The filtrate was extracted with dichloromethane (100 mL*5). The combined organic phase was washed with saturated brine (200 mL*2), dried over anhydrous sodium sulfate, filtered and concentrated. The obtained residue was purified by preparative HPLC (column: Phenomenex luna C18 250*50 mm*10 μm; mobile phase A: water (containing 0.05% hydrochloric acid); mobile phase B: acetonitrile; gradient elution: 0%-30%, 18 minutes) to obtain compound 6c. LCMS (ESI) m/z: 227.0 (M+1); $^1$H NMR (400 MHz, $CDCl_3$) δ 8.54 (s, 1H), 4.29-4.13 (m, 2H), 2.64 (s, 3H), 2.39 (s, 3H).

Step 3:

Ammonia (5.96 g, 350.00 mmol, 31.68 eq) was bubbled into ethanol (50 mL) at −30° C. to obtain an ammonia/ethanol solution (7 mol/L, 50 mL). Compound 6c (2.5 g, 11.05 mmol, 1 eq) was added to the above ammonia/ethanol solution, the mixture was reacted in a 30 mL seal-tube at 130° C. (oil temperature) and stirred for 16 hours. The reaction mixture was concentrated under reduced pressure to obtain compound 6d. LCMS (ESI) m/z: 208.1 (M+1).

Step 4:

A solution of compound 6d (1 g, 4.83 mmol, 1 eq) in $POCl_3$ (10 mL) was stirred at 50° C. for 0.5 h. The reaction mixture was diluted with ethyl acetate (50 mL), and the resulting mixture was dropped slowly to a stirred mixture of saturated sodium bicarbonate (100 mL) and ethyl acetate (50 mL). The organic phase was washed with saturated brine (100 mL*1), dried over anhydrous sodium sulfate, filtered and the filtrate was concentrated. The obtained residue was purified by silica gel column chromatography silica-gel plate (petroleum ether/ethyl acetate=2/1) to obtain compound 6e. LCMS (ESI) m/z: 226.8 (M+1).

Step 5:

A solution of compound 6e (0.1 g, 443.07 μmol, 1 eq), compound 1b (56.13 mg, 487.38 μmol, 1.1 eq) and triethylamine (89.67 mg, 886.14 μmol, 123.34 μL, 2 eq) in DMAc (2 mL) was heated to 120° C. and stirred for 13 hours. The reaction solution was added to ice water (5 mL), stirred for 15 minutes, and extracted with ethyl acetate (10 mL*2). The combined organic phase was washed with saturated brine (10 mL*2), dried over anhydrous sodium sulfate, filtered and the filtrate was concentrated. The obtained residue was purified by preparative thin-layer chromatography silica-gel plate (petroleum ether/ethyl acetate=3/1) to obtain compound 6f. LCMS (ESI) m/z: 305.1 (M+1).

Step 6:

A solution of compound 6f (0.1 g, 328.50 μmol, 1 eq) and m-CPBA (146.72 mg, 722.71 μmol, 85% purity, 2.2 eq) in dichloromethane (5 mL) was stirred at 20° C. for 2 hours. The reaction mixture was quenched with 10% aqueous sodium sulfite (10 mL), and washed with saturated aqueous sodium bicarbonate (20 mL*5). The organic phase was concentrated, and the obtained residue was purified by preparative thin-layer chromatography silica-gel plate (petroleum ether/ethyl acetate=1/1) to obtain compound 6g. LCMS (ESI) m/z: 336.9 (M+1).

Step 7:

A solution of compound 6g (70 mg, 208.08 μmol, 1 eq), compound 1e (49.15 mg, 228.89 μmol, 1.1 eq, hydrochloride salt) and DIPEA (134.46 mg, 1.04 mmol, 181.22 μl, 5 eq) in DMSO (2 mL) was heated to 100° C. and stirred for 16 hours. LC-MS showed that about 62% starting material was remained and about 20% of product was synthesized. The reaction mixture was stirred at 100° C. for 3 hours. LC-MS showed that about 58% starting material was remained and about 22% of product was synthesized. The reaction mixture was filtered, and the filtrate was purified by preparative HPLC (column: Waters Xbridge 150*25 mm*5 μm; mobile phase A: water (containing 0.05% ammonia); mobile phase B: acetonitrile; gradient elution: 100%, 8 minutes) to obtain compound 6. LCMS (ESI) m/z: 435.2 (M+1); $^1$H NMR (400 MHz, $CD_3OD$) δ 8.88 (s, 1H), 6.67 (s, 1H), 4.60 (s, 2H), 4.19-4.05 (m, 2H), 3.77-3.67 (m, 2H), 3.11-2.97 (m, 2H), 2.89 (s, 3H), 2.41-2.28 (m, 4H), 2.23-2.12 (m, 2H), 2.03-1.66 (m, 7H), 1.16 (s, 3H).

Embodiment 7: Preparation of Compound 7 and Compound 8

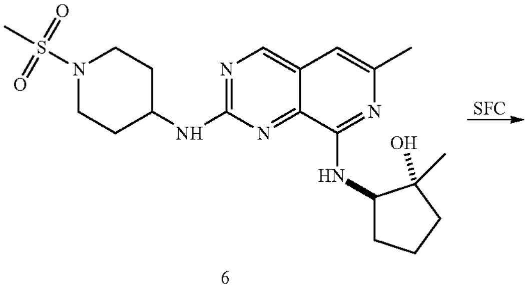

6

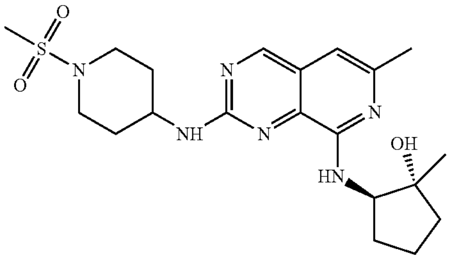

7 or 8

+

-continued

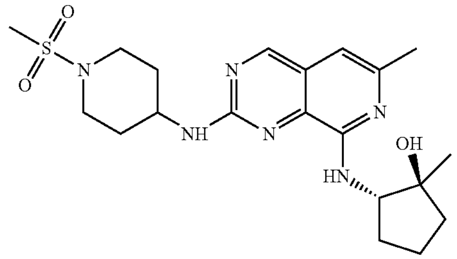

8 or 9

Compound 6 (80 mg, 173.14 μmol) was separated by Supercritical Fluid Chromatography (column: DAICEL CHIRALPAK AD-H (250 mm*30 mm, 5 μm); mobile phase A: carbon dioxide; mobile phase B: ethanol containing 0.1% ammonia; gradient elution: 30%-30%, 4 minutes) to obtain compound 7 (retention time: 1.706 minutes) and compound 8 (retention time: 1.831 minutes). The data was characterized as follows:

Compound 7 (retention time: 1.706 minutes): LCMS (ESI) m/z: 435.3 (M+1); $^1$H NMR (400 MHz, $CD_3OD$) δ 8.91 (s, 1H), 6.73 (s, 1H), 4.76-4.62 (m, 1H), 4.24-4.07 (m, 2H), 3.81-3.68 (m, 2H), 3.02 (br t, J=10.8 Hz, 2H), 2.89 (s, 3H), 2.43-2.29 (m, 4H), 2.16-2.15 (m, 2H), 2.00 (dt, J=7.6, 3.1 Hz, 1H), 1.95-1.79 (m, 4H), 1.76-1.64 (m, 2H), 1.19 (s, 3H);

Compound 8 (retention time: 1.831 minutes): LCMS (ESI) m/z: 435.3 (M+1); $^1$H NMR (400 MHz, $CD_3OD$) δ 8.91 (s, 1H), 6.73 (s, 1H), 4.69-4.62 (m, 1H), 4.16-4.10 (m, 2H), 3.76-3.73 (m, 2H), 3.05-3.03 (br t, J=10.4 Hz, 2H), 2.89 (s, 3H), 2.40-2.35 (m, 4H), 2.19-2.15 (m, 2H), 1.90 (m, 1H), 1.87-1.85 (m, 4H), 1.74-1.70 (m, 2H), 1.19 (s, 3H).

Embodiment 8: Preparation of Compound 9

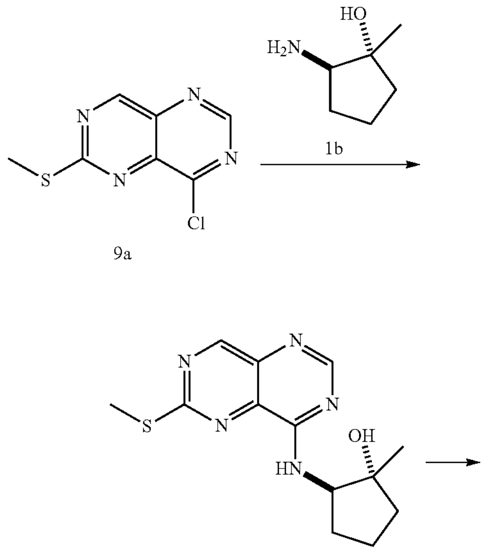

9a

9b

-continued

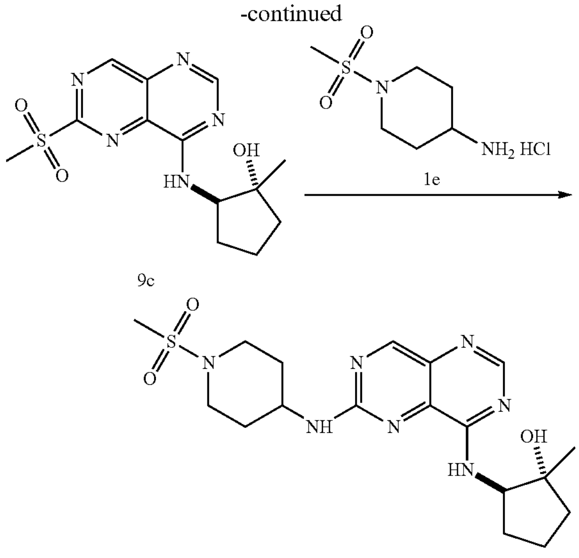

9c

9

Step 1:

A solution of compound 9a (500 mg, 2.35 mmol, 1 eq), compound 1b (297.87 mg, 2.59 mmol, 1.1 eq) and triethylamine (356.87 mg, 3.53 mmol, 490.89 μL, 1.5 eq) in acetonitrile (15 mL) was heated to 80° C. and stirred for 4 h. The reaction mixture was concentrated under reduced pressure. Water (50 mL) was added to the reaction solution, and the mixture was extracted with ethyl acetate (50 mL*2). The combined organic phase was washed with saturated brine (50 mL*2), dried over sodium sulfate, filtered and the filtrate was concentrated to obtain compound 9b. LCMS (ESI) m/z: 292.0 (M+1).

Step 2:

A solution of compound 9b (0.7 g, 2.40 mmol, 1 eq) and m-CPBA (1.22 g, 6.01 mmol, 85% purity, 2.5 eq) in dichloromethane (20 mL) was stirred at 20° C. for 2 hours. The reaction solution was added with saturated sodium sulfite solution (15 mL), stirred for 15 minutes and extracted with dichloromethane (20 mL*2). The combined organic phase was washed with saturated brine (20 mL*2), dried over anhydrous sodium sulfate, filtered and the filtrate was concentrated. The resulting crude product was purified by preparative thin-layer chromatography silica-gel plate (ethyl acetate) to obtain compound 9c. LCMS (ESI) m/z: 324.5 (M+1).

Step 3:

A solution of compound 9c (80 mg, 247.39 μmol, 1 eq), compound 1e (58.43 mg, 272.13 μmol, 1.1 eq, hydrochloride) and DIPEA (95.92 mg, 742.18 μmol, 129.27 μL, 3 eq) in DMSO (3 mL) was heated to 80° C. and stirred for 10 hours. The reaction solution was purified by preparative HPLC (column: Waters Xbridge 150*25 mm*5 μm; mobile phase A: 10 mmol/L ammonium bicarbonate aqueous solution; mobile phase B: acetonitrile; gradient elution: 11%-41%, 10 minutes) to obtain compound 9. $^1$H NMR (400 MHz, $CDCl_3$) δ 8.92 (s, 1H), 8.29 (s, 1H), 6.58 (br s, 1H), 6.08 (br s, 1H), 5.38 (br s, 1H), 4.92-4.54 (m, 1H), 4.15 (ddd, J=10.1, 8.5, 4.8 Hz, 1H), 4.07-3.92 (m, 1H), 3.72 (br d, J=11.6 Hz, 2H), 2.99-2.85 (m, 2H), 2.77 (s, 3H), 2.36-2.22 (m, 1H), 2.14 (br dd, J=12.9, 2.8 Hz, 2H), 2.03-1.92 (m, 1H), 1.90-1.77 (m, 3H), 1.70-1.55 (m, 2H), 1.08 (s, 3H). LCMS (ESI) m/z: 422.3 (M+1).

Embodiment 9: Preparation of Compound 10

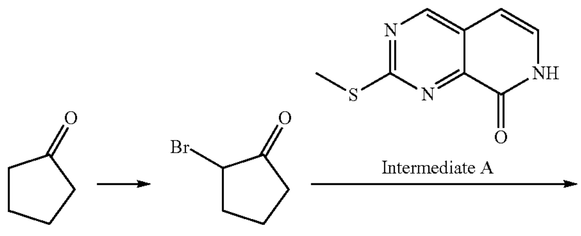

10a 10b

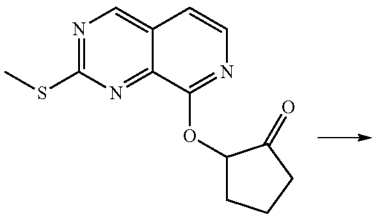

10c

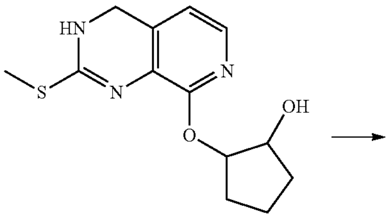

10d

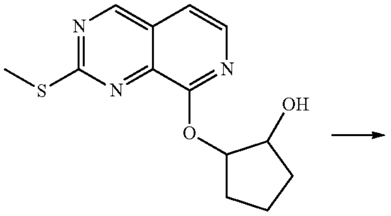

10e

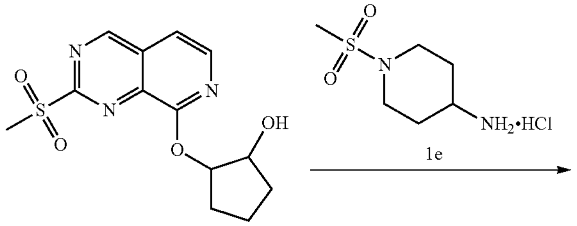

10f

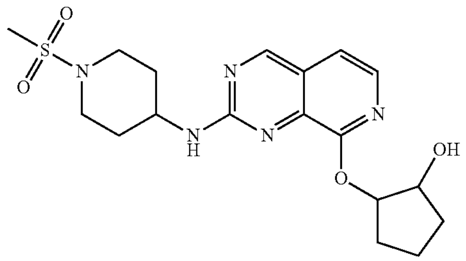

10

Step 1:

Compound 10a (5 g, 59.44 mmol, 5.26 mL, 1 eq), NBS (10.58 g, 59.44 mmol, 1 eq) and p-TSA (1.02 g, 5.94 mmol, 0.1 eq) were added to acetonitrile (50 mL) solution and stirred at 25° C. for 16 hours. The reaction solution was concentrated under reduced pressure, and the obtained residue was purified by silica gel column chromatography (petroleum ether/ethyl acetate=30/1) to obtain compound 10b. $^1$H NMR (400 MHz, $CDCl_3$) δ 4.17 (dd, J=6.2, 4.7 Hz, 1H), 2.41-2.25 (m, 2H), 2.23-2.07 (m, 3H), 2.03-1.86 (m, 1H).

Step 2:

Compound 10b (1 g, 5.18 mmol, 1 eq), intermediate A (2.53 g, 15.53 mmol, 3 eq), and potassium carbonate (1.43 g, 10.35 mmol, 2 eq) were added to DMF (10 mL), the resulting reaction solution was stirred at 20° C. for 16 hours. Ethyl acetate (50 mL) and water (50 mL) were added to the reaction solution, and the mixture was poured into a separatory funnel for liquid separation. The aqueous phase was extracted with ethyl acetate (50 mL*2). The obtained organic phase was washed with sodium brine (50 mL*2), dried over anhydrous sodium sulfate, filtered and the filtrate was concentrated. The obtained residue was purified by column chromatography (petroleum ether/ethyl acetate=5/1) to obtain compound 10c. LCMS (ESI) m/z: 276.2 (M+1); $^1$H NMR (400 MHz, $CDCl_3$) δ 9.06 (s, 1H), 7.94 (d, J=5.6 Hz, 1H), 7.15 (d, J=5.6 Hz, 1H), 5.63 (dd, J=10.5, 8.6 Hz, 1H), 2.63 (s, 3H), 2.61-2.52 (m, 1H), 2.45-2.31 (m, 2H), 2.24-2.11 (m, 2H), 2.00-1.85 (m, 1H).

Step 3:

Sodium borohydride (82.44 mg, 2.18 mmol, 1.5 eq) was added to a solution of compound 10c (0.4 g, 1.45 mmol, 1 eq) in methanol (10 mL) at 0° C. under nitrogen atmosphere, and the reaction solution was reacted for 0.5 hours. The reaction was quenched with saturated aqueous ammonium chloride (5 mL) and concentrated under reduced pressure. Water (10 mL) was added to the obtained residue, and the mixture was extract with ethyl acetate (10 mL*4). The combined organic phase was washed with saturated brine (20 mL*2), dried over anhydrous sodium sulfate, filtered and the filtrate was concentrated to obtain compound 10d.

Step 4:

A solution of compound 10d (300 mg, 1.07 mmol, 1 eq) and activated manganese dioxide (933.61 mg, 10.74 mmol, 10 eq) in dichloromethane (10 mL) was heated to 40° C. and stirred for 1 hour. The reaction solution was filtered, and the filtrate was concentrated under reduced pressure. The resulting residue was purified by preparative thin layer chromatography silica-gel plate (ethyl acetate) to obtain compound 10e.

Step 5:

A solution of compound 10e (0.25 g, 901.42 μmol, 1 eq) and m-CPBA (427.77 mg, 1.98 mmol, purity: 80%, 2.2 eq) in dichloromethane (10 mL) was stirred at 25° C. for 1 h. LCMS showed that the starting material was reacted completely, and the target product was synthesized. The reaction solution was washed with 10% aqueous sodium sulfite (10 mL) and saturated aqueous sodium bicarbonate (10 mL) successively, and the organic phase was concentrated under reduced pressure. The resulting residue was purified by preparative thin layer chromatography silica-gel plate (ethyl acetate) to obtain compound 10f. LCMS (ESI) m/z: 310.1 (M+1).

Step 6:

A solution of compound 10f (15 mg, 48.49 μmol, 1 eq), compound 1e (15.62 mg, 72.74 μmol, 1.5 eq, hydrochloride salt) and DIPEA (31.34 mg, 242.45 μmol, 42.23 μL, 5 eq) in DMSO (1 mL) was heated to 100° C. and stirred for 14 h. The reaction solution was filtered, and the filtrate was purified by preparative HPLC (column: Waters Xbridge 150*25 mm*5 μm; mobile phase A: 10 mmol/L ammonium bicarbonate aqueous solution; mobile phase B: acetonitrile; gradient elution: 15%-45%, 10 min) to obtain compound 10. LCMS (ESI) m/z: 408.3 (M+1); $^{1}H$ NMR (400 MHz, $CDCl_3$) δ 9.01 (s, 1H), 7.87 (d, J=5.5 Hz, 1H), 7.13 (d, J=5.6 Hz, 1H), 5.41-5.33 (m, 1H), 4.37 (q, J=4.9 Hz, 1H), 4.24-4.06 (m, 1H), 3.82 (br d, J=12.0 Hz, 2H), 2.98 (br t, J=10.6 Hz, 2H), 2.85 (s, 3H), 2.37-2.20 (m, 3H), 2.07-1.88 (m, 5H), 1.74-1.66 (m, 4H).

Embodiment 10: Preparation of Compound 11

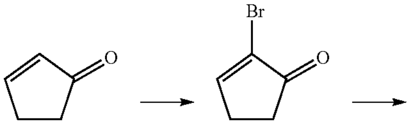

11a 11b

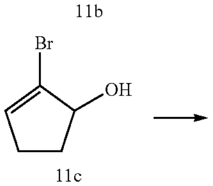

11c

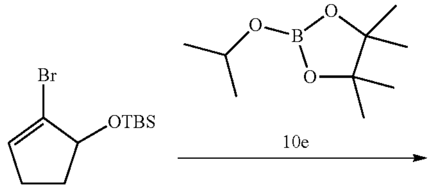

10e

11d

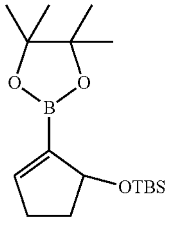

11f

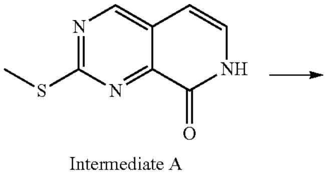

Intermediate A

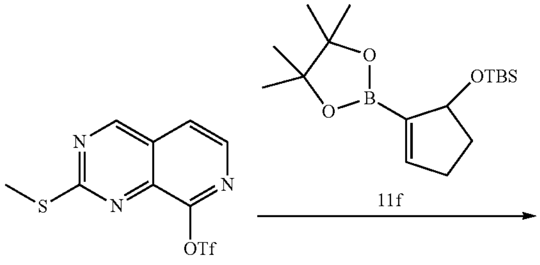

11f

11g

-continued

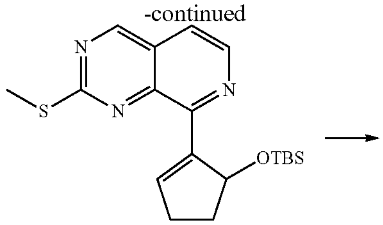

11h

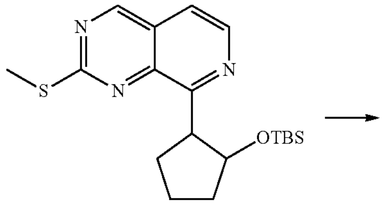

11i

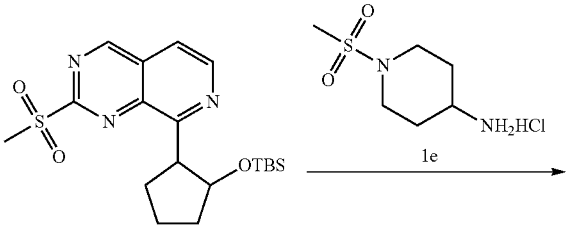

1e

11j

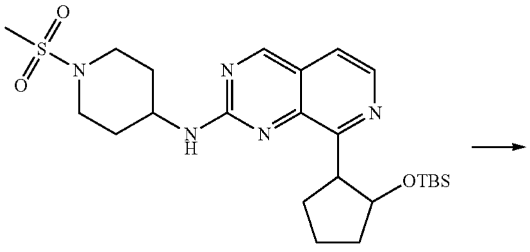

11k

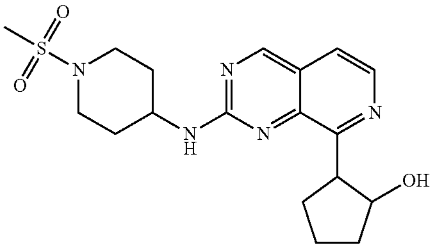

11

Step 1:

Pyridine nitrogen oxide (20.85 g, 219.24 mmol, 1.2 eq) was added to a solution of compound 11a (15 g, 182.70 mmol, 15.31 mL, 1 eq) in acetonitrile (200 mL), and the resulting reaction solution was cooled to 0° C., NBS (34.14 g, 191.84 mmol, 1.05 eq) was added in portions, and the resulting reaction solution was stirred at 25° C. for 16 hours. 10% aqueous sodium sulfite (50 mL) was added to the above reaction solution, and the resulting mixture was concentrated under reduced pressure to remove acetonitrile. The aqueous phase was extracted with ethyl acetate (300 mL*2), the combined organic phase was dried over anhydrous sodium sulfate, filtered and the filtrate was concentrated. The obtained residue was purified by silica gel column chromatography (petroleum ether/ethyl acetate=20/1) to obtain compound 11b. $^1$H NMR (400 MHz, $CDCl_3$) δ 7.83-7.75 (m, 1H), 2.75-2.67 (m, 2H), 2.58-2.48 (m, 2H).

Step 2:

Cerium trichloride (33.68 g, 136.65 mmol, 8.59 mL, 1.1 eq) was added to a solution of compound 11b (20 g, 124.23 mmol, 1 eq)) in the methanol (200 mL), the reaction solution was cooled to 0° C., sodium borohydride (5.64 g, 149.07 mmol, 1.2 eq) was added in portions. The reaction solution was stirred at 25° C. for 16 hours. Saturated aqueous ammonium chloride (100 mL) was added to the above reaction solution, and the resulting mixture was concentrated under reduced pressure to remove methanol. The aqueous phase was extracted with ethyl acetate (200 mL), the organic phase was washed with water (50 mL) after separation, dried over anhydrous sodium sulfate, filtered and the filtrate was concentrated. The obtained residue was purified by column chromatography (petroleum ether:ethyl acetate=20:1) to obtain compound 11c. $^1$H NMR (400 MHz, $CDCl_3$) δ 6.20-5.98 (m, 1H), 4.80-4.67 (m, 1H), 2.50-2.28 (m, 3H), 1.98-1.81 (m, 1H).

Step 3:

A solution of compound 11c (14.3 g, 87.72 mmol, 1 eq) in dichloromethane (150 mL) was cooled to 0° C. Imidazole (11.94 g, 175.45 mmol, 2 eq) was added, then TBSCl (13.22 g, 87.72 mmol, 10.75 mL, 1 eq) was added in portions. The resulting reaction solution was stirred at 25° C. for 16 hours. The reaction solution was washed with water (100 mL), the organic phase was dried over anhydrous sodium sulfate, filtered and the filtrate was concentrated. The obtained residue was purified by column chromatography (petroleum ether) to obtain compound 11d. $^1$H NMR (400 MHz, $CDCl_3$) δ 5.98-5.77 (m, 1H), 4.67-4.49 (m, 1H), 2.35-2.25 (m, 1H), 2.21-2.02 (m, 2H), 1.75-1.63 (m, 1H), 0.83-0.77 (s, 9H), 0.05-0.05 (m, 6H).

Step 4:

A solution of compound 11d (7.5 g, 27.05 mmol, 1 eq) in tetrahydrofuran (50 mL) was cooled to −78° C. and butyllithium (2.5 mol/L, 14.07 mL, 1.3 eq) was added dropwise and stirred at −78° C. for 30 minutes. 11e (5.54 g, 29.75 mmol, 6.07 mL, 1.1 eq) was added dropwise to the above reaction solution, and the resulting mixture was stirred at −78° C. for 30 minutes. The reaction solution was quenched with ammonium chloride (2 mol/L, 20 mL), the aqueous phase was extracted with ethyl acetate (100 mL), and the organic phase was concentrated. The obtained residue was purified by column chromatography (petroleum ether/ethyl acetate=100/1) to obtain compound 11f. $^1$H NMR (400 MHz, $CDCl_3$) δ 6.56-6.48 (m, 1H), 4.97-4.82 (m, 1H), 2.45 (m, 1H), 2.24-1.96 (m, 2H), 1.66-1.47 (m, 1H), 1.16-1.14 (m, 12H), 0.80-0.77 (m, 9H), 0.01-0.01 (m, 6H).

Step 5:

A solution of compound 1 (2.0 g, 10.35 mmol, 1 eq) in tetrahydrofuran (20 mL) was cooled to 0° C., sodium hydride (827.97 mg, 20.70 mmol, purity: 60%, 2 eq) was added in portions, the mixture was stirred at 0° C. for 30 minutes, then bis(trifluoromethanesulfonyl)aniline (4.44 g, 12.42 mmol, 1.2 eq) was added in portions, and then the mixture was stirred at 0-25° C. for 1.5 hours. The reaction was quenched with 10% aqueous ammonium chloride solution (20 mL), extracted with ethyl acetate (100 mL), washed with water (30 mL), and the organic phase was dried over anhydrous sodium sulfate, filtered and concentrated to obtain the crude product, and then purified by silica gel column chromatography (petroleum ether:ethyl acetate=20/1-10/1) to obtain compound 11f. LCMS (ESI) m/z: 326.2 (M+1).

Step 6:

A solution of $Pd(dppf)Cl_2$ (224.94 mg, 307.42 μmol, 0.1 eq) and potassium phosphate (1.96 g, 9.22 mmol, 3 eq) in water (2 mL) was added to a solution of compound 11f (1.10 g, 3.38 mmol, 1.1 eq) and compound 11g (1.0 g, 3.07 mmol, 1 eq) in 1,4-dioxane (20 mL) under nitrogen protection, and the resulting mixture was heated to 90° C. and stirred for 16 hours. The reaction solution was concentrated, and the resulting residue was diluted with ethyl acetate (50 mL), washed with water (20 mL), and the organic phase was concentrated. The obtained residue was purified by column chromatography (petroleum ether/ethyl acetate=10/1) to obtain compound 11h. LCMS (ESI) m/z: 374.3 (M+1).

Step 7:

$Rh(PPh_3)_3Cl$ (100.15 mg, 108.25 μmol, 1 eq) was added to a solution of compound 11h (50 mg, 108.25 μmol, 1 eq) in ethanol (10 mL), and heat to 80° C. under 15 PSI hydrogen pressure, and the mixture was stirred for 1 hour. Then the reaction solution was concentrated, the obtained residue was purified by column chromatography (petroleum ether/ethyl acetate=20/1) to obtain compound 11i. LCMS (ESI) m/z: 376.4 (M+1); $^1$H NMR (400 MHz, $CDCl_3$) δ 9.26-9.08 (m, 1H), 8.62 (d, J=5.40 Hz, 1H), 7.48 (d, J=5.52 Hz, 1H), 4.75-4.67 (m, 1H), 4.60-4.49 (m, 1H), 2.77-2.73 (m, 3H), 2.35-2.25 (m, 1H), 2.20-2.08 (m, 1H), 2.02-1.82 (m, 4H), 0.75-0.65 (m, 9H), 0.42-0.33 (m, 3H), −0.13-−0.19 (m, 3H).

Step 8:

m-CPBA (103.37 mg, 479.23 μmol, purity: 80%, 1.8 eq) was added to a solution of compound 11i (100 mg, 266.24 μmol, 1 eq) in dichloromethane (5 mL), and the resulting reaction solution was stirred at 25° C. for 5 h. The reaction solution was quenched with saturated aqueous sodium sulfite (10 mL), the aqueous phase was extracted with dichloromethane (20 mL), the organic phase was dried over anhydrous sodium sulfate, filtered and the filtrate was concentrated. The obtained residue was purified by column chromatography (petroleum ether/ethyl acetate=1/1) to obtain compound 11j. LCMS (ESI) m/z: 408.4 (M+1).

Step 9:

DIPEA (95.12 mg, 736.01 μmol, 128.20 μL, 3 eq) and compound 1e (79.02 mg, 368.01 μmol, 1.5 eq, hydrochloride salt) was added to a solution of compound 11j (100 mg, 245.34 μmol, 1 eq) in DMSO (1 mL), and the resulting reaction solution was stirred at 100° C. for 1 h. The reaction solution was diluted with ethyl acetate (20 mL), washed with water (5 mL*3), and the organic phase was concentrated. The obtained residue was purified by silica gel column chromatography (petroleum ether:ethyl acetate=1:1) to obtain compound 11k. LCMS (ESI) m/z: 506.5 (M+1).

Step 10:

Hydrochloric acid (1.0 mol/L, 1 mL, 6.32 eq) was added to a solution of compound 11k (80 mg, 158.18 μmol, 1 eq) in THF (1 mL), and the reaction solution was stirred at 25° C. for 30 minutes. 10% aqueous sodium bicarbonate solution (5 mL) was added to the reaction solution, and then the mixture was extracted with ethyl acetate (20 mL). The organic phase was dried over anhydrous sodium sulfate, filtered and the filtrate was concentrated. The obtained residue was purified by preparative HPLC (column: Waters Xbridge 150*25 mm*5 μm; mobile phase A: water (containing 0.05% ammonia); mobile phase B: acetonitrile; gradient elution: 17%-45%, 10 minutes) to obtain compound 11. LCMS (ESI) m/z: 392.3; $^1$H NMR (400 MHz, $CDCl_3$) δ 9.08 (s, 1H), 8.38 (d, J=5.40 Hz, 1H), 7.38 (d, J=5.40 Hz, 1H), 5.66-5.41 (m, 1H), 4.97-4.77 (m, 1H), 4.43-4.30 (m, 1H), 4.07-3.81 (m, 4H), 3.05-2.95 (m, 2H), 2.86 (s, 3H), 2.53-2.33 (m, 2H), 2.17 (s, 3H), 1.86 (br s, 3H), 1.79-1.67 (m, 2H).

Embodiment 11: Preparation of Compound 12 and Compound 13

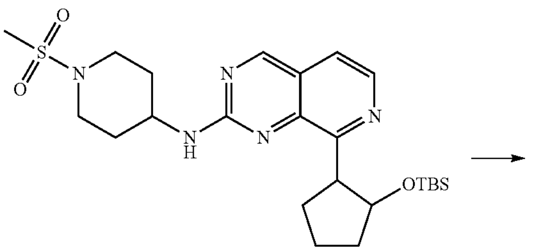

11k

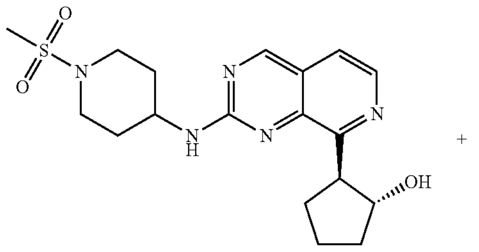

12 or 13

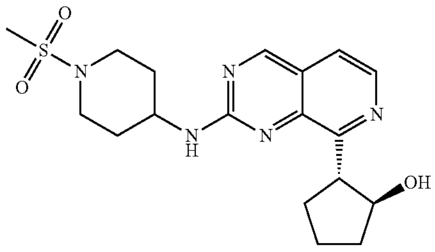

13 or 12

Hydrochloric acid solution (1.0 mol/L, 19.64 mL, 4.05 eq) was added to a solution of compound 11k (2.5 g, 4.85 mmol, 1 eq) in tetrahydrofuran (20 mL), and the resulting reaction solution was stirred at 25° C. for 0.5 h. The reaction solution was quenched with 10% aqueous sodium bicarbonate solution (50 mL), and extracted with ethyl acetate (200 mL), the organic phase was dried over anhydrous sodium sulfate, filtered and the filtrate was concentrated. The obtained crude product was purified by silica gel column chromatography (ethyl acetate), the obtained racemate was separated and purified by Supercritical Fluid Chromatography (column: Chiralpak IG-3 50×4.6 mm I.D., 3 μm; mobile phase A: carbon dioxide, mobile phase B: methanol containing 0.05% diethylamine; gradient elution: mobile phase B/mobile phase A=40%; flow rate: 3 mL/min; detector: PDA; column temperature: 35° C.; pressure: 100 Bar) to obtain compound 12 (retention time: 1.598 minutes) and compound 13 (retention time: 2.130 minutes). The data was characterized as follows:

Compound 12 (retention time: 1.598 minutes): LCMS (ESI) m/z: 392.4; $^1$H NMR (400 MHz, $CDCl_3$) δ 9.06-8.92 (m, 1H), 8.29 (d, J=5.4 Hz, 1H), 7.29 (d, J=5.4 Hz, 1H), 5.52-5.31 (m, 1H), 4.84-4.64 (m, 1H), 4.29-4.21 (m, 1H), 4.03-3.68 (m, 4H), 3.00-2.84 (m, 2H), 2.80-2.72 (m, 3H), 2.40-2.19 (m, 2H), 2.17-1.99 (m, 3H), 1.96-1.71 (m, 3H), 1.69-1.58 (m, 2H).

Compound 13 (retention time: 2.130 minutes): LCMS (ESI) m/z: 392.3; $^1$H NMR (400 MHz, $CDCl_3$) δ 9.18-9.00 (m, 1H), 8.38 (d, J=5.4 Hz, 1H), 7.39 (d, J=5.4 Hz, 1H), 5.71-5.36 (m, 1H), 4.40-4.29 (m, 1H), 4.12-3.80 (m, 4H), 3.06-2.93 (m, 2H), 2.89-2.80 (m, 3H), 2.50-2.34 (m, 2H), 2.29-2.10 (m, 3H), 2.07-1.82 (m, 3H), 1.79-1.68 (m, 2H).

Embodiment 12: Preparation of Compound 14

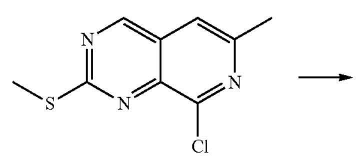

6e

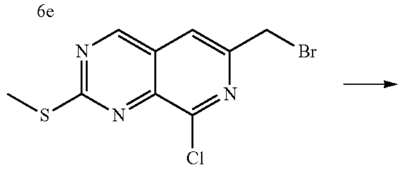

14a

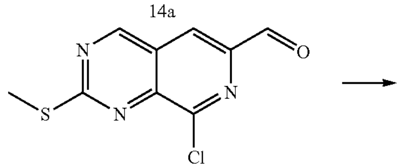

14b

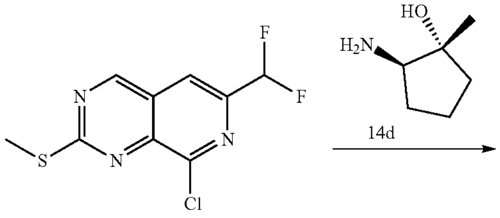

14c

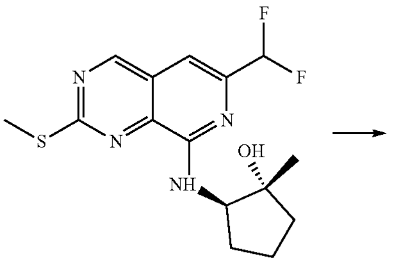

14e

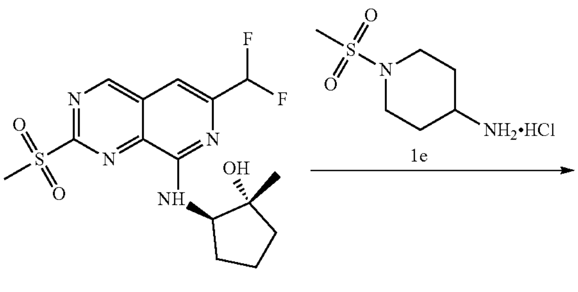

14f

-continued

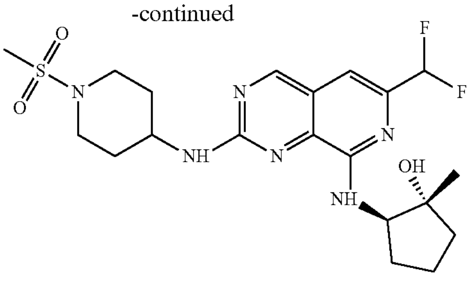

14

Step 1:

Under nitrogen protection, a solution of compound 6e (875.83 mg, 3.88 mmol, 1 eq), NBS (2.07 g, 11.64 mmol, 3 eq) and AIBN (63.72 mg, 388.05 μmol, 0.1 eq) in carbon tetrachloride (10 mL) was heated to 75° C. and stirred for 15 hours. The reaction solution was concentrated, and the obtained residue was purified by silica gel column chromatography (petroleum ether/ethyl acetate=30/1) to obtain compound 14a. LCMS (ESI) m/z: 306.0 (M+1); $^1$H NMR (400 MHz, $CDCl_3$) δ 9.22 (s, 1H), 7.75 (s, 1H), 4.68 (s, 2H), 2.78-2.76 (m, 3H).

Step 2:

NMO (215.37 mg, 1.84 mmol, 194.03 μL, 2 eq) was added to a solution of compound 14a (280 mg, 919.26 μmol, 1 eq) in acetonitrile (10 mL), and the resulting reaction solution was stirred at 25° C. for 2 hours. Sodium sulfite (0.5 g) was added to the above reaction solution, and stirred at 25° C. for 30 minutes. The reaction solution was filtered, the filtrate was concentrated under reduced pressure, and the obtained residue was purified by preparative thin-layer chromatography silica-gel plate (petroleum ether/ethyl acetate=4/1) to obtain compound 14b. $^1$H NMR (400 MHz, $CDCl_3$) δ 10.06 (s, 1H), 9.28 (s, 1H), 8.23 (s, 1H), 2.71 (s, 3H). LCMS (ESI) m/z: 240.1 (M+1).

Step 3:

At 0° C. and under the protection of nitrogen, DAST (73.98 mg, 458.94 μmol, 60.64 μL, 2.2 eq) was added dropwise slowly to a solution of compound 14b (50 mg, 208.61 μmol, 1 eq) in dichloromethane (1 mL), and the resulting reaction solution was stirred at 25° C. for 1 h. The reaction solution was directly purified by preparative thin-layer chromatography silica-gel plate (petroleum ether/ethyl acetate=5/1) to obtain compound 14c. LCMS (ESI) m/z: 208.1 (M+1). $^1$H NMR (400 MHz, $CDCl_3$) δ 9.22 (s, 1H), 7.89 (s, 1H), 6.84-6.49 (m, 1H), 2.69 (s, 3H).

Step 4:

A solution of compound 14c (10 mg, 38.21 μmol, 1 eq), compound 14d (5.28 mg, 45.86 μmol, 1.2 eq) and DIPEA (9.88 mg, 76.43 μmol, 13.31 μL, 2 eq) in acetonitrile (1 mL) was stirred at 80° C. for 16 h. The reaction solution was concentrated, and water (5 mL) and ethyl acetate (5 mL) were added to the residue obtained, and the aqueous phase was extracted with ethyl acetate (5 mL*2) after separation. The combined organic phase was washed with saturated brine (10 mL*2), dried over anhydrous sodium sulfate, filtered and the filtrate was concentrated to obtain compound 14e. LCMS (ESI) m/z: 341.1 (M+1).

Step 5:

m-CPBA (20.91 mg, 96.95 μmol, purity: 80%, 2.2 eq) was added to a solution of compound 14e (15 mg, 44.07 μmol, 1 eq) in dichloromethane (3 mL) and stirred at 25° C. for 2 hours. The reaction solution was washed with 10% aqueous sodium sulfite (5 mL) and saturated aqueous sodium bicarbonate (5 mL*2) successively. The organic phase was concentrated under reduced pressure to obtain compound 14f. LCMS (ESI) m/z: 373.1 (M+1).

Step 6:

A solution of compound 14f (13 mg, 34.91 μmol, 1 eq), compound 1e (8.99 mg, 41.89 μmol, 1.2 eq, hydrochloride salt) and DIPEA (13.54 mg, 104.73 μmol, 18.24 μl, 3 eq) in DMSO (1 mL) was stirred at 100° C. for 4 hours. The reaction solution was filtered, and the filtrate was purified by preparative HPLC (column: Waters Xbridge 150*25 mm*5 μm; mobile phase A: water containing 0.05% ammonia; mobile phase B: acetonitrile; gradient elution: 28%-58%, 7 minutes) to obtain compound 14. LCMS (ESI) m/z: 471.3 (M+1); $^1$H NMR (400 MHz, $CD_3OD$) δ 9.01 (s, 1H), 7.11 (s, 1H), 6.79-6.38 (m, 1H), 4.25 (t, J=8.6 Hz, 1H), 4.21-4.11 (m, 1H), 3.79-3.72 (m, 2H), 3.08-2.99 (m, 2H), 2.90 (s, 3H), 2.44-2.29 (m, 1H), 2.22-2.12 (m, 2H), 2.04-1.93 (m, 1H), 1.90-1.67 (m, 6H), 1.37-1.27 (m, 1H), 1.19 (s, 3H).

Embodiment 13: Preparation of Compound 15

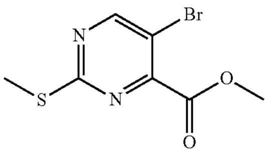

A1

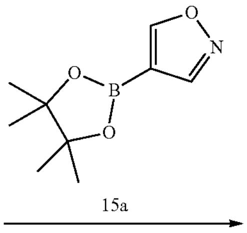

15a

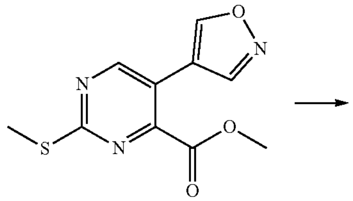

15b

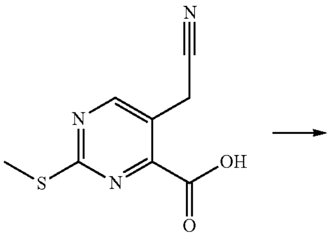

15c

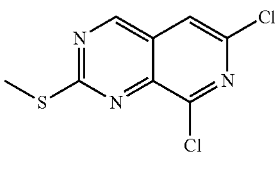

15d

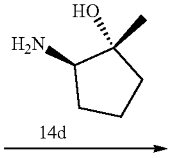

14d

-continued

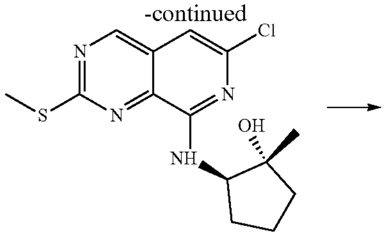

15e

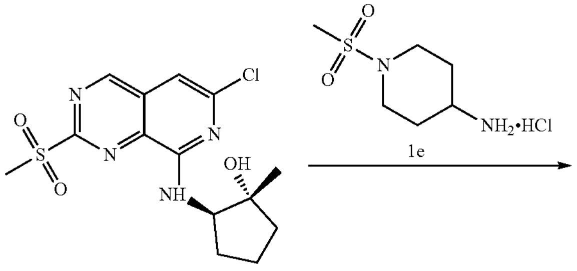

1e

15f

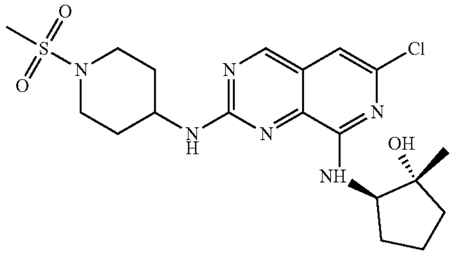

15

Sodium carbonate (8.06 g, 76.01 mmol, 2 eq) was added to a solution of compound A1 (10 g, 38.01 mmol, 1 eq) and compound 15a (8.89 g, 45.61 mmol, 1.2 eq) in tetrahydrofuran (100 mL) and water (100 mL), then the reaction solution was replaced with nitrogen, and $(t\text{-}Bu_3P)_2PdCl_2$ (971.17 mg, 1.90 mmol, 0.05 eq) was added, the resulting reaction solution was heated to 65° C. and stirred for 16 hours. The reaction solution was diluted with ethyl acetate (200 mL) and water (100 mL) respectively, and the organic phase was separated and concentrated. The obtained crude product was purified by silica gel column chromatography (petroleum ether/ethyl acetate=10/1) to obtain compound 15b. LCMS (ESI) m/z: 252.0 (M+1).

Step 2:

A solution of compound 15b (6 g, 23.88 mmol, 1 eq), potassium carbonate (3.30 g, 23.88 mmol, 1 eq) and potassium fluoride (4.16 g, 71.60 mmol, 3 eq) in ethanol (30 mL) and water (30 mL) was heated to 80° C. and stirred for 16 hours. The mixture was concentrated to remove ethanol and then extracted with ethyl acetate (100 mL), the organic phase was discarded and the pH of the aqueous phase was adjusted to 1-2 with hydrochloric acid (10 mol/L), a solid was precipitated, filtered and the filter cake was dried to obtain compound 15c. LCMS (ESI) m/z: 210.0 (M+1).

Step 3:

A solution of compound 15c (1.0 g, 4.73 mmol, 1 eq) and phosphine pentachloride (1.08 g, 5.21 mmol, 1.1 eq) in $POCl_3$ (10 mL) was stirred at 20° C. for 2 h. The reaction solution was heated to 70° C. and stirred for 16 hours. Then the reaction solution was concentrated to remove $POCl_3$, the resulting residue was diluted with ethyl acetate (50 mL) and added slowly to 5% aqueous sodium carbonate solution (50 mL), and the insoluble black oil was filtered off. The obtained organic phase after separation was washed with saturated brine (10 mL), dried over anhydrous sodium sulfate, filtered and the filtrate was concentrated. The obtained crude product was purified by silica gel column chromatography (petroleum ether/ethyl acetate=10/1) to obtain compound 15d. LCMS (ESI) m/z: 245.9 (M+1); $^1H$ NMR (400 MHz, $CDCl_3$) δ 9.09 (s, 1H), 7.59 (s, 1H), 2.67 (s, 3H).

Step 4:

Compound 14d (350.97 mg, 3.05 mmol, 1.5 eq) and DIPEA (525.13 mg, 4.06 mmol, 707.72 μL, 2 eq) were added to a solution of compound 15d (500 mg, 2.03 mmol, 1 eq) in acetonitrile (10 mL), the resulting reaction solution was heated to 80° C. and stirred for 16 hours. The reaction solution was concentrated, and the obtained crude product was purified by silica gel column chromatography (petroleum ether/ethyl acetate=3/1) to obtain compound 15e. LCMS (ESI) m/z: 325.2 (M+1); $^1H$ NMR (400 MHz, DMSO-$d_6$) δ 9.29 (s, 1H), 7.19-7.11 (m, 1H), 7.04 (s, 1H), 4.84 (s, 1H), 4.38-4.23 (m, 1H), 2.66 (s, 3H), 2.29-2.13 (m, 1H), 1.85-1.56 (m, 5H), 1.19 (s, 3H).

Step 5:

m-CPBA (265.63 mg, 1.23 mmol, purity: 80%, 2 eq) was added to a solution of compound 15e (200 mg, 615.71 μmol, 1 eq) in dichloromethane (5 mL), and the reaction solution was heated at 25° C. and stirred for 0.5 hours. The reaction solution was quenched with saturated aqueous sodium sulfite (10 mL), then extracted with dichloromethane (20 mL), the organic phase was washed with saturated aqueous sodium bicarbonate (10 mL), dried over anhydrous sodium sulfate, filtered and the filtrate was concentrated to obtain compound 15f. LCMS (ESI) m/z: 357.2 (M+1).

Step 6:

DIPEA (304.25 mg, 2.35 mmol, 410.04 μL, 4 eq) was added to a solution of compound 15f (210 mg, 588.52 mmol, 1 eq) and compound 1e (314.72 mg, 1.47 mmol, 2.49 eq, hydrochloride salt) in DMSO (3 mL), and the resulting reaction solution was heated to 110° C. and stirred for 4 h. The reaction solution was diluted with ethyl acetate (20 mL) and then washed with water (10 mL) and saturated brine (10 mL) successively. The organic phase was dried over anhydrous sodium sulfate and filtered, and the filtrate was concentrated. The obtained crude product was purified by the prepared HPLC (column: Waters Xbridge 150*25 mm*5 μm; mobile phase A: water containing 0.05% ammonia; mobile phase B: acetonitrile; gradient elution: 32%-62%, 10 min) to obtain compound 15. LCMS (ESI) m/z: 453.4 (M+1); $^1H$ NMR (400 MHz, DMSO-4) δ 9.13-8.87 (m, 1H), 7.99-7.60 (m, 1H), 6.98-6.81 (m, 1H), 6.74-6.62 (m, 1H), 5.02-4.82 (m, 1H), 4.30-4.14 (m, 1H), 4.06-3.93 (m, 1H), 3.69-3.54 (m, 2H), 3.00-2.85 (m, 5H), 2.32-2.16 (m, 1H), 2.14-1.96 (m, 2H), 1.86-1.41 (m, 7H), 1.25-1.12 (m, 3H).

Embodiment 14: Preparation of Compound 16 and Compound 17

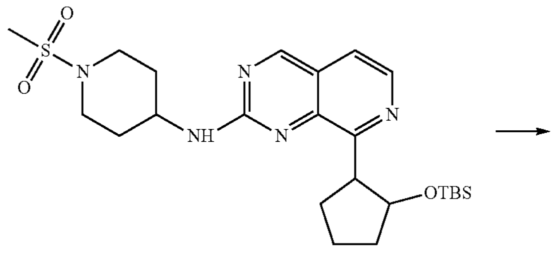

11k

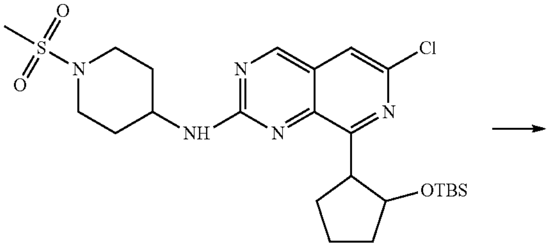

16a

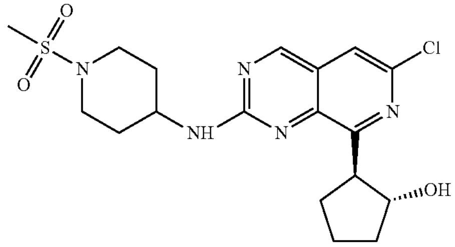

16 or 17

+

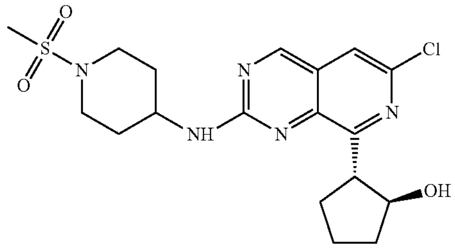

17 or 16

Step 1:

N-chlorosuccinimide (1.01 g, 7.59 mmol, 1.2 eq) was added to a solution of compound 11k (3.2 g, 6.33 mmol, 1 eq) in 30 mL of acetonitrile. The reaction solution was heated to 60° C. and reacted for 12 hours. After cooling down to room temperature, the reaction solution was quenched with 10 mL of saturated aqueous sodium sulfite solution, and the aqueous phase was extracted with dichloromethane (10 mL*3). The combined organic phase was washed twice with 10 mL of saturated brine and dried over anhydrous sodium sulfate. After filtration and concentration, the crude product 16a was obtained. MS [ESI, M+1]: 540.2.

Step 2:

Hydrochloric acid solution (1 mol/L, 40 mL, 5.40 eq) was added to a solution of compound 16a (4 g, 7.40 mmol, 1 eq) in tetrahydrofuran (40 mL), and the resulting mixture was stirred at 25° C. for 1 hour. The pH of the reaction solution was adjusted to 7 with saturated aqueous sodium bicarbonate solution, then the reaction solution was extracted three times with 50 mL of ethyl acetate, the combined organic phase was washed twice with 50 mL of saturated brine, dried over anhydrous sodium sulfate, filtered and the filtrate was concentrated. The obtained crude product was purified by HPLC (column: Phenomenex luna C18 (250*70 mm, 15 μm); mobile phase: [water (0.225% formic acid)-acetonitrile]; gradient elution 30%-60%, 20 minutes), the obtained racemate was separated and purified by Supercritical Fluid Chromatography (column: DAICEL CHIRALPAK AD (250 mm*30 mm, 10 um); mobile phase A: carbon dioxide, mobile phase B: methanol containing 0.1% ammonia; gradient elution: mobile phase B/mobile phase A=70%; flow rate: 3 mL/min; detector: PDA; column temperature: 35° C.; pressure: 100 Bar) to obtain compound 16 (retention time: 0.990 minutes) and compound 17 (retention time: 2.487 minutes).

The data was characterized as follows:

Compound 16 (retention time: 0.990 minutes): LCMS (ESI) m/z: 426.2; $^1$H NMR (400 MHz, $CD_3OD$) δ=9.05 (s, 1H), 7.56 (s, 1H), 4.71-4.60 (m, 1H), 4.21-4.05 (m, 2H), 3.80-3.72 (m, 2H), 3.09-2.98 (m, 2H), 2.92-2.87 (m, 3H), 2.29-2.18 (m, 3H), 2.18-2.08 (m, 1H), 2.03-1.84 (m, 3H), 1.83-1.63 (m, 3H).

Compound 17 (retention time: 2.487 minutes): LCMS (ESI) m/z: 426.2; $^1$H NMR (400 MHz, $CD_3OD$) δ=9.05 (s, 1H), 7.55 (s, 1H), 4.72-4.60 (m, 1H), 4.20-4.05 (m, 2H), 3.82-3.71 (m, 2H), 3.10-2.98 (m, 2H), 2.93-2.88 (m, 3H), 2.28-0.17 (m, 3H)$_{2.16}$-2.08 (m, 1H), 2.01-1.85 (m, 3H), 1.84-1.66 (m, 3H).

Embodiment 15: Preparation of Compound 18

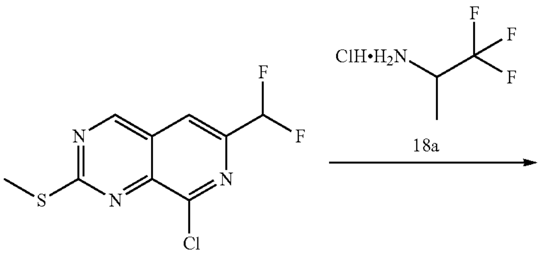

18a

14c

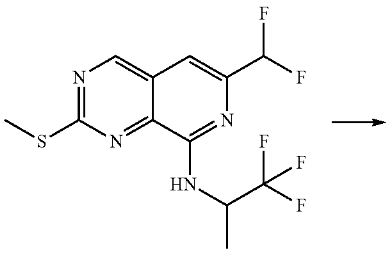

18b

-continued

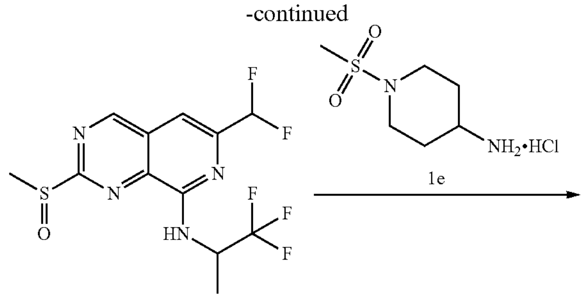

18c

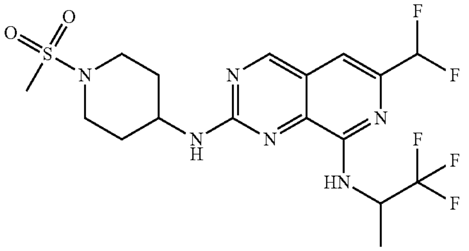

18

Step 1:

Compound 18a (1,1,1-trifluoroisopropylamine (1.30 g, 8.67 mmol, 82.20 μl, 2.27 eq, hydrochloride salt)), sodium tert-butoxide (1.10 g, 11.46 mmol, 76.43 μl, 3 eq), (±)-2,2-bis(diphenylphosphino)-1,1-binaphthyl (237.95 mg, 382.15 μmol, 0.1 eq) and bis(tri-tert-butylphosphine)palladium(0) (97.65 mg, 191.07 μmol, 0.05 eq) were added to a solution of compound 14c (1.0 g, 3.82 mmol, 1.0 eq) in ethylene glycol dimethyl ether (15 mL). The mixture was heated to 85° C. under nitrogen protection and reacted for 10 hours. The reaction was cooled to room temperature, added with water (50 mL), extracted with ethyl acetate (50 mL*2), the organic phase was combined, then washed with saturated brine (50 mL), dried over anhydrous sodium sulfate, filtered, and the filtrate was spin-dried to obtain the crude product. The crude compound was purified by chromatography column (100-200 mesh silica gel, petroleum ether/ethyl acetate=15/1, 3/1) to obtain compound 18b. $^1$H NMR (400 MHz, $CDCl_3$) δ=9.13 (s, 1H), 7.26 (s, 1H), 6.71-6.40 (m, 2H), 5.31-5.18 (m, 1H), 2.69 (s, 3H), 1.52 (d, J=7.0 Hz, 3H); LCMS (ESI) m/z: 338.8 $(m+1)^+$.

Step 2:

Peroxybenzoic acid (792.15 mg, 3.90 mmol, 85% purity, 1.2 eq) was added to a solution of compound 18b (1.1 g, 3.25 mmol, 1.0 eq) in dichloromethane (10 mL) at 0° C. The mixture was reacted at 0° C. for 1 hour. The reaction solvent was removed under reduced pressure to obtain compound 18c. LCMS (ESI) m/z: 354.9 $(m+1)^+$.

Step 3:

N, N-diisopropylethylamine (1.56 g, 12.11 mmol, 2.11 mL, 5 eq) and 4-amino-1-methylsulfonyl piperidine (1.04 g, 4.84 mmol, 2 eq, hydrochloride salt) were added to a solution of compound 18c in dimethyl sulfoxide (5 mL). The mixture was heated to 100° C. under nitrogen protection and reacted for 2 hours. The reaction solution was cooled to room temperature, added with water (20 mL), extracted with ethyl acetate (20 mL*2), the organic phases was combined, washed with saturated brine (20 mL), dried over anhydrous sodium sulfate, filtered, and the filtrate was spin-dried to obtain the crude product. The crude compound was purified by chromatography column (100-200 mesh silica gel, petroleum ether/ethyl acetate=10/1, 5/1) to obtain compound 18. $^1$H NMR (400 MHz, $CDCl_3$) δ=8.97 (s, 1H), 7.19 (s, 1H), 6.74-6.36 (m, 2H), 5.51-5.34 (m, 1H), 4.42-4.27 (m, 2H), 4.19-4.02 (m, 1H), 3.90-3.72 (m, 2H), 3.08-2.93 (m, 2H), 2.86 (s, 3H), 2.31-2.17 (m, 2H), 1.75 (d, J=9.8 Hz, 2H). LCMS (ESI) m/z: 468.9 $(m+1)^+$.

Embodiment 16: Preparation of Compound 19

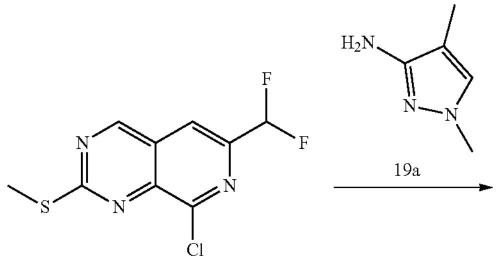

14c

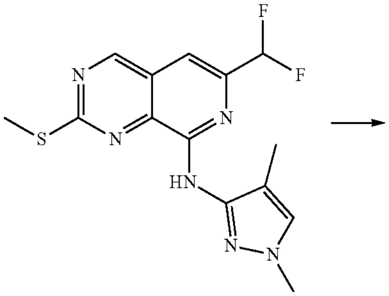

19b

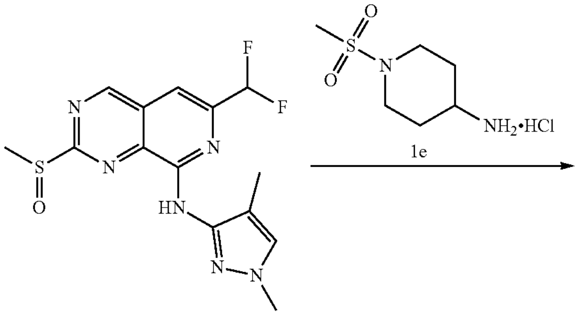

19c

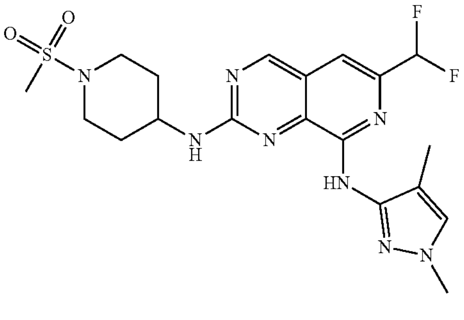

19

Step 1:

At 20-30° C., compound 19a (152.91 mg, 138 μmol, 3 eq) and diisopropylethylamine (177.80 mg, 138 μmol, 239.62 μL, 3 eq) were added successively to a solution of compound 14c (120 mg, 458.58 μmol, 1 eq) in dimethyl sulfoxide (4 mL), and the reaction solution was stirred at 100° C. for 12 hours under nitrogen protection. The reaction solution was quenched with water (15 mL), extracted twice with ethyl acetate (20 mL), the organic phase was washed with saturated brine (20 mL), dried over anhydrous sodium sulfate, and concentrated to obtain a residue. The residue was purified by column chromatography (developing agent: petroleum ether:ethyl acetate=1:0 to 1:1) to obtain compound 19b.

Step 2:

At 0° C., m-CPBA (50.46 mg, 248.54 μmol, 85% purity, 1.1 eq) was added in portions to a solution of compound 19b (76 mg, 225.95 μmol, 1 eq) in dichloromethane (2 mL), and the reaction solution was reacted for 1 hour under the protection of nitrogen. At 0-5° C., saturated Na2SO3 (10 mL) was added slowly to the reaction solution, and stirred at 15-25° C. for 0.5 hours, then the reaction solution was quenched, extract with dichloromethane (10 mL*2), the combined organic phase was dried over anhydrous Na2SO4, filtered and concentrated under reduced pressure to obtain the crude product of compound 19c.

Step 3:

At 20-30° C., compound 1e (97.50 mg, 454.08 μmol, 2 eq, hydrochloride salt) and diisopropylethylamine (117.37 mg, 908.16 μmol, 158.18 μL, 4 eq) were added successively to a solution of compound 19c (80 mg, 227.04 μmol, 1 eq) in dimethyl sulfoxide (3 mL), and the reaction solution was stirred at 100° C. under nitrogen protection for 6 hours. The reaction solution was diluted with water (10 mL), extracted with ethyl acetate (10 mL*2), the combined organic phase was washed with saturated brine (10 mL), dried over anhydrous sodium sulfate, filtered, and concentrated under reduced pressure to obtain a residue.

The residue was purified by preparative HPLC (column: YMC Triart 30*150 mm*7 μm; mobile phase: [water (hydrochloric acid)-acetonitrile]; 40%-60%, 9 minutes) and (column: Welch Ultimate XB—SiOH 250*50*10 μm; mobile phase: n-heptane-ethanol (0.1% ammonia); 15%-55%, 15 minutes) to obtain compound 19. LCMS (ESI) m/z: 467.1 $(M+1)^+$, H NMR (400 MHz, DMSO-$d_6$): δ=9.14 (s, 1H), 8.80 (s, 1H), 7.96-7.89 (m, 1H), 7.47 (s, 1H), 7.23 (s, 1H), 6.70 (t, J=55.6 Hz, 1H), 4.41-4.28 (m, 1H), 3.75 (s, 3H), 3.59-3.55 (m, 2H), 2.99-2.93 (m, 2H), 2.88 (s, 3H), 2.04-2.00 (m, 2H), 1.84 (s, 3H), 1.64-1.55 (m, 2H).

Embodiment 17: Preparation of Compound 20

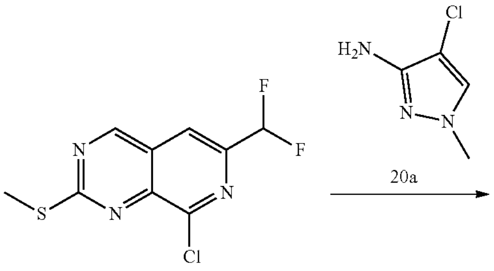

14c

-continued

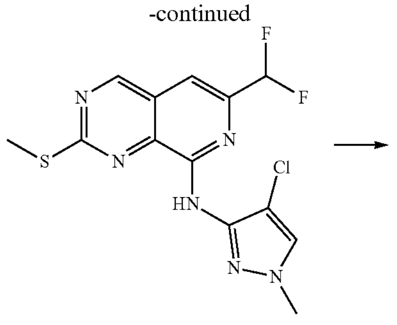

20b

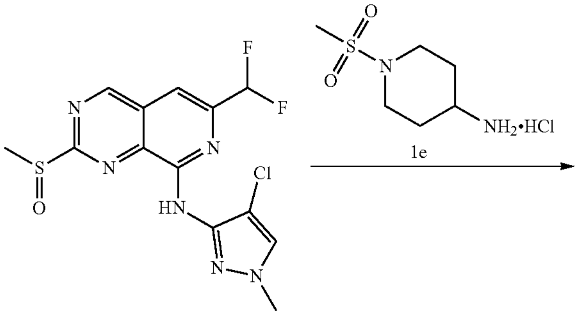

20c

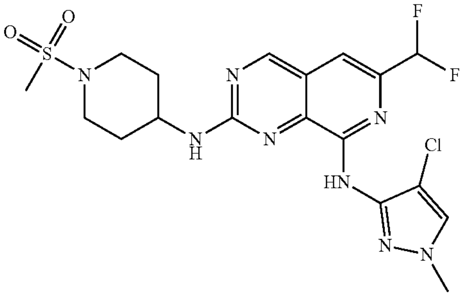

20

Step 1:

Under nitrogen protection, 14c (1 g, 3.82 mmol, 1 eq), 20a (1.01 g, 7.64 mmol, 2 eq), sodium tert-butoxide (1.10 g, 11.46 mmol, 3 eq) and dicyclohexyl-[2-(2,4,6-triaisopropheny)phenyl] phosphorus; methanesulfonate; [2-[2-(methylamino)phenyl]phenyl]palladium (164.41 mg, 191.07 μmol, 0.05 eq) were added to 1,4-dioxane (15 mL). The mixture was warmed to 100° C. and stirred for 1 hour. After cooling, the mixture was concentrated in vacuo to obtain a residue. The residue was purified by column chromatography (petroleum ether:ethyl acetate=3:1) to obtain product 20b.

Step 2:

At 25° C., m-chloroperoxybenzoic acid (682.83 mg, 3.36 mmol, 85% purity, 1.2 eq) was added to a solution of 20b (1 g, 2.80 mmol, 1 eq) in dichloromethane (15 mL). The mixture was stirred for 1 hour. The mixture was quenched with aqueous sodium sulfite (20 mL) and stirred for 5 minutes, extracted with dichloromethane (20 mL*2), the combined organic phase was dried over anhydrous $Na_2SO_4$, filtered and concentrated in vacuo to obtain product 20c.

Step 3:

At 25° C., DIPEA (624.06 mg, 4.83 mmol, 841.05 μL, 3 eq) and 1e (691.17 mg, 3.22 mmol, 2 eq, hydrochloride salt) were added to a solution of 20c (600 mg, 1.61 mmol, 1 eq) in dimethyl sulfoxide (6 mL). The mixture was warmed to 100° C. and stirred for 1 hour. The mixture was diluted with water (10 mL), extracted with ethyl acetate (10 mL*2), the combined organic phase was dried over anhydrous $Na_2SO_4$, filtered and concentrated in vacuo to obtain a residue, the residue was purified by preparative HPLC (column: 3_Phenomenex Luna C18 75*30 mm*3 μm; mobile phase: [Water (HCl)-ACN]; ACN %: 37%-57%, 7 min) to obtain 20. LCMS(ESI) m/z: 486.9 (M+1); $^1$H NMR (400 MHz, DMSO-$d_6$) δ=9.16 (s, 1H), 8.96 (s, 1H), 8.05-7.85 (m, 2H), 7.29 (s, 1H), 6.66 (t, J=55.6 Hz, 1H), 4.34 (d, J=2.4 Hz, 1H), 3.82 (s, 3H), 3.62-3.56 (m, 2H), 3.02-2.83 (m, 5H), 2.09-1.94 (m, 2H), 1.68-1.48 (m, 2H).

Embodiment 18: Preparation of Compound 21 and Compound 22

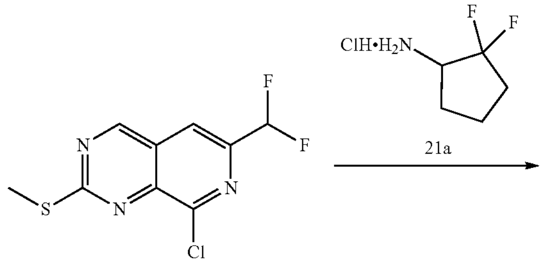

14e

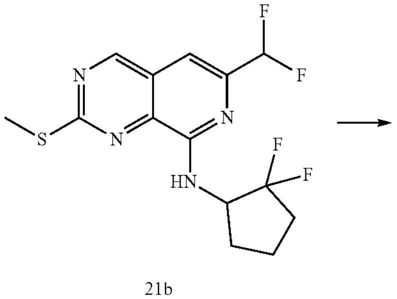

21b

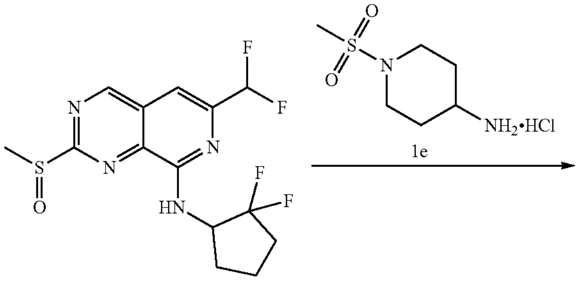

21c

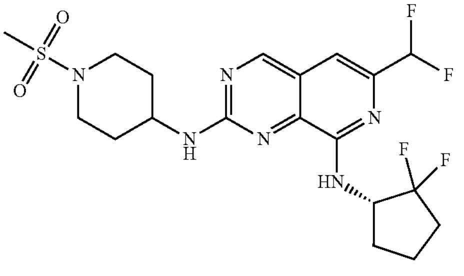

+

21 or 22

-continued

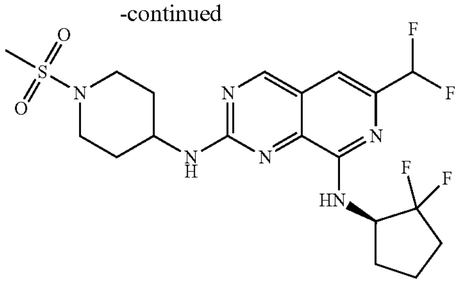

21 or 22

Step 1:

At 20-30° C., compound 21a (3.32 g, 21.09 mmol, 2.3 eq, hydrochloride salt) and DIPEA (5.45 g, 42.19 mmol, 7.35 mL, 4.6 eq) were added successively to a solution of compound 14e (2.4 g, 9.17 mmol, 1 eq) in N-methylpyrrolidone (24 mL), and the reaction solution was reacted at 150° C. for 3 hours under microwave condition. The reaction solution was diluted with water (50 mL), extracted with ethyl acetate (40 mL*2), the combined organic phase was washed with saturated brine (100 mL), dried over anhydrous sodium sulfate, and concentrated under reduced pressure to obtain a residue. The residue was purified by column chromatography (developing agent: petroleum ether:ethyl acetate=1:0 to 10:1) to obtain compound 21b.

Step 2:

At 0° C., m-CPBA (1.23 g, 6.03 mmol, 85% purity, 1.1 eq) was added in portions to a solution of compound 21b (1.9 g, 5.49 mmol, 1 eq) in dichloromethane (20 mL), the reaction solution was reacted at 0° C. for 1 hour. The reaction solution was concentrated under reduced pressure to obtain the crude compound 21c.

Step 3:

At 20-30° C., compound 1e (1.58 g, 7.34 mmol, 2 eq) and diisopropylethylamine (1.90 g, 14.68 mmol, 2.56 mL, 4 eq) were added successively to a solution of compound 21c (1.33 g, 3.67 mmol, 1 eq) in dimethyl sulfoxide (10 mL), and the reaction solution was stirred at 100° C. for 6 hours under nitrogen protection. The reaction solution was diluted with water (30 mL), extracted with ethyl acetate (20 mL*2), the combined organic phase was washed with saturated brine (40 mL), dried over anhydrous sodium sulfate, filtered, and concentrated under reduced pressure to obtain a residue. The crude product was successively purified by column chromatography (developing agent: petroleum ether:ethyl acetate=1:0 to 2:1) and separated by Supercritical Fluid Chromatography (column: DAICEL CHIRALPAK AD (250 mm*30 mm, 10 μm); mobile phase: [0.1% $NH_3H_2O$ MEOH]; B %: 30%-30%, 6.1 min; 120 min) to obtain compound 21 and compound 22. Compound 22 was purified by HPLC (column: 3_Phenomenex Luna C18 75*30 mm*3 μm; mobile phase: [water (0.05% hydrochloric acid)-acetonitrile]; 48%-68%, 6.5 minutes).

Compound 21, LCMS (ESI) m/z: 477.1 $(M+1)^+$, $^1$H NMR (400 MHz, METHANOL-$d_4$): δ=9.01 (s, 1H), 7.13 (s, 1H), 6.53 (t, J=55.6 Hz, 1H), 4.83-4.79 (m, 1H), 4.14-4.07 (m, 1H), 3.76-3.71 (m, 2H), 3.06-3.01 (m, 2H), 2.88 (s, 3H), 2.42-2.16 (m, 6H), 1.92-1.85 (m, 2H), 1.73-1.69 (m, 2H).

Compound 22, LCMS (ESI) m/z: 477.2 $(M+1)^+$, $^1$H NMR (400 MHz, METHANOL-$d_4$): δ=9.03 (s, 1H), 7.19 (s, 1H), 6.59 (t, J=55.6 Hz, 1H), 4.92-4.87 (m, 1H), 4.16-4.07 (m, 1H), 3.77-3.72 (m, 2H), 3.03-2.97 (m, 2H), 2.88 (s, 3H), 2.41-2.14 (m, 6H), 1.93-1.86 (m, 2H), 1.75-1.70 (m, 2H).

Embodiment 19: Preparation of Compound 23 and Compound 24

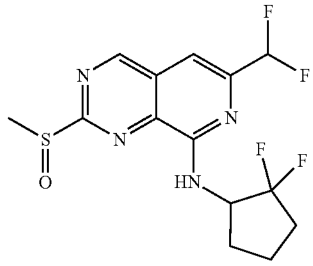

19c

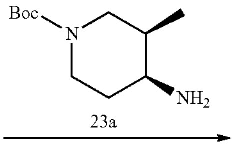

23a

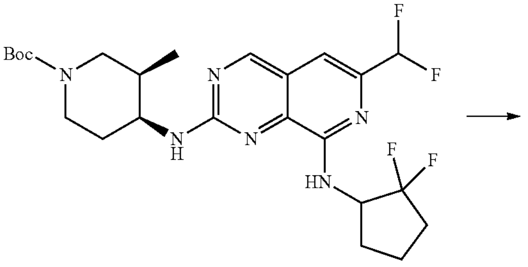

23b

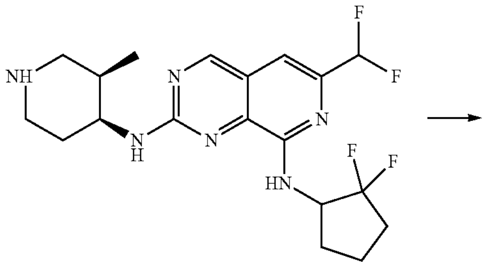

23c

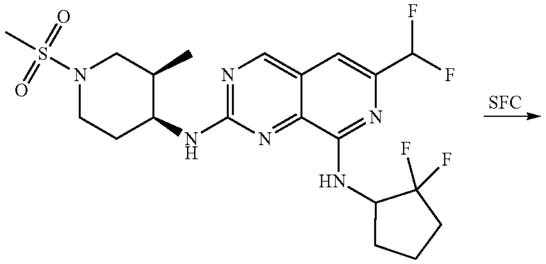

23d

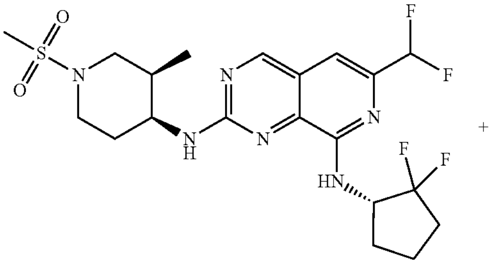

23 or 24

-continued

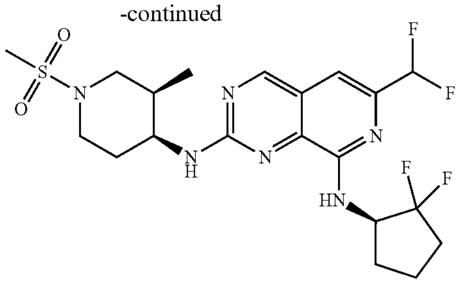

23 or 24

Step 1:

At 20-30° C., compound 23a (118.29 mg, 551.96 μmol, 2 eq) and DLEA (107.01 mg, 827.94 μmol, 144.21 μL, 3 eq) were added successively to a solution of compound 19c (100 mg, 275.98 μmol, 1 eq) in DMSO (3 mL), the reaction solution was stirred at 100° C. for 12 hours under nitrogen protection. The reaction solution was quenched with water (5 mL), extracted twice with ethyl acetate (10 mL), the organic phase was washed with saturated brine (10 mL), dried over anhydrous sodium sulfate, and concentrated to obtain a residue. The residue was purified by silica-gel plate (developing agent: petroleum ether:ethyl acetate=3:1) to obtain compound 23b. LCMS (ESI) m/z: 513.0 $(M+1)^+$.

Step 2:

At 0° C., trifluoroacetic acid (266.95 mg, 2.34 mmol, 173.35 μL, 20 eq) was added dropwise to a solution of compound 23b (60 mg, 117.06 μmol, 1 eq) in dichloromethane (2 mL), the reaction solution was reacted at 0° C. for 0.5 hours under nitrogen protection. The reaction solution was concentrated to obtain compound 23c. LCMS (ESI) m/z: 413.2 $(M+1)^+$.

Step 3:

At 0° C., triethylamine (33.12 mg, 327.33 μmol, 45.56 μL, 3 eq) and methanesulfonyl chloride (18.75 mg, 163.67 μmol, 12.67 μL, 1.5 eq) were added to a solution of compound 23c (45 mg, 109.11 μmol, 1 eq) in dichloromethane (2 mL), the reaction solution was reacted at 0° C. for 0.5 hours under nitrogen protection. The reaction solution was quenched with water (10 mL), extracted three times with dichloromethane (10 mL), the organic phase was washed with saturated brine (10 mL), dried over anhydrous sodium sulfate, and concentrated to obtain a residue. The residue was purified by preparative HPLC (column: Unisil 3-100 C18 Ultra 150*50 mm*3 μm; mobile phase: [water (formic acid)-acetonitrile]; 42%-72%, 10 minutes) to obtain compound 23d. LCMS (ESI) m/z: 491.1 $(M+1)^+$.

Step 4:

Compound 23d was separated by Supercritical Fluid Chromatography (column: DAICEL CHIRALPAK AD-H (250 mm*30 mm, 5 μm); mobile phase: [0.1% ammonia ethanol]; 20%-20%, 4.8 minutes; 40 min) to obtain compound 23 and compound 24.

Compound 23: LCMS (ESI) m/z: 491.2 $(M+1)^+$. $^1H$ NMR (METHANOL-$d_4$, 400 MHz) δ 9.04 (s, 1H), 7.16 (s, 1H), 6.56 (t, J=56.0 Hz, 1H), 4.61 (br s, 1H), 4.36 (br s, 1H), 3.52-3.42 (m, 1H), 3.30-3.22 (m, 2H), 2.89 (s, 3H), 2.42-2.37 (m, 2H), 2.28-2.11 (m, 2H), 2.09-2.03 (m, 2H), 1.95-1.89 (m, 2H), 1.74-1.69 (m, 1H), 1.30-1.33 (m, 1H), 1.07 (d, J=7.0 Hz, 3H).

Compound 24: LCMS (ESI) m/z: 491.2 $(M+1)^+$. $^1H$ NMR (METHANOL-$d_4$, 400 MHz) δ 8.91 (s, 1H), 7.04 (s, 1H), 6.44 (t, J=56.0 Hz, 1H), 4.49 (br s, 1H), 4.29-4.21 (m, 1H), 3.37 (td, J=3.4, 11.4 Hz, 1H), 3.07-3.15 (m, 2H), 2.77 (s, 3H), 2.35-2.25 (m, 2H), 2.19-2.05 (m, 2H), 1.98-1.95 (m, 1H), 1.91-1.88 (m, 1H), 1.86-1.82 (m, 2H), 1.65-1.58 (m, 1H), 1.19-1.16 (m, 1H), 0.94 (d, J=7.0 Hz, 3H).

Embodiment 20: Preparation of Compound 25

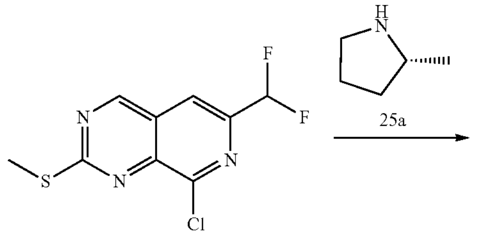

25a

14c

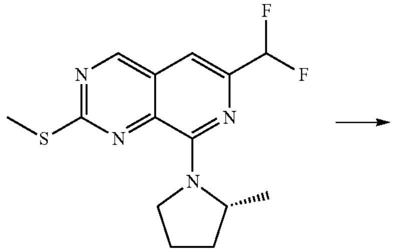

25b

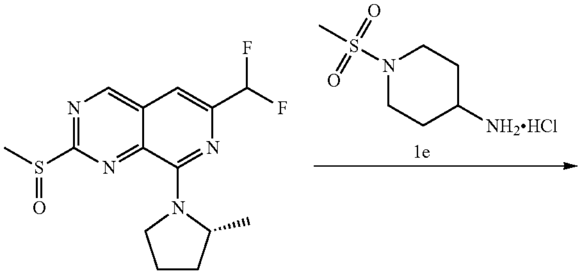

1e

25c

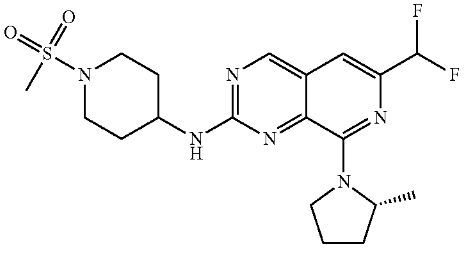

25

Step 1:

At room temperature, compound 14c (80 mg, 305.72 μmol, 1 eq), (2R)-2-methylpyrrole (25a) (65.08 mg, 764.30 μmol, 2.5 eq) and N, N-diisopropylethylamine (197.56 mg, 1.53 mmol, 266.25 μL, 5 eq) were dissolved in dimethyl sulfoxide (2 mL), and the reaction solution was reacted at 150° C. for 3 hours under microwave condition, LCMS showed that the reaction was complete. The reaction solution was added with 5 mL of water, and then extracted three times with ethyl acetate (10 mL*3). The combined organic phase was washed three times with saturated brine (10 mL*3), dried over anhydrous sodium sulfate, filtered and concentrated to obtain a crude product. The crude product was purified by thin-plate chromatography (silica gel, petroleum ether/ethyl acetate=3/1) to obtain compound 25b.

Step 2:

At 0° C., m-CPBA (69.64 mg, 343.01 μmol, 85% purity, 1.2 eq) was added to a solution of compound 25b (90 mg, 285.84 μmol, 98.571% purity, 1 eq) in dichloromethane (5 mL), the reaction solution was reacted at 0° C. for 1 hour. LCMS showed that the reaction was complete. The reaction solution was quenched with saturated sodium sulfite (5 mL) at 0° C., diluted with 5 mL of water, then extracted three times with dichloromethane (10 mL*3), and the combined organic phase was washed with saturated aqueous sodium bicarbonate twice (15 mL*2), dried over anhydrous sodium sulfate, filtered and concentrated to obtain crude compound 25c.

Step 3:

At room temperature, N, N-diisopropylethylamine (178.20 mg, 1.38 mmol, 240.17 μL, 3 eq) and compound 1e (148.03 mg, 689.41 μmol, 1.5 eq) were added to a solution of compound 25c (150 mg, 459.61 μmol, 1 eq) in dimethyl sulfoxide (5 mL), the reaction solution was stirred at 100° C. for 4 hours. LCMS showed that the reaction was complete. The reaction solution was added with 5 mL of water, and extracted three times with ethyl acetate (10 mL*3), the combined organic phase was washed with saturated sodium brine three times (10 mL*3), dried over anhydrous sodium sulfate, filtered, and concentrated to obtain a crude product. The crude product was purified by preparative HPLC (column: Welch Ultimate XB-CN 250*50*10 μm; mobile phase: [Heptane-EtOH]; B %: 15%-55%, 15 min) to obtain compound 25. LCMS(ESI) m/z: 441.3 (M+1) $^1$H NMR (400 MHz, DMSO-$d_6$) δ=9.08 (s, 1H), 7.72 (s, 1H), 7.09 (s, 1H), 6.71 (t, J=56.0 Hz, 1H), 5.00-4.87 (m, 1H), 4.17-4.04 (m, 1H), 3.98-3.82 (m, 2H), 3.64-3.54 (m, 2H), 3.47-3.40 (m, 2H), 2.95-2.85 (m, 4H), 2.14-2.07 (m, 1H), 2.07-1.95 (m, 3H), 1.93-1.81 (m, 1H), 1.74-1.54 (m, 2H), 1.23 (d, J=6.13 Hz, 3H).

Embodiment 21: Preparation of Compound 26

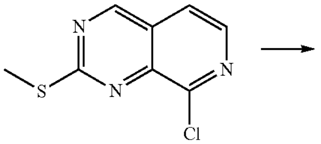

1a

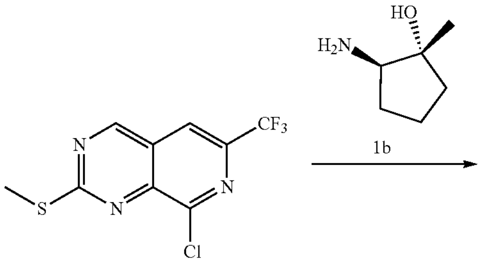

1b

26a

-continued

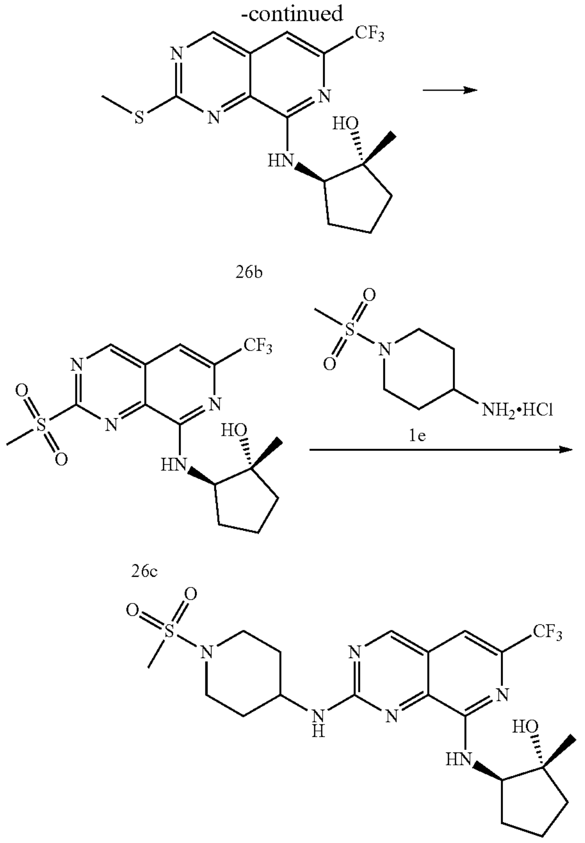

26b

26c

26

Step 1:

At 25° C., tert-butyl hydrogen peroxide (364.93 mg, 2.83 μmol, 388.23 μL, 70% purity, 6 eq) was gradually added to a solution of compound 1*a* (100 mg, 472.43 μmol, 1 eq) and sodium trifluoromethanesulfinate (368.64 mg, 2.36 mmol, 368.64 μL, 5 eq) in DMSO (4 mL), and the reaction solution was reacted at 25° C. for 15 hours. The reaction solution was quenched with 10 mL of ethylenediaminetetraacetic acid disodium/$NaHCO_3$ solution and 5 mL of water, then diluted with 10 mL of ethyl acetate, extracted with ethyl acetate (10 mL*3), the combined organic phase was washed with saturated brine (30 mL*2), dried over anhydrous sodium sulfate, and concentrated under reduced pressure to obtain a residue. The residue was purified by pre-TLC (developing agent: petroleum ether: ethyl acetate=5:1) to obtain compound 26a, MS (M+1): 280.2.

Step 2:

DIEA (36.97 mg, 286.05 μmol, 49.82 μL, 2 eq) was added to a solution of compound 26a ((40 mg, 143.03 μmol, 1 eq)) and 1b in DMSO (1.5 mL), and the reaction solution was reacted at 120° C. for 12 hours. The reaction solution was diluted with ethyl acetate (6 mL) and poured into 10 mL of water at room temperature, and extracted with ethyl acetate (6 mL*3). The combined organic phase was washed with saturated brine (20 mL*1), dried over anhydrous sodium sulfate, and concentrated under reduced pressure to obtain a residue. The residue was purified by column chromatography (developing agent: petroleum ether:ethyl acetate=5:1) to obtain compound 26b, MS (M+1): 359.3.

Step 3:

At 25° C., the compound of potassium peroxomonosulfate and dipotassium sulfate and potassium bisulfate (102.92 mg, 167.42 μmol, 2 eq) was added to a solution of compound 26b (30 mg, 83.71 μmol, 1 eq) in THF (3 mL) and H2O (1 mL). The reaction solution was reacted at 25° C. for 2 hours. The reaction solution was quenched with 6 mL of saturated sodium sulfite, extracted with ethyl acetate (6 mL*3), the combined organic phase was washed with saturated brine (15 mL), dried over anhydrous sodium sulfate, and concentrated under reduced pressure to obtain a residue. Crude 26c was used directly in the next step without further purification. MS (M+1): 375.2.

Step 4:

DIEA (33.14 mg, 256.42 μmol, 44.66 μL, 3 eq) and 1e (22.85 mg, 128.21 μmol, 1.5 eq) were added successively to a solution of compound 26c (32 mg, 85.47 μmol, 1 eq) in DMSO (1.5 mL), and the reaction solution was reacted for 2 h at 100° C. The reaction solution was poured into water (10 mL) at room temperature, then diluted with ethyl acetate (6 mL), extracted with ethyl acetate (6 mL*3), the combined organic phase was washed with saturated brine (20 mL*1), dried over anhydrous sodium sulfate, and concentrated under reduced pressure to obtain a residue. The residue was purified by HPLC (column: Phenomenex luna C18 150*25 mm*10 μm; mobile phase: [Water (0.225% FA)-ACN]; B %: 41%-71%, 10 min) to obtain compound 26. MS (M+1): 489.4. $^1$H NMR (400 MHz, METHANOL-$d_4$) δ=9.02 (s, 1H), 7.27 (s, 1H), 4.30-4.09 (m, 2H), 3.74 (d, J=12.2 Hz, 2H), 3.01 (t, J=11.0 Hz, 2H), 2.88 (s, 3H), 2.41-2.26 (m, 1H), 2.17 (d, J=11.4 Hz, 2H), 1.96-1.64 (m, 7H), 1.18 (s, 3H).

Embodiment 22: Preparation of Compound 27

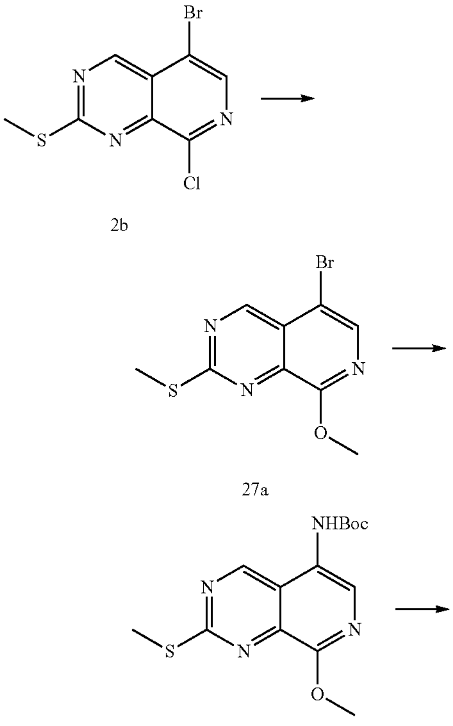

2b

27a

27b

-continued

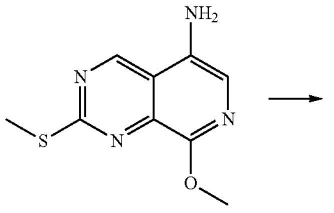

27c

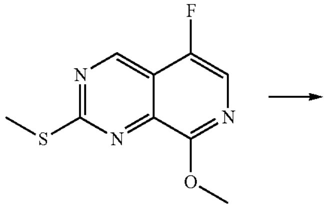

27d

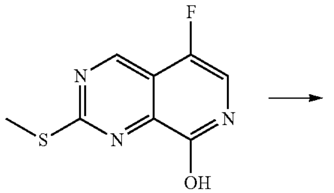

27e

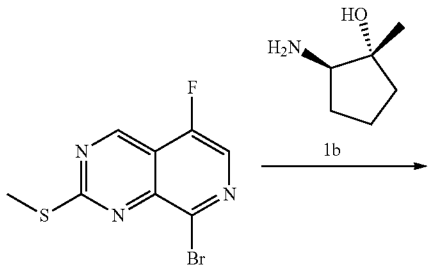

27f

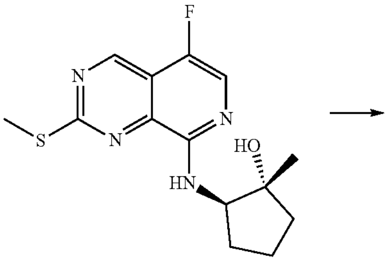

27g

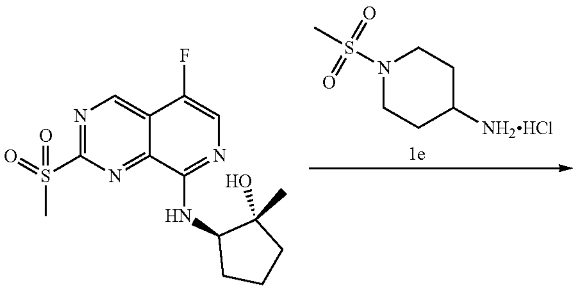

27h

-continued

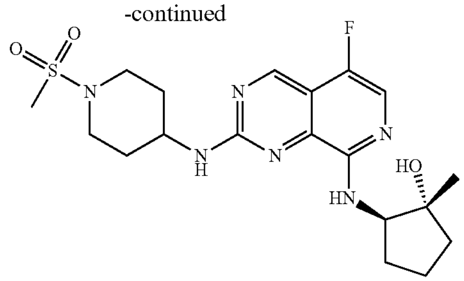

27

Step 1:

Sodium methoxide (2.42 g 44.74 mmol, 1.3 eq) was added to a solution of compound 2b (10 g, 34.42 mmol, 1 eq) in THF (50 mL) and methanol (50 mL), and the reaction solution was reacted at 20° C. 2 hours. The reaction solution was filtered, the filter cake was washed with water (10 mL*5) and methanol (10 mL*5), and the filter cake was dried in vacuum to obtain compound 27a.

Step 2:

Under nitrogen atmosphere, cesium carbonate (22.77 g, 69.89 mmol, 2 eq), tris(dibenzylideneacetone)dipalladium (1.60 g, 1.75 mmol, 0.05 eq) and 4,5-diphenylphosphine-9, 9-dimethyloxacene (2.02 g, 3.49 mmol, 0.1 eq) were added to a solution of compound 27a (10 g, 34.95 mmol, 1 eq) and tert-butyl carbamate (6.55 g, 55.92 mmol, 1.6 eq) in 1,4-dioxane (200 mL). The reaction solution was replaced with nitrogen for three times, and the reaction solution was reacted at 100° C. for 16 hours. The reaction solution was filtered with celite, the filter cake was washed with ethyl acetate (30 mL×3), and the filtrate was concentrated under reduced pressure to obtain a residue. The residue was purified by column chromatography (developing agent: petroleum ether: ethyl acetate=20:1 to 5:1) to obtain compound 27b. MS (M+1): 323.0.

Step 3:

300 mL of water was added to a solution of compound 27b (4 g 12.41 mmol, 1 eq) in 1, 4-dioxane (30 mL), and the reaction solution was reacted at 110° C. for 48 h. After the reaction was completed, the solution was filtered and the filter cake was dried in vacuum to get the product. The filtrate was extracted with ethyl acetate (200 mL*2), the combined organic phase was washed with saturated brine (200 mL*1), dried over anhydrous sodium sulfate, and concentrated under reduced pressure to obtain the product 27c. MS (M+1): 222.8.

Step 4:

Under nitrogen protection, lithium tetrafluoroborate (2.28 g, 24.30 mmol) was added to a suspension of 27c (0.27 g, 1.21 mmol) in acetonitrile (5 mL), cooled to an external temperature of 0-5° C., tert-butyl nitrite (0.15 g, 1.46 mmol) was added, stirred for 5 minutes, anhydrous toluene (30 mL) was added, and heated to an external temperature of 120° C. and stirred for 2 hours. The reaction solution was concentrated and then separated by thin layer chromatography preparative separation plate (petroleum ether:ethyl acetate 8:1 (v/v)) to obtain 27d (81 mg, 0.3 mmol). LCMS (ESI) m/z: 226.10 (M+1).

Step 5:

Under nitrogen protection, hydrobromic acid/acetic acid solution (2 mL, 33%) was added to 27d (81 mg, 0.3 mmol) and stirred at 50° C. for 2 h, then the mixture was concentrated to obtain crude product 27e.

Step 6:

Under nitrogen protection, phosphorus oxybromide (373 mg, 1.3 mmol) was added to a solution of 27e (55 mg, 260 μmol) in acetonitrile (1 mL), and the reaction solution was stirred at 75° C. for 1 hour. The reaction solution was diluted with ethyl acetate (50 mL), washed with water (20 mL*3) and saturated brine (20 mL), dried over anhydrous sodium sulfate, filtered and concentrated, and separated by preparative plate (petroleum ether:ethyl acetate 8:1 (v/v)) to obtain 27f.

Step 7:

$Pd_2(dba)_3$ (5 mg, 5.4 μmol), t-Bu Xphos (4.9 mg, 12 μmol) and sodium tert-butoxide (11.2 mg, 120 μmol) were added to a solution of 27f (16 mg, 58 μmol) and 1b (6.7 mg, 58 μmol) in dioxane (1 mL) under nitrogen protection. The reaction solution was stirred at 90° C. for 2 hours. The reaction solution was diluted with ethyl acetate (50 mL), washed with water (20 mL*3) and saturated brine (20 mL), dried over anhydrous sodium sulfate, filtered and concentrated, and separated by preparative plate (petroleum ether: ethyl acetate 3:1 (v/v)) to obtain 27g.

Step 8:

m-CPBA (19.7 mg, 97 μmol, 85%) was added to a solution of 27 g (15 mg, 48.6 μmol) in dichloromethane (1 mL), and stirred at 30° C. for 2 hours. The reaction solution was directly separated by preparative separation plate (EtOAc) to obtain 27h. LCMS (ESI) m/z: 341.1 (M+1).

Step 9:

Under nitrogen protection, diisopropylethylamine (6 mg, 46 μmol) was added to a solution of 27h (8 mg, 23 μmol) and 1e (5.6 mg, 26 μmol) in DMSO (0.5 mL), and stirred for 2 h at 105° C. LCMS showed that the reaction was complete. The reaction solution was diluted with ethyl acetate (50 mL), washed with water (20 mL*2), washed with saturated brine (20 mL), dried over sodium sulfate, filtered, concentrated, and the residue was separated by preparative TLC (EtOAc) to obtain 27. LCMS (ESI) m/z: 439.18 (M+1). $^1H$ NMR (400 MHz, CDCl3) δ=9.07 (s, 1H), 7.46 (s, 1H), 4.03 (br, 2H), 3.73 (d, J=13.2 Hz, 2H), 2.99-2.94 (m, 2H), 2.92 (s, 3H), 2.18-2.15 (m, 4H), 1.80-1.65 (m, 6H), 1.06 (s, 3H).

Embodiment 23: Preparation of Compound 28 and Compound 29

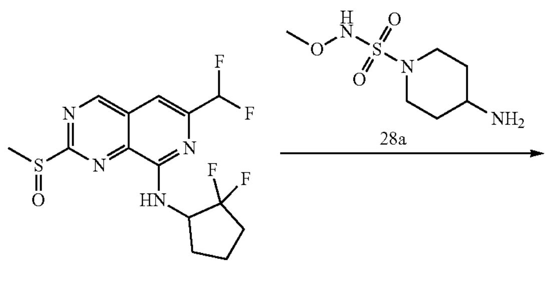

19c

-continued

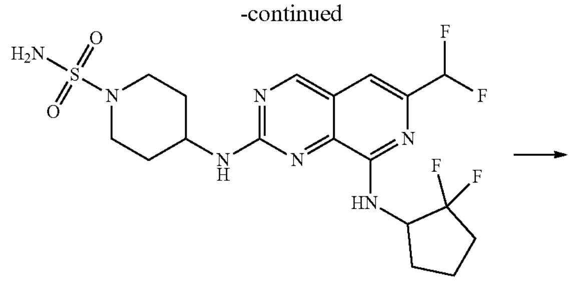

28b

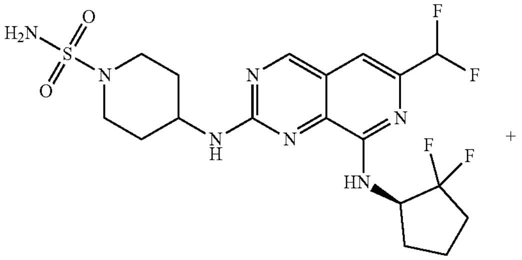

+

28 or 29

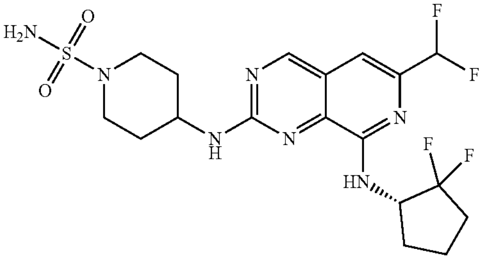

28 or 29

Step 1:

At 20-30° C., compound 28a (34.65 mg, 165.59 μmol, 2 eq) and DIEA (32.10 mg, 248.38 μmol, 43.26 μL, 3 eq) were added to a solution of compound 19c (30 mg, 82.79 μmol, 1 eq) in dimethyl sulfoxide (1 mL), and the reaction solution was reacted at 100° C. for 12 hours under nitrogen protection. The reaction solution was quenched with water (5 mL), extracted three times with ethyl acetate (10 mL), the organic phase was washed with saturated brine (10 mL), dried over anhydrous sodium sulfate, and concentrated to obtain a residue. The residue was purified by preparative HPLC (column: Phenomenex C18 75*30 mm*3 μm; mobile phase: [water (formic acid)-acetonitrile]; 38%-68%, 7 minutes) to obtain compound 28b.

Step 2:

28b was separated by Supercritical Fluid Chromatography (column: DAICEL CHIRALPAK AD-H (250 mm*30 mm, 5 μm); mobile phase: [0.1% ammonia ethanol]; 30%-30%, 3.5 minutes; 40 min) to obtain compound 28 or 29. LCMS (ESI) m/z: 478.1 (M+1)+. $^1H$ NMR (METHANOL-d4, 400 MHz) δ 8.90 (s, 1H), 7.03 (s, 1H), 6.44 (t, J=56 Hz, 1H), 4.51 (br s, 1H), 3.96-3.85 (m, 1H), 3.58-3.54 (m, 2H), 2.79-2.70 (m, 2H), 2.35-2.25 (m, 1H), 2.20-2.05 (m, 4H), 1.83-1.72 (m, 2H), 1.65-1.56 (m, 3H). Compound 28 or compound 29. LCMS (ESI) m/z: 478.1 (M+1)+. $^1H$ NMR (METHANOL-$d_4$, 400 MHz) δ 8.90 (s, 1H), 7.03 (s, 1H), 6.44 (t, J=56.0 Hz, 1H), 4.51 (s, 1H), 3.95-3.85 (m, 1H), 3.60-3.55 (m, 2H), 2.79-2.71 (m, 2H), 2.35-2.26 (m, 1H), 2.20-2.03 (m, 4H), 1.86-1.72 (m, 2H), 1.69-1.53 (m, 3H).

Embodiment 24: Preparation of Compound 30 and Compound 31

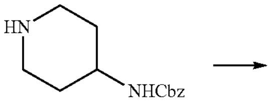

30a

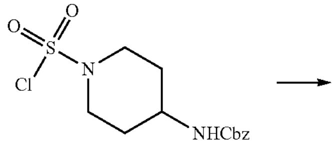

30b

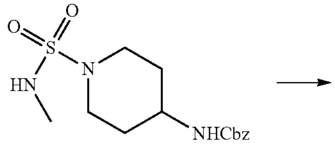

30c

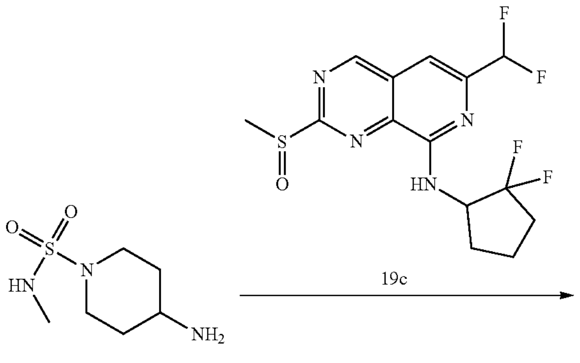

30d

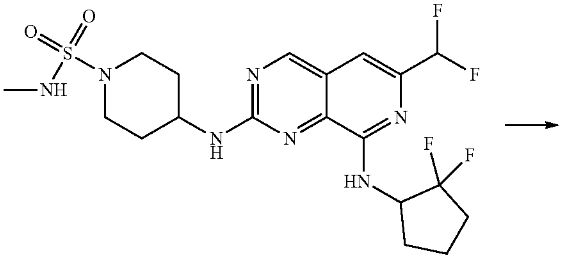

30e

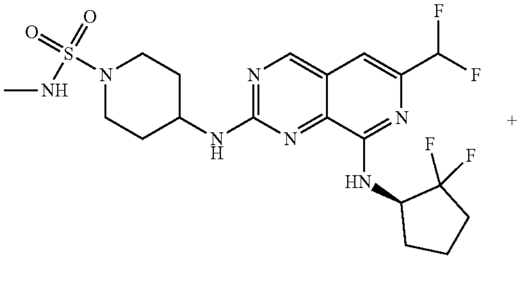

30 or 31

-continued

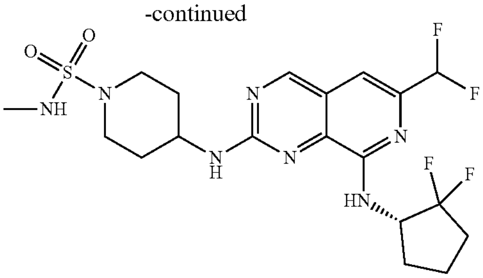

30 or 31

Step 1:

At 0° C., triethylamine (1.04 g, 10.24 mmol, 1.43 mL, 1.2 eq) and methanesulfonyl chloride (1.27 g, 9.39 mmol, 938.78 μL, 1.1 eq) were added dropwise to a solution of compound 30a (2 g, 8.54 mmol, 1 eq) in dichloromethane (20 mL), and the reaction solution was stirred at 20° C. for 2 hours. Compound 30b was obtained, and this reaction solution was directly used for the next reaction.

Step 2:

At 0° C., triethylamine (3.45 g, 34.13 mmol, 4.75 mL, 4 eq) and methylamine (2 mol/L, 12.80 mL, 3 eq) were added to a solution of compound 30b (2.84 g, 8.53 mmol, 1 eq) in dichloromethane (20 mL), and the reaction solution was stirred at 20° C. for 13 hours. After the reaction was completed, the reaction solution was poured into a solution of water (50 mL) and dichloromethane (100 mL). The organic phase was separated, dried over anhydrous sodium sulfate, filtered, and concentrated to obtain a crude product. The crude product was purified by thin plate chromatography (silica gel, petroleum ether/ethyl acetate=1/1) to obtain compound 30c. $^1$H NMR (400 MHz, CHLOROFORM-d) δ=7.34-7.22 (m, 5H), 5.10-4.93 (m, 2H), 4.76-4.57 (m, 1H), 4.12-3.93 (m, 1H), 3.69-3.46 (m, 3H), 2.97-2.76 (m, 2H), 2.06-1.86 (m, 2H), 1.50-1.35 (m, 2H).

Step 3:

At room temperature, palladium carbon (0.2 g, 1.22 mmol, 10% purity) was added to a solution of compound 30c (0.6 g, 1.83 mmol, 1 eq) in tetrahydrofuran (5 mL) under nitrogen protection. The solution was replaced with hydrogen several times, and reacted at 20° C. for 16 hours under hydrogen protection (15 psi). After the reaction was completed, the reaction solution was filtered and concentrated to obtain compound 30d. $^1$H NMR (400 MHz, DMSO-d) δ=7.08-6.90 (m, 1H), 3.54-3.37 (m, 1H), 3.41 (td, J=3.3, 12.4 Hz, 3H), 2.78-2.59 (m, 3H), 2.50 (br s, 3H), 1.85-1.64 (m, 2H), 1.32-1.14 (m, 2H).

Step 4:

N,N-diisopropylethylamine (56.63 mg, 438.15 μmol, 76.32 μL, 3 eq) and compound 19c (42.34 mg, 219.07 μmol, 1.5 eq) were added to a solution of compound 30d (90 mg, 146.05 μmol, 58.8% purity, 1 eq) in dimethyl sulfoxide (2 mL). The reaction solution was stirred at 100° C. for 3 hours. The reaction solution was quenched with 10 mL of water, extracted three times with ethyl acetate (10 mL*3), the combined organic phase was washed three times with saturated brine (10 mL*3), dried over anhydrous sodium sulfate, filtered, and concentrated to obtain a crude product. The crude product was purified by preparative HPLC (column: Phenomenex Gemini-NX C18 75*30 mm*3 μm; mobile phase: [water (0.225% FA)-ACN]; ACN %: 40%-70%, 7 min) to obtain compound 30e.

Step 5:

30e was separated by Supercritical Fluid Chromatography (column: DAICEL CHIRALCEL OJ (250 mm*30 mm, 10 μm); mobile phase: [0.1% $NH_3H_2O$ MEOH]; B %: 30%-30%, 3.8 min; 30 min) to obtain compound 30 and compound 31.

Compound 30: LCMS(ESI) m/z: 491.17 (M+1) $^1H$ NMR (400 MHz, DMSO-$d_6$) δ=9.29-9.04 (m, 1H), 8.09-7.89 (m, 1H), 7.29-7.15 (m, 1H), 7.13-7.04 (m, 1H), 6.92-6.73 (m, 2H), 6.64-6.61 (m, 1H), 4.97-4.71 (m, 1H), 4.08-3.91 (m, 1H), 3.59-3.48 (m, 3H), 3.02-2.76 (m, 2H), 2.32-2.14 (m, 3H), 2.05-1.90 (m, 2H), 1.90-1.73 (m, 3H), 1.70-1.50 (m, 3H).

Compound 31: LCMS(ESI) m/z: 491.17 (M+1) $^1H$ NMR (400 MHz, DMSO-$d_6$) δ=9.32-9.01 (m, 1H), 8.09-7.86 (m, 1H), 7.24-7.19 (m, 1H), 7.14-7.05 (m, 1H), 6.93-6.61 (m, 2H), 6.95-6.56 (m, 1H), 4.90-4.73 (m, 1H), 4.07-3.96 (m, 1H), 3.57-3.48 (m, 3H), 2.95-2.83 (m, 2H), 2.32-2.16 (m, 3H), 2.06-1.92 (m, 2H), 1.88-1.73 (m, 3H), 1.68-1.52 (m, 3H).

Embodiment 25: Preparation of Compound 32

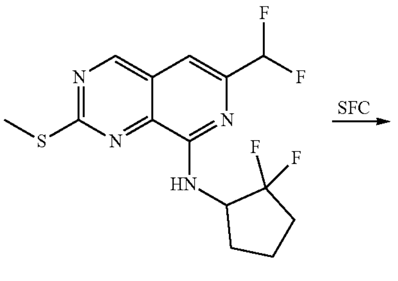

19c

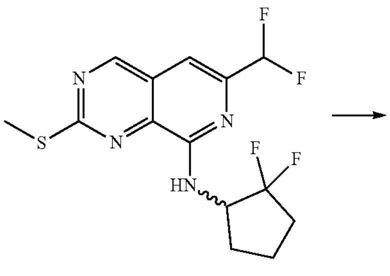

32a

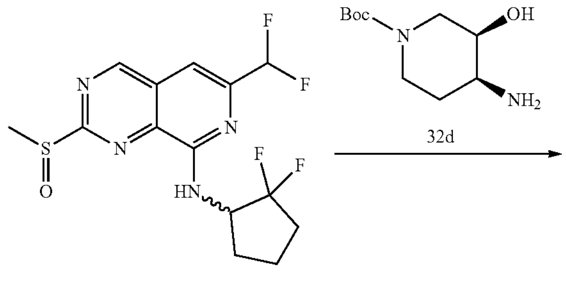

32d

32c

-continued

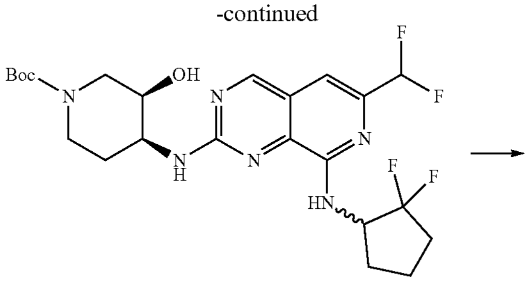

32e

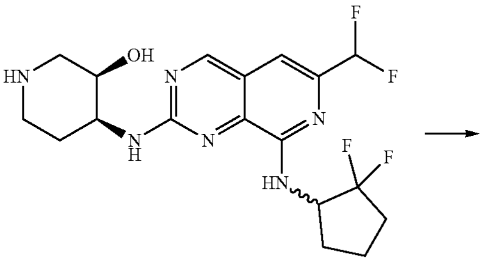

32f

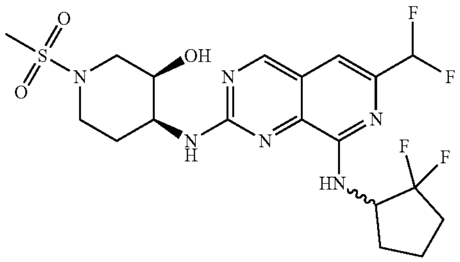

32

Step 1:

3 g of 19c was separated by Supercritical Fluid Chromatography (column: Phenomenex luna C18 250*80 mm*10 μm; mobile; mobile phase: [water (0.1% TFA)-ACN]; ACN %: 60%-90%, 21 min to obtain compound 32a (retention time: 1.150 min) and 32b (retention time: 1.259 min).

32a or 32b

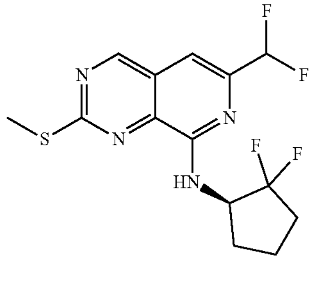

-continued 32b or 32a

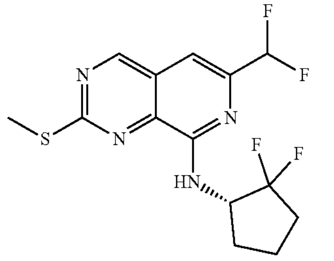

Step 2:

At 0° C., m-chloroperoxybenzoic acid (25.79 mg 127.04 pol, 85% purity, 1.1 eq) was added to a solution of compound 32a (40 mg 115.49 μmol, 1 eq) in dichloromethane (5 mL), and stirred at 0° C. for 30 minutes. After the reaction was completed, the reaction solution was quenched with saturated sodium sulfite (5 mL) at 0° C., diluted with 5 mL of water, then extracted three times with dichloromethane (10 mL*3), and the combined organic phase was washed with saturated aqueous sodium bicarbonate (15 mL*2), dried over anhydrous sodium sulfate, filtered, and concentrated to obtain crude compound 32c.

Step 3:

At room temperature, N,N-diisopropylethylamine (99.87 mg 772.74 μmol, 134.60 μL, 4 eq) and compound 32d (83.56 mg, 386.37 μmol, 2 eq) were added to a solution of compound 32c (70 mg 193.19 μmol, 1 eq) in dimethyl sulfoxide (5 mL). The reaction solution was stirred at 100° C. for 16 hours. After the reaction was complete, 10 mL of water was added to the reaction solution, and extracted with ethyl acetate three times (10 mL*3), the combined organic phase was washed with saturated brine (10 mL*3), dried over anhydrous sodium sulfate, filtered, and concentrated to obtain a crude product. The crude product was purified by plate chromatography (silica, petroleum ether:ethyl acetate=1:1) to obtain compound 32e.

Step 4:

At 0° C., trifluoroacetic acid (1.54 g, 13.51 mmol, 1 mL, 138.98 eq) was added to a solution of compound 32e (50 mg, 97.18 μmol, 1 eq) in dichloromethane (2 mL), and stirred at 0° C. for 1 h. After the reaction was complete, the reaction solution was concentrated to obtain the crude product 32f.

Step 5:

At 0° C., sodium bicarbonate (36.49 mg, 434.36 μmol, 16.89 μL, 3 eq) and methanesulfonyl chloride (49.76 mg, 434.36 μmol, 33.62 μL, 2 eq) were added to a solution of compound 32f (60 mg, 144.79 μmol, 1 eq) in water (1 mL) and ethyl acetate (1 mL). The reaction solution was stirred at 0° C. for 1 hour, analysis showed that the reaction was not complete, and the temperature was raised to 20° C. and the reaction solution was stirred for 12 hours. After the reaction was complete, the reaction solution was added with 10 mL of water, and extracted with ethyl acetate (10 mL*3), the combined organic phase was washed with saturated brine (10 mL*3), dried over anhydrous sodium sulfate, and filtered, concentrated to obtain a crude product. The crude product was purified by preparative HPLC (column: Phenomenex C18 75*30 mm*3 μm; mobile phase: [water (FA)-ACN]; ACN %: 35%-65%, 7 min) to obtain compound 32. LCMS(ESI) m/z: 492.16 $^1$H NMR (400 MHz, DMSO-$d_6$) δ=9.31-9.05 (m, 1H), 7.64-7.14 (m, 2H), 7.11-6.56 (m, 2H), 5.31-5.16 (m, 1H), 4.92-4.76 (m, 1H), 4.25-4.12 (m, 1H), 4.10-4.00 (m, 1H), 3.77-3.62 (m, 2H), 3.18-2.98 (m, 2H), 2.94 (s, 3H), 2.29-2.20 (m, 3H), 2.05-1.87 (m, 1H), 1.88-1.68 (m, 4H).

Embodiment 26: Preparation of Compound 33 and Compound 34

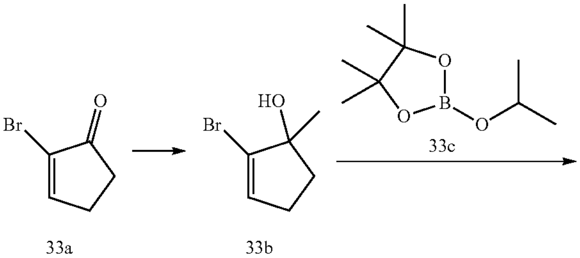

33a

33b

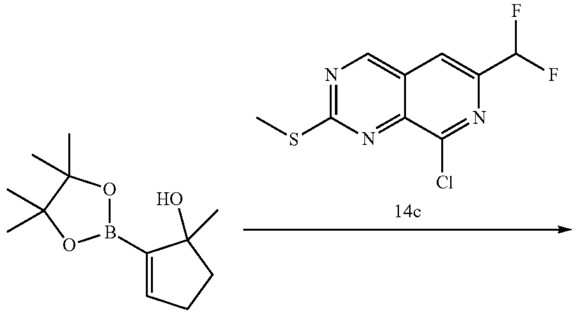

33d

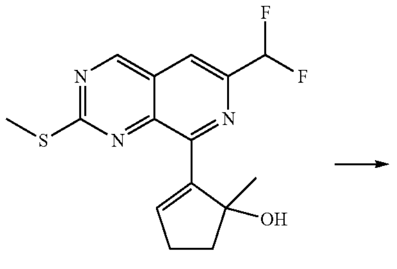

33e

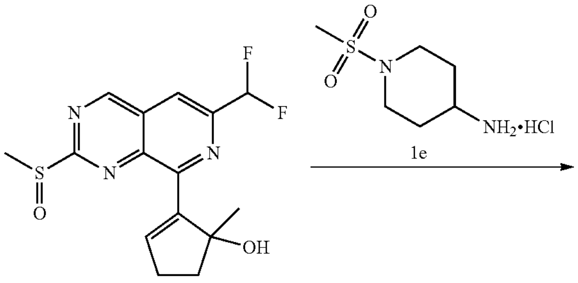

33f

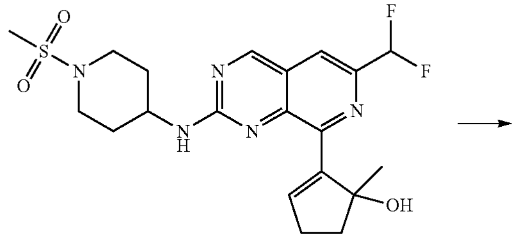

33g

-continued

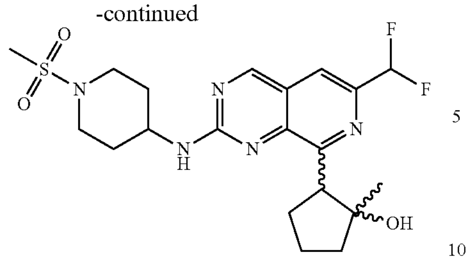

33 or 34

Step 1:

At −78° C., methyl lithium (3 mol/L, 41.41 mL, 2 eq) was added dropwise to a solution of compound 33a (10 g, 62.11 mmol, 1 eq) in tetrahydrofuran (20 mL), and the reaction solution was stirred at −78 C for 0.5 hours under nitrogen protection. The reaction solution was quenched with saturated ammonium chloride solution (100 mL), extracted twice with ethyl acetate (150 mL), the combined organic phase was washed with saturated sodium chloride (150 mL), dried over anhydrous sodium sulfate, and concentrated to obtain a residue. The residue was purified by column chromatography (developing agent: petroleum ether:ethyl acetate=1:0 to 8:1) to obtain compound 33b (2.8 g, 15.82 mmol, 25.46% yield). $^1$H NMR (400 MHz, DMSO-$d_6$): δ=5.92 (t, J=2.6 Hz, 1H), 2.36-2.27 (m, 1H), 2.21-2.12 (m, 1H), 2.03-1.88 (m, 2H), 1.18 (s, 3H).

Step 2:

At −78° C., tert-butyllithium (1.3 mol/L, 42.58 mL, 2 eq) was added dropwise to a solution of compound 33b (2.8 g, 15.82 mmol, 1 eq) in tetrahydrofuran (60 mL), the temperature was slowly raised to −20° C. under nitrogen protection, and the reaction solution was stirred at −20° C. for 0.5 hours, then the reaction solution was cooled to −78° C., compound 33c (7.36 g, 39.54 mmol, 8.07 mL, 2.5 eq) was added slowly to the reaction solution, the temperature was slowly raised to −20° C., and the reaction solution was stirred for 0.5 hours. At −20° C., acetic acid (3 mL) was added dropwise to the reaction solution to quench the reaction, then 80 mL of water was added to dilute the reaction solution, then the reaction solution was extracted with ethyl acetate (100 mL), the organic phase was dried over anhydrous sodium sulfate, filtered, concentrated under reduced pressure to obtain crude compound 33d (6.6 g).

Step 3:

At 20-30° C., compound 14c (1.07 g, 4.78 mmol, 2.5 eq), bis(tri-tert-butylphosphine) palladium (48.82 mg, 95.54 μmol, 0.05 eq) and potassium phosphate (1.22 g, 5.73 mmol, 3 eq) was were successively to a solution of compound 33d (0.5 g, 1.91 mmol, 1 eq) in the mixed solution of dioxane (10 mL) and water (2 mL), the reaction solution was stirred at 90° C. for 1 hour under nitrogen protection. The reaction solution was diluted with water (20 mL), extracted with ethyl acetate (20 mL*2), the combined organic phase was washed with saturated brine (30 mL), dried over anhydrous sodium sulfate, filtered, and concentrated under reduced pressure to obtain a residue. The residue was purified by column chromatography (developing agent: petroleum ether:ethyl acetate=1:0-5:1) to obtain compound 33e (0.36 g, 1.11 mmol, 58.27% yield). $^1$H NMR (400 MHz, DMSO-d6): δ=9.61 (s, 1H), 8.17 (s, 1H), 7.66 (t, J=2.8 Hz, 1H), 7.37-7.09 (m, 1H), 5.12 (s, 1H), 2.65 (s, 3H), 2.64-2.59 (m, 1H), 2.56-2.52 (m, 1H), 2.06-2.00 (m, 2H), 1.52 (s, 3H).

Step 4:

At 0° C., m-CPBA (248.62 mg, 1.22 mmol, 85% purity, 1.1 eq) was added in portions to a solution of compound 33e (0.36 g, 1.11 mmol, 1 eq) in dichloromethane (10 mL), the reaction solution was reacted at 0° C. for 1 hour under nitrogen protection. The reaction solution was concentrated under reduced pressure to obtain crude compound 33f (0.378 g).

Step 5:

At 20-30° C., compound 1e (478.32 mg, 2.23 mmol, 2 eq, hydrochloride salt) and diisopropylethylamine (575.84 mg, 4.46 mmol, 776.06 μL, 4 eq) were added successively to a solution of compound 33f (0.378 g, 1.11 mmol, 1 eq) in dimethyl sulfoxide (5 mL), and the reaction solution was stirred at 100° C. for 5 hours under nitrogen protection. The reaction solution was diluted with water (15 mL), extracted with ethyl acetate (15 mL*2), the combined organic phase was washed with saturated brine (20 mL), dried over anhydrous sodium sulfate, filtered, and concentrated under reduced pressure to obtain a residue. The residue was purified by column chromatography (developing agent: petroleum ether:ethyl acetate=1:0 to 1:2) to obtain compound 33g (0.2 g, 441.01 μmol, 39.59% yield).

Step 6:

At 20-30° C., tris(triphenylphosphonium) rhodium chloride (116.29 mg, 125.7 μmol, 0.3 eq) was added to a solution of compound 33g (190 mg, 418.96 μmol, 1 eq) in ethanol (10 mL), and the reaction solution was reacted at 50° C. for 0.5 h under nitrogen atmosphere. The reaction solution was concentrated under reduced pressure and purified by preparative HPLC (column: Waters Xbridge 150*25 mm*5 μm; mobile phase: [ammonia-acetonitrile]; acetonitrile %: 27%-57%, 9 minutes) to obtain compound 33 (retention time 2.072 min) and 34 (retention time 2.427 min).

Compound 33 was purified by preparative HPLC (column: Phenomenex Synergi C18 150*25 mm*10 μm; mobile phase: [water (formic acid)-acetonitrile]; acetonitrile %: 9%-29%, 10 minutes)). LCMS (ESI) m/z: 456.1 (M+1)+, $^1$H NMR (400 MHz, DMSO-d6): δ=8.21 (s, 1H), 7.20 (s, 1H), 6.74 (t, J=56 Hz, 1H), 4.88 (m, 1H), 4.43-4.38 (m, 2H), 3.53 (m, 2H), 2.89 (s, 3H), 2.83-2.76 (m, 2H), 2.61-2.52 (m, 2H), 2.25 (m, 1H), 2.14-1.86 (m, 4H), 1.77-1.65 (m, 4H), 1.51-1.40 (m, 2H).

Compound 34 was purified by preparative HPLC (column: Phenomenex Synergi C18 150*25 mm*10 μm; mobile phase: [water (formic acid)-acetonitrile]; acetonitrile %: 36%-56%, 10 minutes)). LCMS (ESI) m/z: 456.2 (M+1)+, $^1$H NMR (400 MHz, DMSO-d6): δ=9.34 (s, 1H), 8.13 (br d, J=8.0 Hz, 1H), 7.91 (s, 1H), 7.06 (t, J=56 Hz, 1H), 4.88 (s, 1H), 4.10-3.98 (m, 2H), 3.58-3.55 (m, 2H), 2.97-2.90 (m, 5H), 2.09-2.05 (m, 2H), 1.93-1.61 (m, 8H), 1.25 (s, 3H).

Compounds in the Following Table were Synthesized by Referring to the Preparation Methods in the Above Embodiments:
| Compound No. | Structure | MS m/z: |
|---|---|---|
| Compound 35 | 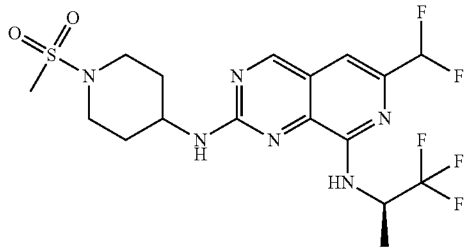 [SMILES: C[C@@H](Nc1nc(C(F)F)cc2cnc(NC3CCN(S(C)(=O)=O)CC3)nc12)C(F)(F)F] | 469.0 |
| Compound 36 | 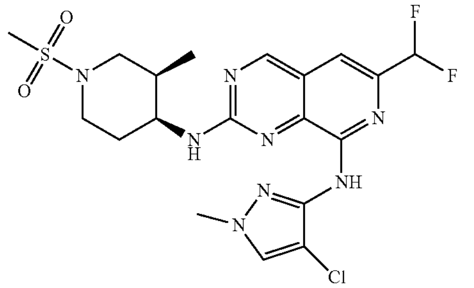 [SMILES: C[C@@H]1CN(S(C)(=O)=O)CC[C@@H]1Nc1ncc2cc(C(F)F)nc(Nc3nn(C)cc3Cl)c2n1] | 500.9 |
| Compound 37 | 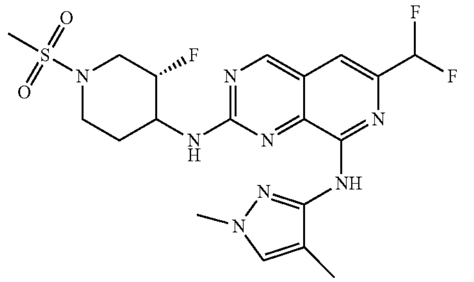 [SMILES: Cc1cn(C)nc1Nc1nc(C(F)F)cc2cnc(NC3CCN(S(C)(=O)=O)C[C@@H]3F)nc12] | 485.2 |
| Compound 38 | 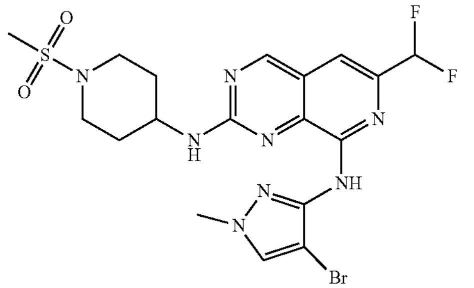 [SMILES: Cn1cc(Br)c(Nc2nc(C(F)F)cc3cnc(NC4CCN(S(C)(=O)=O)CC4)nc23)n1] | 530.9 |
| Compound 39 | 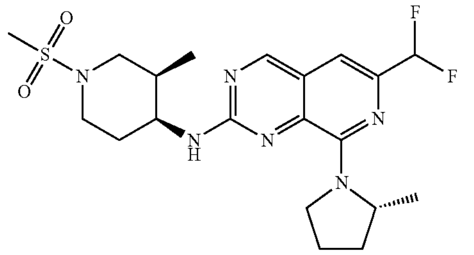 [SMILES: C[C@@H]1CN(S(C)(=O)=O)CC[C@@H]1Nc1ncc2cc(C(F)F)nc(N3CCC[C@H]3C)c2n1] | 455.2 |

-continued
| Compound No. | Structure | MS m/z: |
|---|---|---|
| Compound 40 | 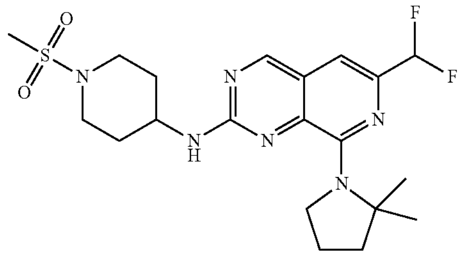 [SMILES: CC1(C)CCCN1c1nc(C(F)F)cc2cnc(NC3CCN(S(C)(=O)=O)CC3)nc12] | 455.3 |
| Compound 41 | 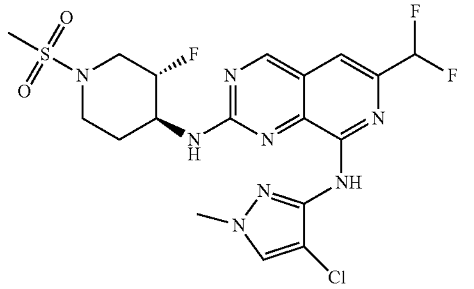 [SMILES: Cn1cc(Cl)c(Nc2nc(C(F)F)cc3cnc(N[C@H]4CCN(S(C)(=O)=O)C[C@@H]4F)nc23)n1] | 504.9 |
| Compound 42 | 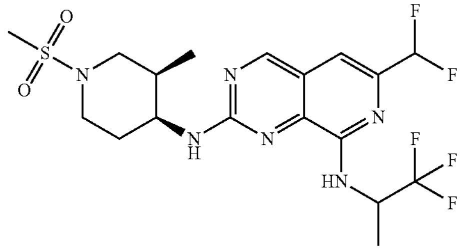 [SMILES: CC(Nc1nc(C(F)F)cc2cnc(N[C@H]3CCN(S(C)(=O)=O)C[C@H]3C)nc12)C(F)(F)F] | 483.0 |
| Compound 43 | 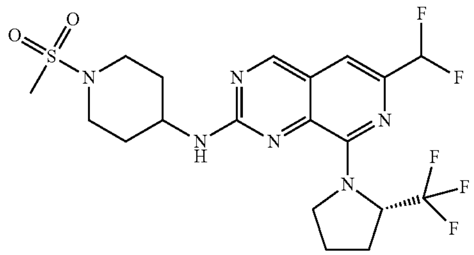 [SMILES: CS(=O)(=O)N1CCC(Nc2ncc3cc(C(F)F)nc(N4CCC[C@H]4C(F)(F)F)c3n2)CC1] | 495.2 |
| Compound 44 | 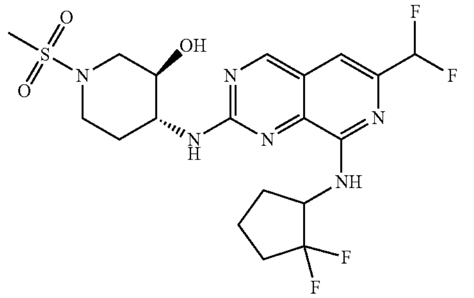 [SMILES: CS(=O)(=O)N1CC[C@@H](Nc2ncc3cc(C(F)F)nc(NC4CCCC4(F)F)c3n2)[C@H](O)C1] | 493.2 |

-continued
| Compound No. | Structure | MS m/z: |
|---|---|---|
| Compound 45 | 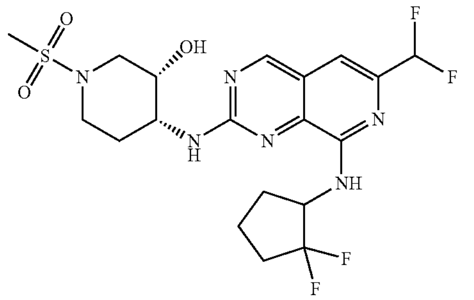 [SMILES: CS(=O)(=O)N1CC[C@@H](Nc2ncc3cc(C(F)F)nc(NC4CCCC4(F)F)c3n2)[C@@H](O)C1] | 493.2 |
| Compound 46 | 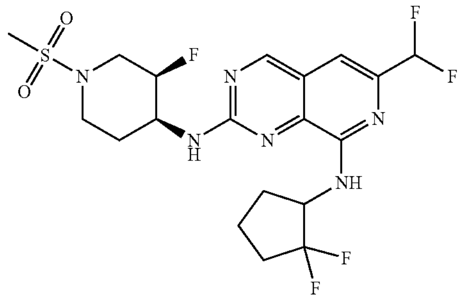 [SMILES: CS(=O)(=O)N1CC[C@H](Nc2ncc3cc(C(F)F)nc(NC4CCCC4(F)F)c3n2)[C@H](F)C1] | 495.2 |
| Compound 47 | 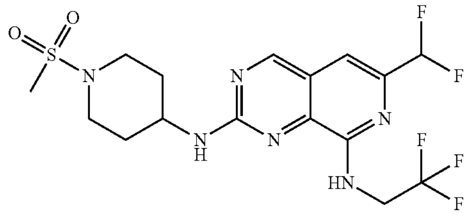 [SMILES: CS(=O)(=O)N1CCC(Nc2ncc3cc(C(F)F)nc(NCC(F)(F)F)c3n2)CC1] | 455.2 |
| Compound 48 | 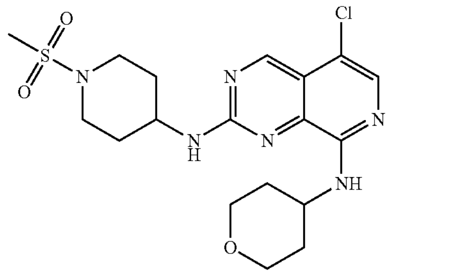 [SMILES: CS(=O)(=O)N1CCC(Nc2ncc3c(Cl)cnc(NC4CCOCC4)c3n2)CC1] | 441.1 |
| Compound 49 | 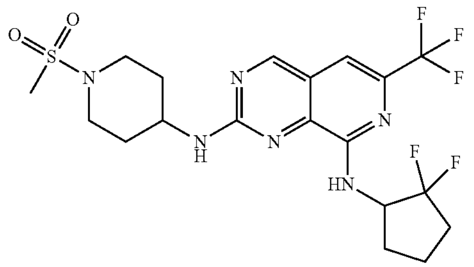 [SMILES: CS(=O)(=O)N1CCC(Nc2ncc3cc(C(F)(F)F)nc(NC4CCCC4(F)F)c3n2)CC1] | 495.4 |

-continued
| Compound No. | Structure | MS m/z: |
| --- | --- | --- |
| Compound 50 | 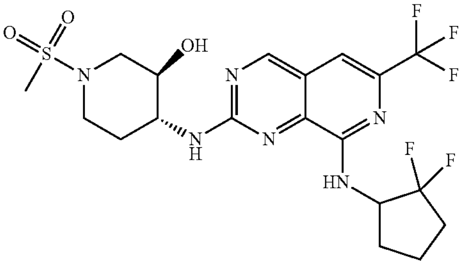 [SMILES: CS(=O)(=O)N1CC[C@@H](Nc2ncc3cc(C(F)(F)F)nc(NC4CCCC4(F)F)c3n2)[C@H](O)C1] | 511.0 |
| Compound 51 | 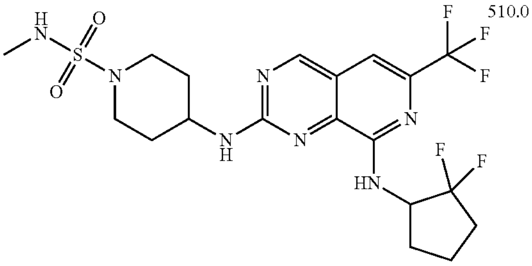 | 510.0 |
| Compound 52 | 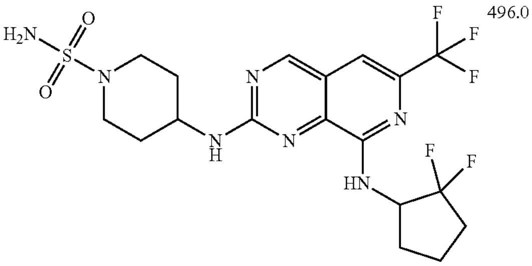 | 496.0 |
| Compound 53 | 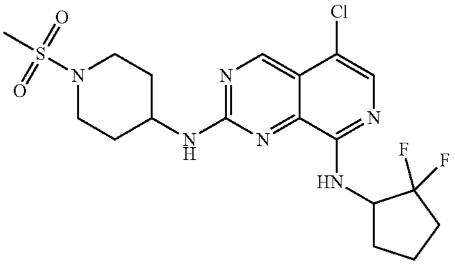 [SMILES: CS(=O)(=O)N1CCC(Nc2ncc3c(Cl)cnc(NC4CCCC4(F)F)c3n2)CC1] | 460.9 |
| Compound 54 | 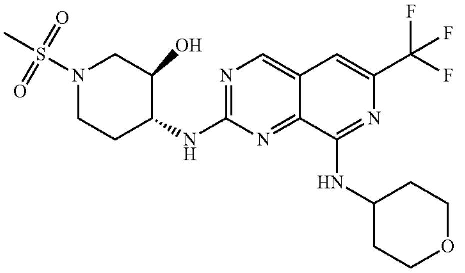 [SMILES: CS(=O)(=O)N1CC[C@@H](Nc2ncc3cc(C(F)(F)F)nc(NC4CCOCC4)c3n2)[C@H](O)C1] | 491.0 |

-continued
| Compound No. | Structure | MS m/z: |
|---|---|---|
| Compound 55 | 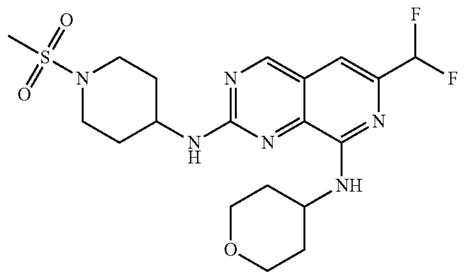 [SMILES: CS(=O)(=O)N1CCC(Nc2ncc3cc(C(F)F)nc(NC4CCOCC4)c3n2)CC1] | 457.1 |
| Compound 56 | 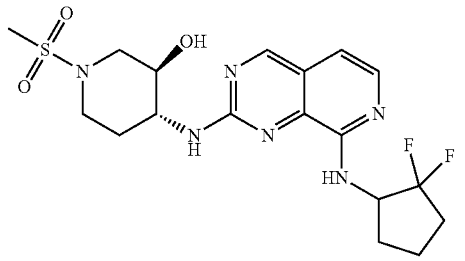 [SMILES: CS(=O)(=O)N1CC[C@@H](Nc2ncc3ccnc(NC4CCCC4(F)F)c3n2)[C@H](O)C1] | 443.1 |
| Compound 57 | 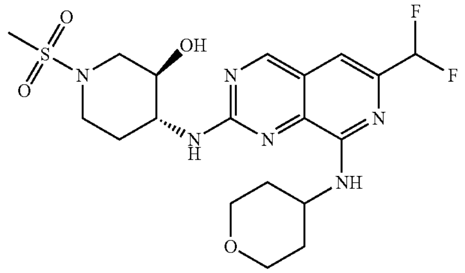 [SMILES: CS(=O)(=O)N1CC[C@@H](Nc2ncc3cc(C(F)F)nc(NC4CCOCC4)c3n2)[C@H](O)C1] | 473.0 |
| Compound 58 | 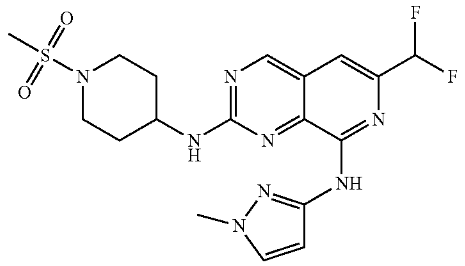 [SMILES: Cn1ccc(Nc2nc(C(F)F)cc3cnc(NC4CCN(S(C)(=O)=O)CC4)nc23)n1] | 453.0 |
| Compound 59 | 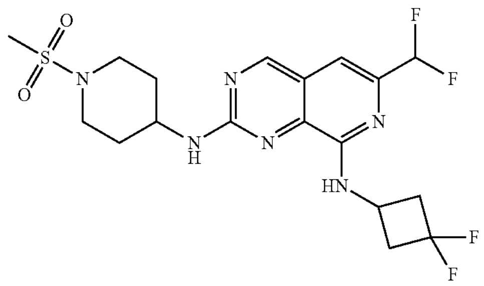 [SMILES: CS(=O)(=O)N1CCC(Nc2ncc3cc(C(F)F)nc(NC4CC(F)(F)C4)c3n2)CC1] | 463.1 |

-continued
| Compound No. | Structure | MS m/z: |
|---|---|---|
| Compound 60 | 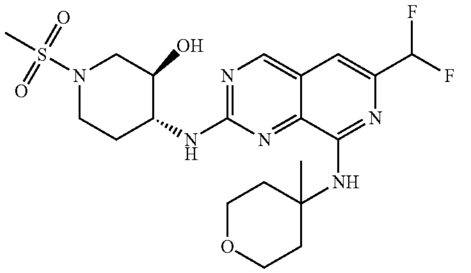 [SMILES: CC1(Nc2nc(C(F)F)cc3cnc(N[C@@H]4CCN(S(C)(=O)=O)C[C@H]4O)nc23)CCOCC1] | 487.0 |
| Compound 61 | 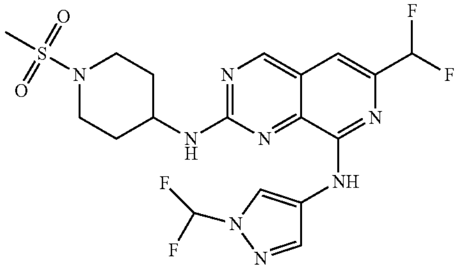 [SMILES: CS(=O)(=O)N1CCC(Nc2ncc3cc(C(F)F)nc(Nc4cnn(C(F)F)c4)c3n2)CC1] | 489.1 |
| Compound 62 | 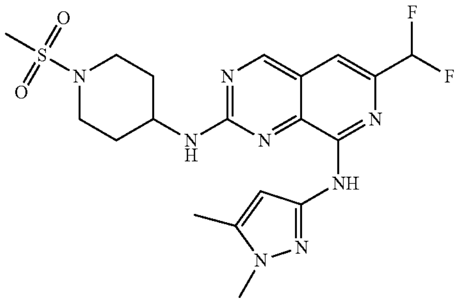 [SMILES: Cc1cc(Nc2nc(C(F)F)cc3cnc(NC4CCN(S(C)(=O)=O)CC4)nc23)nn1C] | 467.1 |
| Compound 63 | 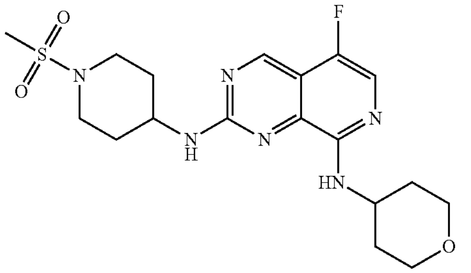 [SMILES: CS(=O)(=O)N1CCC(Nc2ncc3c(F)cnc(NC4CCOCC4)c3n2)CC1] | 425.2 |
| Compound 64 | 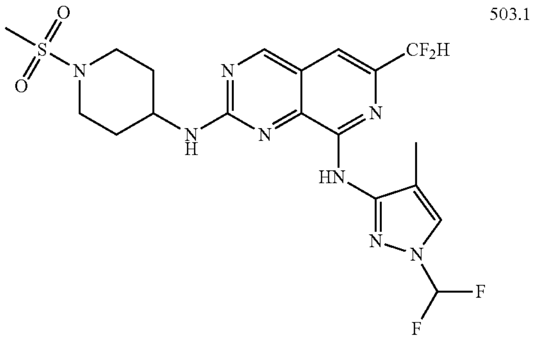 | 503.1 |

-continued

| Compound No. | Structure | MS m/z: |
|---|---|---|
| Compound 65 | 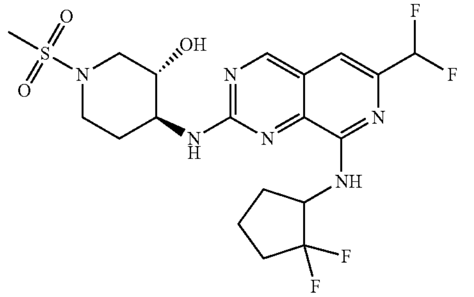 [SMILES: CS(=O)(=O)N1CC[C@H](Nc2ncc3cc(C(F)F)nc(NC4CCCC4(F)F)c3n2)[C@@H](O)C1] | 493.2 |

Experimental Embodiment 1. Enzyme Activity Test

Experimental Materials:

CDK1/CyclinB1 Kinase, CDK2/CyclinA2 Kinase, CDK2/CyclinE1 Kinase, CDK4/CyclinD1 Kinase, CDK6/CyclinD1 Kinase, CDK7/CyclinH/MAT1 Kinase, CDK9/CyclinT1 Kinase, LANCE Ultra ULight™-4E-BP-1 (Thr37146) Peptide EU-ANTI-P-4EBP1 (THR37/46), Nivo multiple label analyzer.

Experimental Methods:

CDK1/CyclinB1 Enzyme Reaction System

Enzymes, substrates, ATP, and inhibitors were diluted by kinase buffer in the kit. The compounds to be tested were diluted 5-fold with a multi-channel pipette to the eighth concentration, that is, from 50 μM to 0.65 nM, the concentration of DMSO was 5%, and a double-hole experiment was set up. 1 μL of each concentration gradient of inhibitors, 2 μL of CDK1/CyclinB1 enzyme (12.5 ng), 2 μL mixture of substrate and ATP (25 μM adenosine triphosphate, 0.2 μg/μL substrate) were added to the microplates, and the final concentration gradient of the compound was 10 μM to 0.13 nM. The reaction system was reacted at 25° C. for 120 minutes. After the reaction, 5 μL of ADP-Glo reagent was added to each well, the reaction was carried out at 25° C. for 40 minutes, after the reaction was completed, 10 μL of kinase detection reagent was added to each well, the reaction was carried out at 25° C. for 30 minutes, the multiple label analyzer was used to read the chemiluminescence with an integration time of 0.5 seconds.

CDK2/CyclinA2 Enzyme Reaction System

Enzymes, substrates, ATP, and inhibitors were diluted by kinase buffer in the kit. The compounds to be tested were diluted 5-fold with a multi-channel pipette to the eighth concentration, that is, from 50 μM to 0.65 nM, the concentration of DMSO was 5%, and a double-hole experiment was set up. 1 μL of each concentration gradient of inhibitors, 2 μL of CDK2/CyclinA2 enzyme (1.6 ng), 2 μL mixture of substrate and ATP (50 μM ATP, 0.1 μg/μL substrate) were added to the microplates, and the final concentration gradient of the compound was 10 μM to 0.13 nM. The reaction system was reacted at 25° C. for 60 minutes. After the reaction, 5 μL of ADP-Glo reagent was added to each well, the reaction was carried out at 25° C. for 40 minutes, after the reaction was completed, 10 μL of kinase detection reagent was added to each well, the reaction was carried out at 25° C. for 30 minutes, the multiple label analyzer was used to read the chemiluminescence with an integration time of 0.5 seconds CDK2/CyclinE1 Enzyme Reaction System Enzymes, substrates, ATP, and inhibitors were diluted by kinase buffer in the kit. The compounds to be tested were diluted 5-fold with a multi-channel pipette to the eighth concentration, that is, from 50 μM to 0.65 nM, the concentration of DMSO was 5%, and a double-hole experiment was set up. 1 μL of each concentration gradient of inhibitors, 2 μL of CDK2/CyclinE1 enzyme (2 ng), 2 μL mixture of substrate and ATP (150 μM ATP, 0.1 μg/μL substrate) were added to the microplates, and the final concentration gradient of the compound was 10 μM to 0.13 nM. The reaction system was reacted at 25° C. for 60 minutes. After the reaction, 5 μL of ADP-Glo reagent was added to each well, the reaction was carried out at 25° C. for 40 minutes, after the reaction was completed, 10 μL of kinase detection reagent was added to each well, the reaction was carried out at 25° C. for 30 minutes, the multiple label analyzer was used to read the chemiluminescence with an integration time of 0.5 seconds.

CDK4/CyclinD1 Enzyme Reaction System

Preparation of Kinase Buffer:

The composition of the buffer: 50 mM of hydroxyethylpiperazine ethanesulfonic acid solution at pH 7.5, 1 mM of ethylenediaminetetraacetic acid, 10 mM of magnesium chloride, 0.01% Brij-35, and 2 mM of dithiothreitol.

Enzymes, substrate LANCE Ultra ULight™-4E-BP-1 (Thr37146) Peptide, ATP, and inhibitors were diluted by kinase buffer.

The compounds to be tested were diluted 5-fold with a multi-channel pipette to the eighth concentration, that is, from 40 μM to 0.512 nM, the concentration of DMSO was 4%, and a double-hole experiment was set up. 2.5 μL of each concentration gradient of inhibitors and 5 μL of CDK4/CyclinD1 enzyme (0.5 ng) were added to the microplates, after the reaction was carried out at 25° C. for 60 minutes, 2.5 μL mixture of substrate and ATP (350 μM ATP, 12.5 nM substance) were added, and the final concentration gradient of the compound was 10 μM to 0.128 nM. The reaction system was reacted at 25° C. for 120 minutes. After the reaction, 5 μL mixture of EDTA and 2× LANCE™ Detection Buffer (1:1) were added to each well, the reaction was carried out at 25° C. for 5 minutes, after the reaction was completed, 5 μL of LANCE Ultra Eu-anti-P-4E-BP1 (Thr37MS) (4 nM) was added to each well, the reaction was carried out at 25° C. for 60 minutes, the reaction signal was detected by Nivo instrument according to the principle of time-resolved fluorescence resonance energy transfer.

CDK6/CyclinD1 Enzyme Reaction System

Preparation of Kinase Buffer:

The composition of the buffer: 50 mM of hydroxyethylpiperazine ethanesulfonic acid solution at pH 7.5, 1 mM of ethylenediaminetetraacetic acid, 10 mM of magnesium chloride, 0.01% Brij-35, and 2 mM of dithiothreitol.

Enzymes, substrate LANCE Ultra ULight™-4E-BP-1 (Thr37146) Peptide, ATP, and inhibitors were diluted by kinase buffer.

The compounds to be tested were diluted 5-fold with a multi-channel pipette to the eighth concentration, that is, from 40 μM to 0.512 nM, the concentration of DMSO was 4%, and a double-hole experiment was set up. 2.5 μL of each concentration gradient of inhibitors and 5 μL of CDK6/CyclinD1 enzyme (0.5 ng) were added to the microplates, after the reaction was carried out at 25° C. for 60 minutes, 2.5 μL mixture of substrate and ATP (250 μM ATP, 12.5 nM substance) were added, and the final concentration gradient of the compound was 10 μM to 0.128 nM. The reaction system was reacted at 25° C. for 120 minutes. After the reaction, 5 μL mixture of EDTA and 2× LANCE™ Detection Buffer (1:1) were added to each well, the reaction was carried out at 25° C. for 5 minutes, after the reaction was completed, 5 μL of LANCE Ultra Eu-anti-P-4E-BP1 (Thr37MS) (4 nM) was added to each well, the reaction was carried out at 25° C. for 60 minutes, the reaction signal was detected by Nivo instrument according to the principle of time-resolved fluorescence resonance energy transfer.

CDK7/CyclinH/MAT1 Enzyme Reaction System

Enzymes, substrates (MBP), ATP, and inhibitors were diluted by kinase buffer in the kit. The compounds to be tested were diluted 5-fold with a multi-channel pipette to the eighth concentration, that is, from 50 μM to 0.65 nM, the concentration of DMSO was 5%, and a double-hole experiment was set up. 1 μL of each concentration gradient of inhibitors, 2 μL of CDK7/CyclinH/MAT1 enzyme (20 ng), 2 μL mixture of substrate and ATP (10 μM ATP, 0.1 μg/μL substrate) were added to the microplates, and the final concentration gradient of the compound was 10 μM to 0.13 nM. The reaction system was reacted at 25° C. for 120 minutes. After the reaction, 5 μL of ADP-Glo reagent was added to each well, the reaction was carried out at 25° C. for 40 minutes, after the reaction was completed, 10 μL of kinase detection reagent was added to each well, the reaction was carried out at 25° C. for 30 minutes, the multiple label analyzer was used to read the chemiluminescence with an integration time of 0.5 seconds.

CDK9/CyclinT1 Enzyme Reaction System

Enzymes, substrates, ATP, and inhibitors were diluted by kinase buffer in the kit. The compounds to be tested were diluted 5-fold with a multi-channel pipette to the eighth concentration, that is, from 50 μM to 0.65 nM, the concentration of DMSO was 5%, and a double-hole experiment was set up. 1 μL of each concentration gradient of inhibitors, 2 μL of CDK9/CyclinT1 enzyme (4 ng), 2 μL mixture of substrate and ATP (100 μM ATP, 0.2 μg/μL substrate) were added to the microplates, and the final concentration gradient of the compound was 10 μM to 0.13 nM. The reaction system was reacted at 25° C. for 120 minutes. After the reaction, 5 μL of ADP-Glo reagent was added to each well, the reaction was carried out at 25° C. for 40 minutes, after the reaction was completed, 10 μL of kinase detection reagent was added to each well, the reaction was carried out at 25° C. for 30 minutes, the multiple label analyzer was used to read the chemiluminescence with an integration time of 0.5 seconds.

Data Analysis:

The equation (Sample−Min)/(Max−Min)*100% was used to convert the raw data into inhibition rate, and the value of $IC_{50}$ can be obtained by curve fitting with four parameters (obtained by log (inhibitor) vs. response-Variable slope mode in GraphPad Prism). The enzymatic inhibitory activity of the compounds of the present disclosure on CDK1/CyclinB1, CDK2/CyclinA2, CDK2/CyclinE1, CDK4/CyclinD1, CDK6/CyclinD1, CDK7/CyclinH/MAT1, CDK9/CyclinT1 was provided in Table 1.

TABLE 1

Test results of enzyme activity

| Test compound | CDK1/ Cyclin B $IC_{50}$ (nM) | CDK2/ Cyclin A2 $IC_{50}$ (nM) | CDK2/ Cyclin E1 $IC_{50}$ (nM) | CDK4/ Cyclin D1 $IC_{50}$ (nM) | CDK6/ Cyclin D1 $IC_{50}$ (nM) | CDK7/ Cyclin H $IC_{50}$ (nM) | CDK 9/ Cyclin T1 $IC_{50}$ (nM) |
|---|---|---|---|---|---|---|---|
| Compound 1 | 2.72 | 0.56 | 1.67 | 3.90 | 2.28 | / | / |
| Compound 4 | / | 0.27 | / | 1.50 | 1.49 | / | / |
| Compound 6 | / | 0.52 | / | 1.08 | 1.56 | / | / |
| Compound 8 | 6.77 | 0.73 | 3.92 | 1.23 | 0.81 | 41 | 89 |
| Compound 11 | 12.7 | 1.40 | 6.58 | 73.7 | 28.3 | 227 | 303 |
| Compound 14 | / | 1.25 | 4.15 | 2.59 | 1.69 | / | / |
| Compound 18 | / | / | 4.72 | 1.56 | 1.32 | / | / |
| Compound 19 | / | / | 4.73 | 4.26 | 1.15 | / | 178 |
| Compound 20 | / | / | 1.33 | 0.82 | 0.56 | / | 105.7 |
| Compound 21 | 8.48 | / | 4.32 | 0.46 | 0.34 | 32.87 | 14.97 |
| Compound 22 | 8.86 | / | 3.52 | 0.5 | 1.36 | 80.51 | 36.87 |
| Compound 23 | / | / | 4.27 | 15.43 | 7.44 | / | 214.1 |
| Compound 24 | / | / | 3.6 | 19.42 | 10.79 | / | / |
| Compound 25 | / | / | 4.02 | / | 0.46 | / | / |

Note:
"/" mean not tested

Experimental Conclusion:

The compounds of the present disclosure had significant inhibitory activity on CDK2 kinase, certain inhibitory activity on CDK4 and CDK6 kinases, weak inhibitory activity on CDK1 kinase, and certain selectivity on CDK7 and CDK9 kinases.

Experimental Embodiment 2: Cell Activity Test

Experimental Materials:

1) Reagent Consumables

| Reagent | Brand | Code Number | Batch |
|---|---|---|---|
| RPIM1640 culture medium | ATCC | 22400-089 | 2193294 |
| fetal bovine serum | ExCell Bio | FSP500 | 111323 |
| Double antibiotic (Penicillin, Streptomycin) | HyClone | SV30010 | J200049 |
| Phosphate buffer | Corning | 21031CVC | 21031031 |
| 0.25% trypsin | Gibco | 25200072 | 2185855 |
| CellTiter Glo buffer | Promega | G756B | 0000433295 |
| CellTiter Glo substrate | Promega | G755B | 0000440444 |
| 96-well Plate | Greiner | 781091 | E19113Q3 |

2) Experimental Instruments:

| Instrument | Manufacturer | Model |
|---|---|---|
| Biological safety cabin | AIRTECH | BSC-1304IIA2 |
| Carbon dioxide incubator | Thermo | 311 |
| Cell counter | BECKMAN | Vi-cellXR |
| Enzyme marker | PerkinElmer | Envision |

3) Cell Information

| Cell name | Tumor type | Cell type | Culture medium | 384-well plate inoculum number | Source | Code number |
|---|---|---|---|---|---|---|
| OVCAR-3 | Ovarian Cancer | Adherent | RPMI-1640 + 10% FBS | 1000 | ATCC | HTB-161 |
| MCF-7-PR | Breast cancer | Adherent | RPMI-1640 + 10% FBS | 1000 | WuXi | NA |

Experimental Methods:

1) Cell Culture and Passage (1) Culture medium see table below (2) Cells were isolated and passaged every 3-4 days 2) Day 1: Laying Cell Plates (1) Phosphate buffered saline (PBS), trypsin, and culture medium used in the cell passage process were pre-heated into a 37° C. water bath.

(2) T75 cell culture flask was taken out from a 37° C. 5% $CO_2$ incubator, and the old culture medium in the culture flask was pipetted out with a pipette.

(3) 5 mL of phosphate buffered saline was pipetted into the culture flask to rinse the cells, then liquid was discarded.

(4) 1 mL trypsin was pipetted into the culture flask, and put into the incubator after shaken.

(5) After 1 minute, the culture flask was taken out, after the cells have been separated, 5 mL of medium was pipetted into the culture flask and repeatedly pipetted several times, and the cell suspension was transferred to a 50 mL centrifuge tube.

(6) 0.7 mL of cell suspension was pipetted into the counting cup, the cells were counted on ViCell XR, and the cell suspension was diluted separately with culture medium to the required cell concentration for laying cell plates: 1000/30 ul.

(7) Microplates (2 plates) were required, 100 uL of phosphate buffered saline was added to the peripheral wells of the 384-well plate, 30 uL of cell suspension was added to the other wells, and the cell plate was placed into incubator for culture.

3) Administration (1) Compound preparation: the stock solution of the compound to be tested was 10 mM.

(2) The compound to be tested was diluted 3 times with DMSO for 10 gradients.

(2) The compound to be tested was diluted with culture medium, and the highest final concentration was 10 μM.

(3) The cell plate was taken out from the incubator.

(4) 10 μL of the compound was pipetted into the 384-well plate, and then the cell plate was placed back into the incubator for culture.

4) Adding CTG and Reading the Plate (1) After 7 days of culture, 50 ul CellTiter Glo was added to the cell plate, shaken for 10 minutes in the dark, and left at room temperature for 5 minutes.

(2) The plate was read on Envision with the program: US LUM 384 (CPS). The experiment was originally stored in the personal disk:

Y:\RAW DATA\FL353\CTG-OVCAR3-MCF-7-PR

Data Analysis:

1. The mean and standard deviation of 0% inhibition (DMSO row, ZPE) and 100% inhibition (PBS row, HPE) were calculated;
2. Inhibition rate (%)=(1−(sample value-average value of 100% inhibition)/(average value of 0% inhibition-average value of 100% inhibition))*100;
3. The curve was fitted by GraphPad 8.0 software;

TABLE 2

Anti-proliferation activity ($IC_{50}$) of compounds in the embodiment of present disclosure on cells

| Test compound | OVCAR-3 (nM) | MCF-7-PR |
|---|---|---|
| 18 | 17 | 11 |
| 19 | 29 | 98 |
| 20 | 12 | 53 |
| 21 | 15 | 9 |
| 22 | 44 | 50 |
| 25 | <1 | <1 |

Experimental conclusion: The compounds of the present disclosure exhibited significant inhibitory activity on the proliferation of OVCAR-3 and MCF-7-PR cells.

Experimental Embodiment 3: Pharmacokinetic Evaluation of the Compounds of the Present Disclosure Experimental Scheme of Compounds 18, 19 and 20

Experimental Animals

The healthy adult male CD-1 (ICR) mice used in this study were purchased from Pinghu Weitong Lihua Experimental Animal Technology Co., Ltd.

Preparation of Drugs

Preparation of administration solution for oral administration group 0.300 mL of the stock solution was measured and vortexed for 2 minutes to obtain a homogeneous suspension at a concentration of 1 mg/mL, and the administration vehicle was 1% HPMC in water.

Administration

Two male CD-1 (ICR) mice were given 5 mg/kg of the compound to be tested by intragastric administration.

Sample Collection

The blood of two animals was collected at each time point by serial blood collection. 30 μL of whole blood was collected respectively at 0.25, 0.5, 1, 2, 4, 8, and 24 hours after administration. The whole blood was placed in an anticoagulant tube, centrifuged at 3200 g for 10 minutes at 4° C., plasma was prepared and stored at −60° C. or lower. The drug concentration in plasma was determined by LC/MS-MS.

TABLE 3

The pharmacokinetic results of the compounds of the embodiments of the present disclosure

| Compound (oral: 5 mg/kg) | Pharmacokinetic parameters Oral exposure AUC0-t (nM h) |
|---|---|
| 18 | 2365 |
| 19 | 3143 |
| 20 | 2746 |

Experimental conclusion: the compounds of the present disclosure had a high exposure in mice and exhibited good pharmacokinetic properties.

Experimental Example 4: In Vivo Efficacy Study

In vivo efficacy study of human ovarian cancer OVCAR-3 cells subcutaneous xenograft tumor BALB/c nude mouse model Experimental Operation:

Cell culture: Human ovarian cancer OVCAR-3 cells were monolayer cultured in vitro, the culture conditions were 10% fetal bovine serum, 100 U/mL Penicillin and 100 μg/mL Streptomycin were added in RPMI 1640 medium, cultured at 37° C. 5% $CO_2$ incubator. Conventional digestion with trypsin-EDTA was performed for passage. When the cell saturation was 80%/90% and the number reached the required level, the cells were collected, counted, and inoculated.

Animals: BALB/c nude mice, female, 6-8 weeks old, weighed 18-22 grams. A total of 95 (42+ additional 53) animals were needed, provided by the Experimental Animal Management Department of Shanghai Institute of Family Planning Sciences (formerly Shanghai Sipulbichem).

Tumor inoculation: 0.2 mL ($1\times10^7$) OVCAR-3 cells (with matrix glue, volume ratio of 1:1) were subcutaneously inoculated on the right back of each mouse, and the mice were grouped administrated when the average tumor volume reached about 150 $mm^3$.

Dosage and frequency of administration: Day 0 to Day 7, 10 mg/kg; Day 7 to Day 14, 10 mg/kg; Day 14 to Day 21, 30 mg/kg;

Experimental index: The experimental index was used to examine whether tumor growth was inhibited, delayed or cured. Tumor diameters were measured with vernier calipers twice a week. The calculation formula of tumor volume was: $V=0.5a\times b^2$, wherein a and b represented the long and short diameters of the tumor, respectively.

Experimental results were shown in Table 4.

TABLE 4

In vivo efficacy test results of compounds in the embodiment of present disclosure on OVCAR-3

| Compound | Administration dose (mg/kg) | Tumor volume ($mm^3$) (Day 0) | (Day 7) | (Day 14) | (Day 21) |
|---|---|---|---|---|---|
| Blank control | 0 | 15 | 264 | 515 | 835 |
| Compound 18 | 10 mg/kg from day 0 to day 7; 10 mg/kg from day 7 to day 14; 30 mg/kg from day 14 to day 21. | 151 | 233 | 393 | 529 |
| Compound 19 | 10 mg/kg from day 0 to day 7; 10 mg/kg from day 7 to day 14; 30 mg/kg from day 14 to day 21. | 151 | 246 | 375 | 392 |
| Compound 20 | 10 mg/kg from day 0 to day 7; 10 mg/kg from day 7 to day 14; 30 mg/kg from day 14 to day 21. | 151 | 236 | 338 | 363 |
| Compound 22 | 10 mg/kg from day 0 to day 7; 10 mg/kg from day 7 to day 14; 30 mg/kg from day 14 to day 21. | 151 | 243 | 319 | 238 |
| Compound 23 | 10 mg/kg from day 0 to day 7; 10 mg/kg from day 7 to day 14; 30 mg/kg from day 14 to day 21. | 151 | 259 | 408 | 602 |
| Compound 25 | 10 mg/kg from day 0 to day 7; 10 mg/kg from day 7 to day 14; 30 mg/kg from day 14 to day 21. | 151 | 226 | 371 | 611 |

EXPERIMENTAL CONCLUSION

In vivo efficacy study of human ovarian cancer OVCAR-3 cells subcutaneous xenograft tumor BALB/c nude mouse model, compounds of the present disclosure were well tolerated by animals and exhibited good drug efficacy and safety.

The invention claimed is:

1. A compound represented by formula (III) or a pharmaceutically acceptable salt thereof, (III)

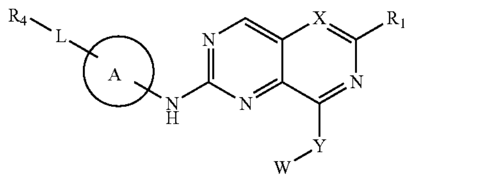

wherein, ring A is 3-10 membered heterocycloalkyl, and the 3-10 membered heterocycloalkyl is optionally substituted by 1, 2, or 3 $R_a$;

W is selected from and

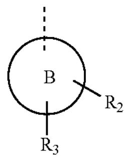

$R_5$;

ring B is selected from $C_{3-8}$ cycloalkyl, 5-6 membered heteroaryl and 3-10 membered heterocycloalkyl, and the $C_{3-8}$ cycloalkyl, 5-6 membered heteroaryl and 3-10 membered heterocycloalkyl are independently and optionally substituted by 1, 2, or 3 Rb;

X is $C(R_c)$;

Y is selected from single bond, —NH— and —O—; -L is $—S(═O)_2—$;

$R_1$ is selected from H, halogen, $C_{1-3}$ alkyl, $C_{1-3}$ alkoxy and —C(═O)—$C_{1-3}$ alkyl, and the $C_{1-3}$ alkyl, $C_{1-3}$ alkoxy and —C(═O)—$C_{1-3}$ alkyl are independently and optionally substituted by 1, 2, or 3 $R_d$;

$R_2$ and $R_3$ are independently selected from H, halogen, OH, CN, $NH_2$ and $C_{1-8}$ alkyl, and the $C_{1-8}$ alkyl is optionally substituted by 1, 2, or 3 Re;

$R_4$ is selected from $NH_2$, —NH—$C_{1-6}$ alkyl, —NH(CN), —NH(OH), $C_{1-6}$ alkyl, —N(CN)—$C_{1-6}$ alkyl and —N(OH)—$C_{1-6}$ alkyl, and the—NH—$C_{1-6}$ alkyl, $C_{1-6}$ alkyl, —N(CN)—$C_{1-6}$ alkyl and —N(OH)—$C_{1-6}$ alkyl are independently and optionally substituted by 1, 2, or 3 Rf;

$R_5$ is selected from $C_{1-3}$ alkyl optionally substituted by 1, 2, or 3 $R_g$;

$R_c$ is selected from H, F, Cl, Br, I and $CH_3$;

$R_a$ is independently selected from F, Cl, Br, I, $CH_3$, $OCH_3$, OH, $NH_2$, CN, COOH;

$R_a$, $R_b$, $R_e$ and $R_f$ are independently selected from F, Cl, Br, I, OH, CN, $CH_3$, $CH_3CH_2$, $CH_3CH_2CH_2$, $CH(CH_3)_2$, $OCH_3$, $OCF_3$, $CHF_2$, $CH_2F$ and $NH_2$;

$R_g$ is independently selected from F, Cl, Br, I, OH, CN and $CH_3$;

the 3-10 membered heterocycloalkyl, 5-6 membered heteroaryl and 3-10 membered heterocycloalkenyl and 5-6 membered heteroaryl are respectively containing 1, 2, or 3 heteroatoms or heteroatomic groups independently selected from—NH—, —O—, —S-and N.

2. The compound or the pharmaceutically acceptable salt thereof as defined in claim 1, wherein, $R_1$ is selected from H, CI, $CHF_2$, $CF_3$ and $CH_3$;

or, $R_2$ and $R_3$ are independently selected from H, F, CI, OH and $CH_3$.

3. The compound or the pharmaceutically acceptable salt thereof as defined in claim 1, wherein, $R_4$ is selected from $CH_3$, $NH_2$ and $—NH(CH_3)$.

4. The compound or the pharmaceutically acceptable salt thereof as defined in claim 1, wherein, X is selected from CH, CF, CCl, CBr and $CCH_3$.

5. The compound or the pharmaceutically acceptable salt thereof as defined in claim 1, wherein, ring A is selected from 5-6 membered heterocycloalkyl, and the 5-6 membered heterocycloalkyl is optionally substituted by 1, 2, or 3 $R_a$.

6. The compound or the pharmaceutically acceptable salt thereof as defined in claim 5, wherein, ring A is piperidinyl, and the piperidinyl is optionally substituted by 1, 2, or 3 $R_a$.

7. The compound or the pharmaceutically acceptable salt thereof as defined in claim 6, wherein, ring A is selected from

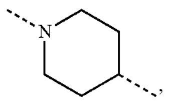,
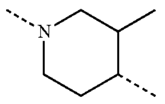
and
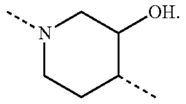

8. The compound or the pharmaceutically acceptable salt thereof as defined in claim 1, wherein, ring B is selected from $C_{5-6}$ cycloalkyl, 5-6 membered heterocycloalkyl and 5-6 membered heteroaryl, and the $C_{5-6}$ cycloalkyl, 5-6 membered heterocycloalkyl and 5-6 membered heteroaryl are independently and optionally substituted by 1, 2, or 3 $R_b$.

9. The compound or the pharmaceutically acceptable salt thereof as defined in claim 8, wherein, ring B is selected from cyclopentyl, pyrrolidinyl and pyrazolyl, and the cyclopentyl, pyrrolidinyl and pyrazolyl are independently and optionally substituted by 1, 2, or 3 $R_b$.

10. The compound or the pharmaceutically acceptable salt thereof as defined in claim 9, wherein, structural unit

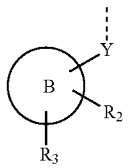

is selected from

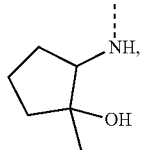

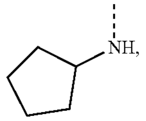

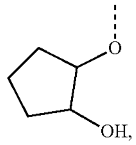

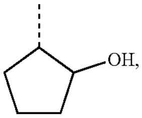

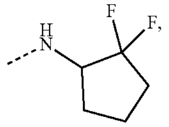

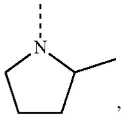

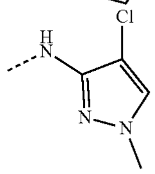

and

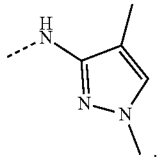

11. The compound or the pharmaceutically acceptable salt thereof as defined in claim 1, wherein, structural unit —Y—W is selected from

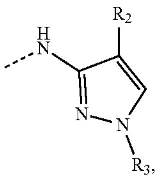

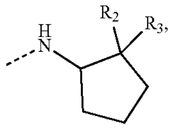

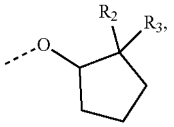

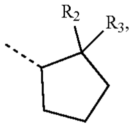

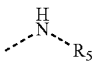

and

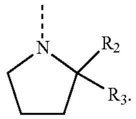

12. The compound or the pharmaceutically acceptable salt thereof as defined in claim 11, wherein, structural unit —Y—W is selected from

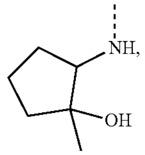

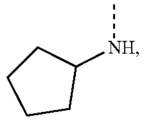

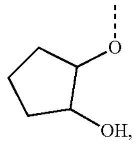

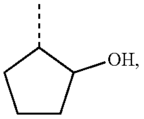

-continued

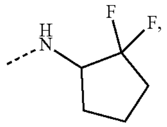

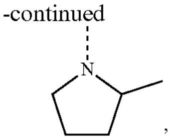

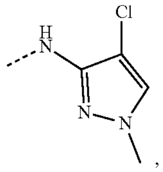

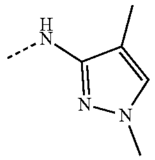

and

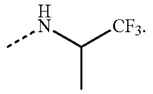

13. The compound or the pharmaceutically acceptable salt thereof as defined in claim 1, wherein, structural unit

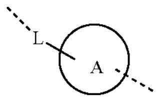

is selected from

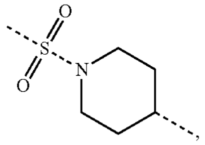

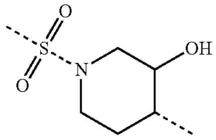

and

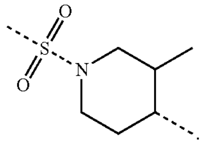

14. The compound or the pharmaceutically acceptable salt thereof as defined in claim 1, wherein, $R_5$ is

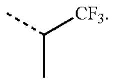

15. The compound or the pharmaceutically acceptable salt thereof as defined in claim 1, wherein, the compound is selected from (I-2)

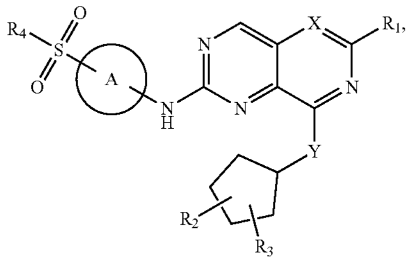

-continued
(III-1)
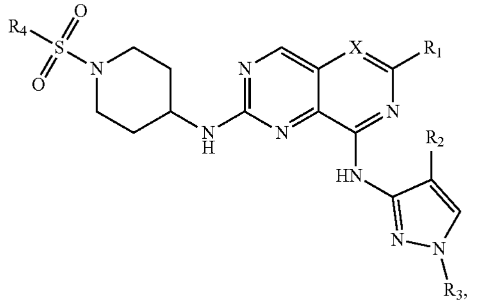
(III-2)
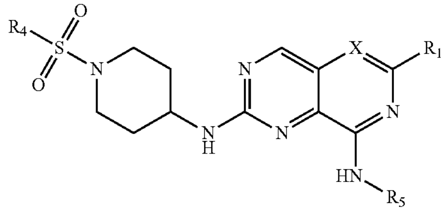
and
(III-3)
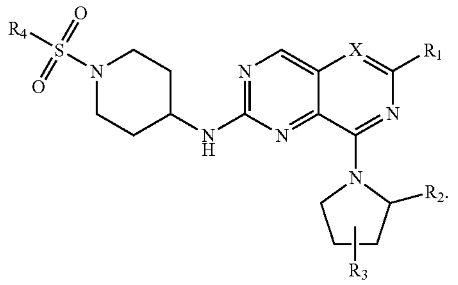
16. The compound or the pharmaceutically acceptable salt thereof as defined in claim 15, wherein, the compound is selected from
(III-4)
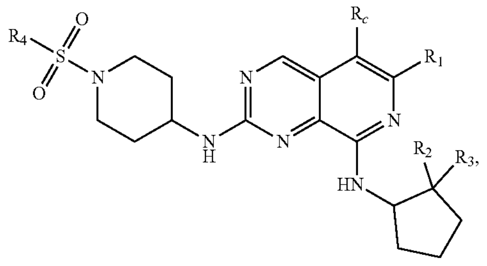
(III-5)
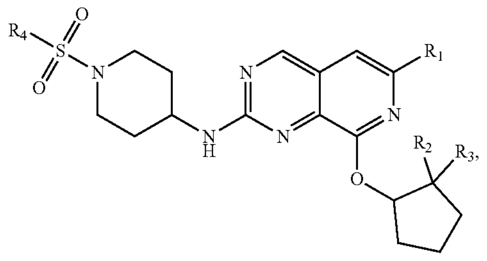
-continued
(III-6)
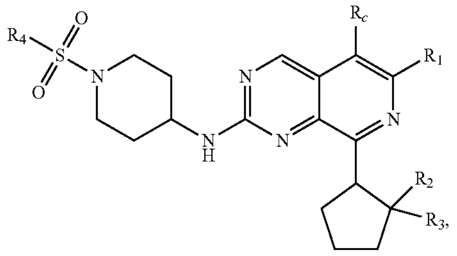
(III-7)
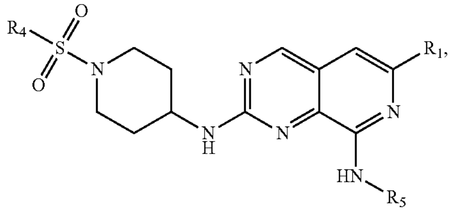
(III-8)
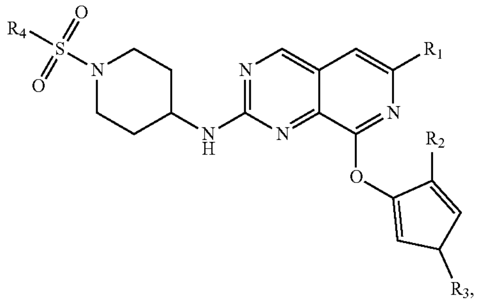
and
(III-9)
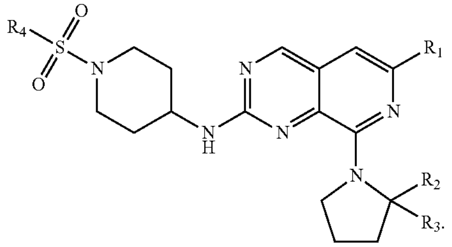
17. A compound or a pharmaceutically acceptable salt thereof, wherein, the compound is selected from
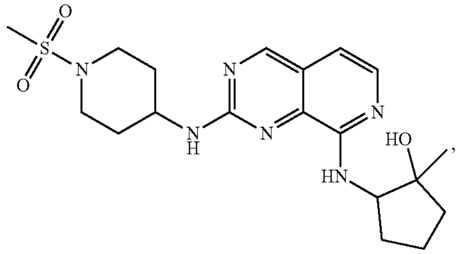

-continued
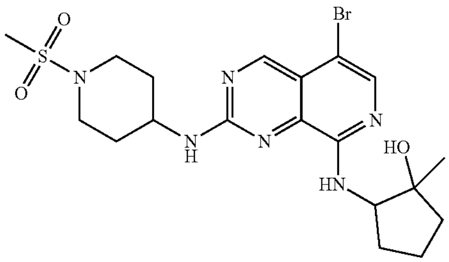
,
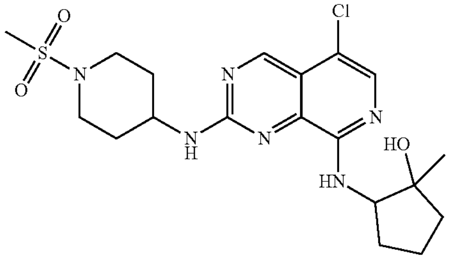
,
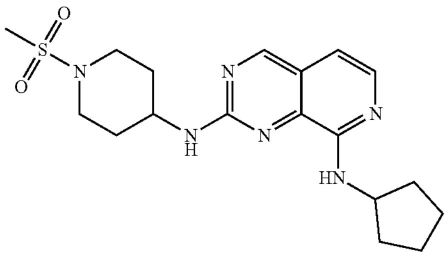
,
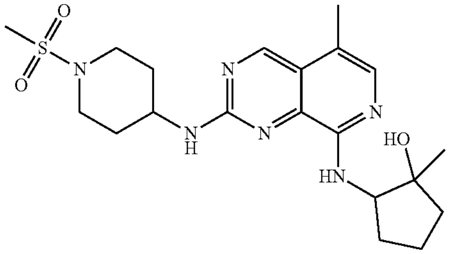
,
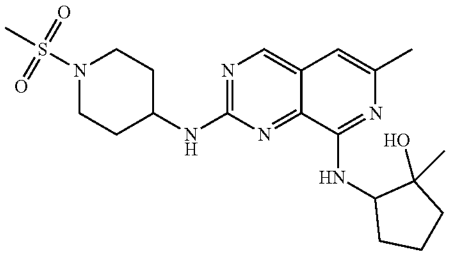
,
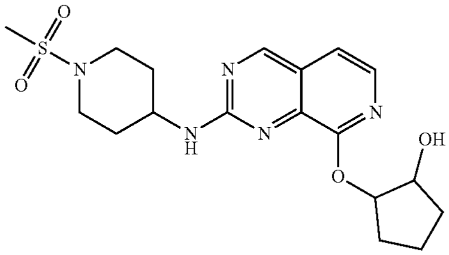
,
-continued
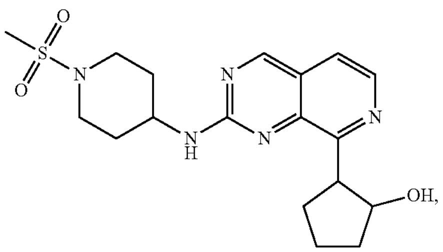
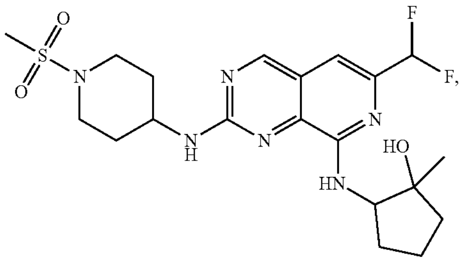
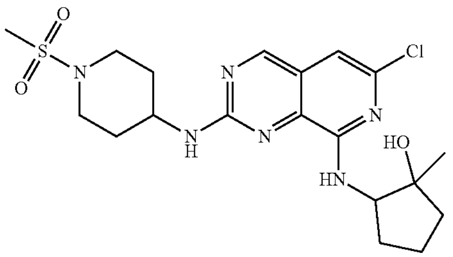
,
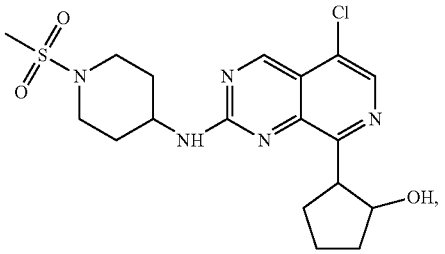
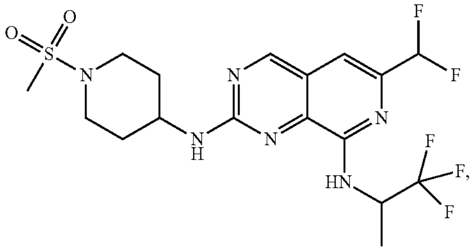
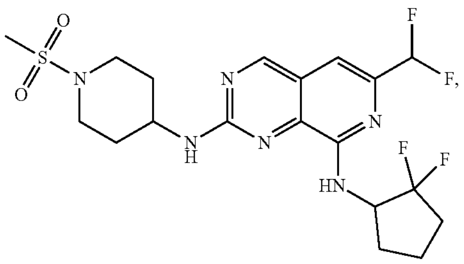

-continued
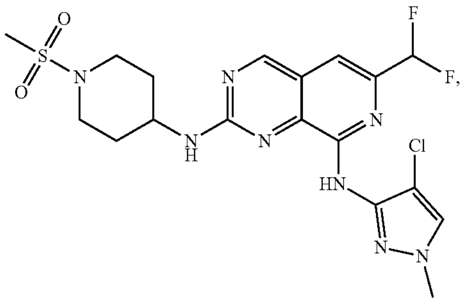
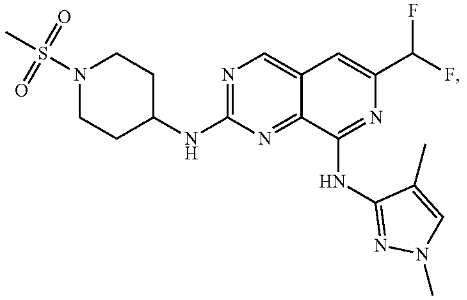
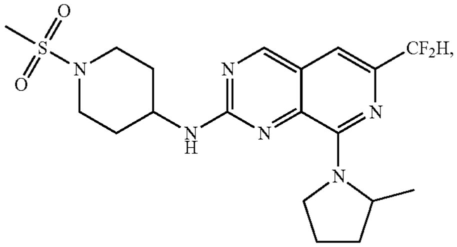
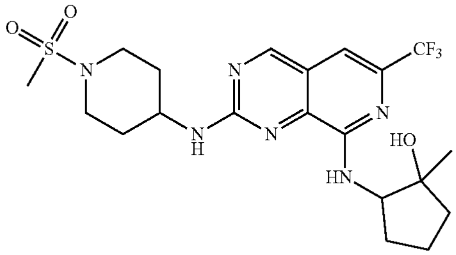
,
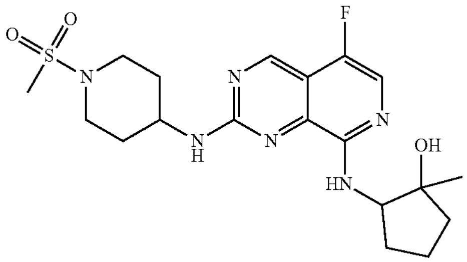
,
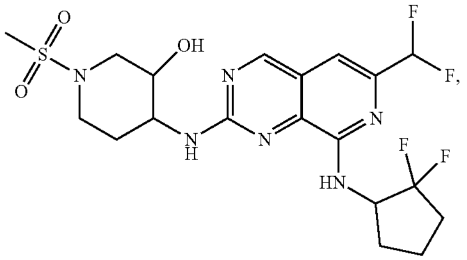
-continued
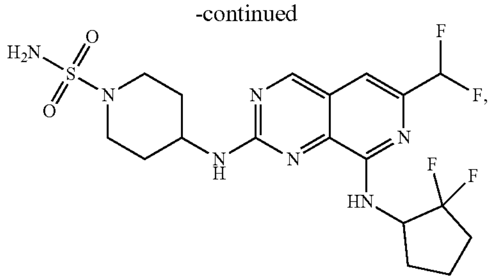
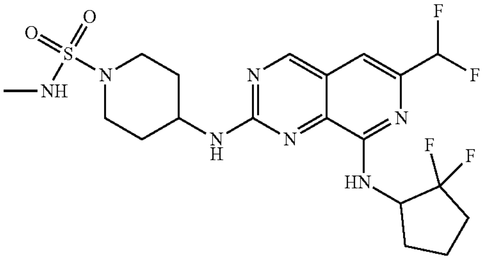
and
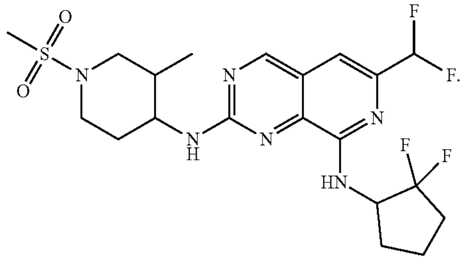
18. The compound or the pharmaceutically acceptable salt thereof as defined in claim 17, wherein, the compound is selected from
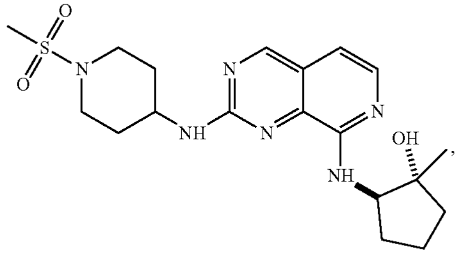
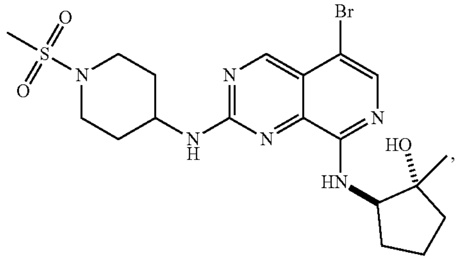
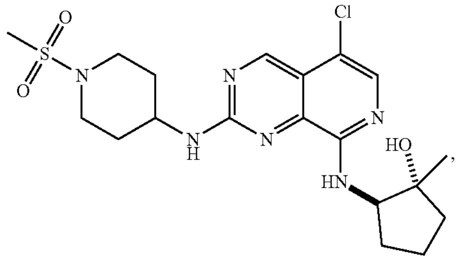

-continued
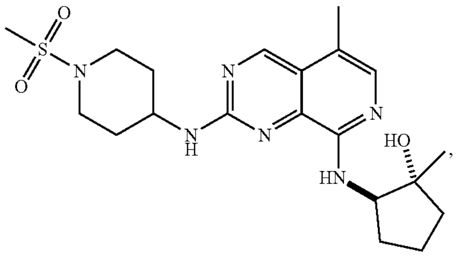
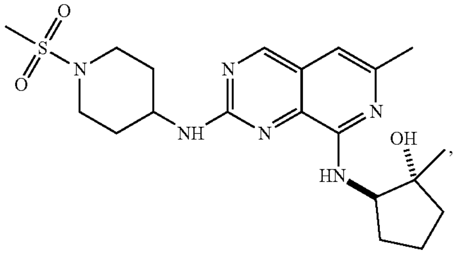
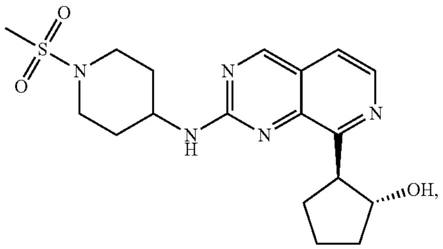
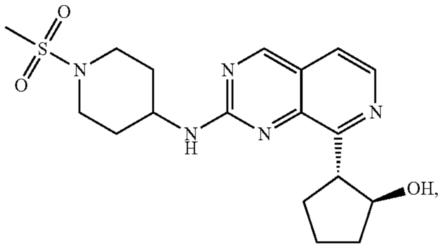
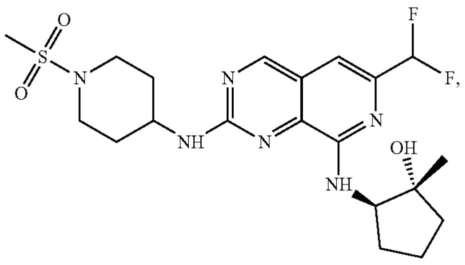
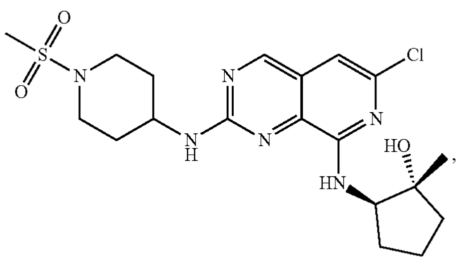
-continued
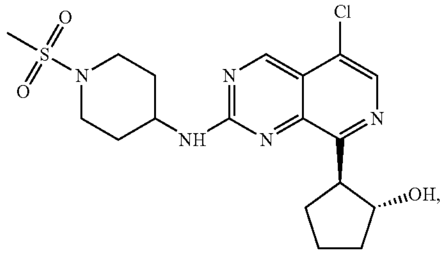
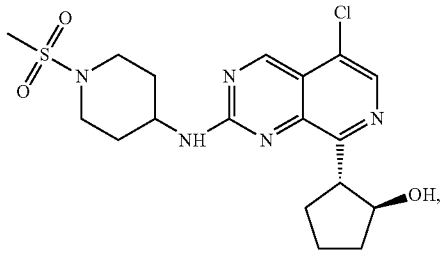
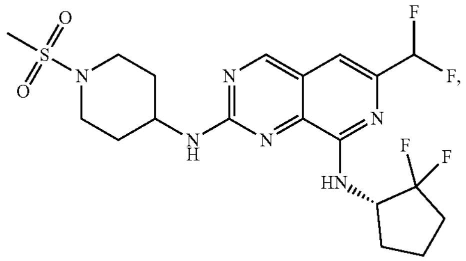
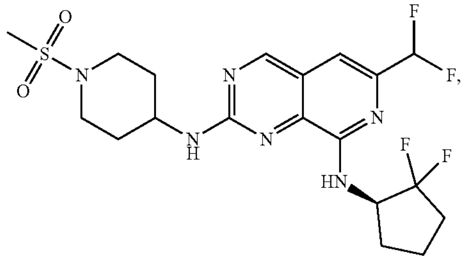
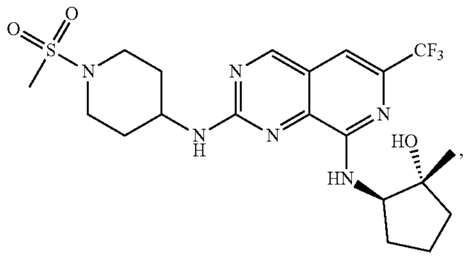
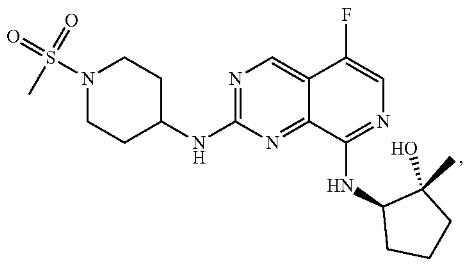

-continued
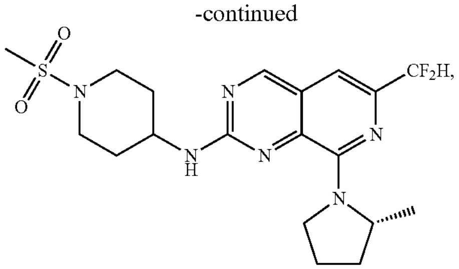
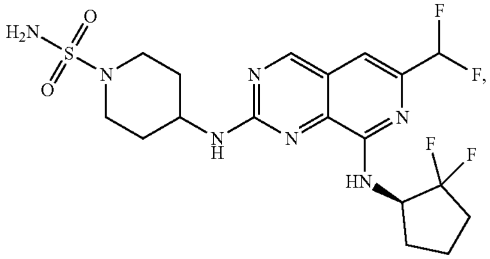
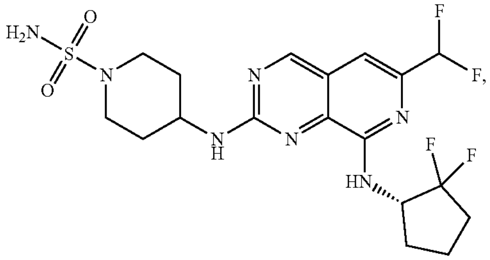
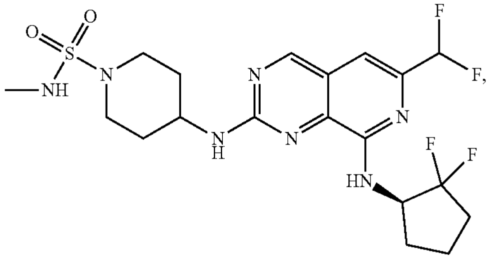
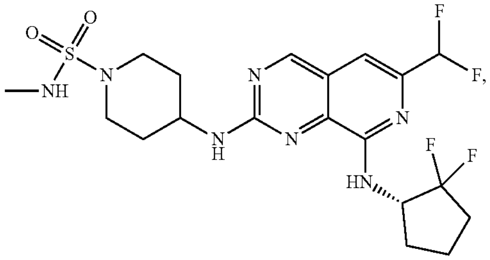
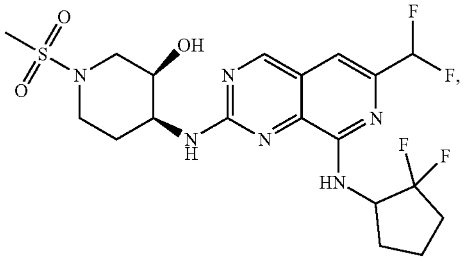
-continued
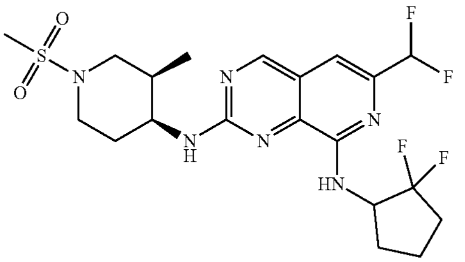
and
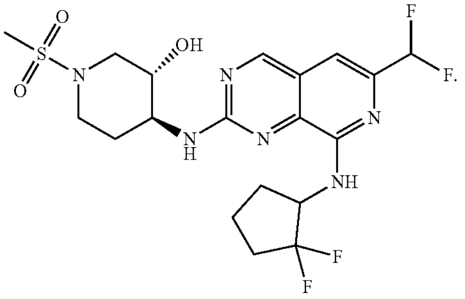
19. The compound or the pharmaceutically acceptable salt thereof as defined in claim 17, wherein, the compound is selected from)
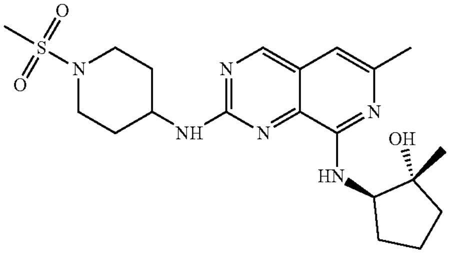
,
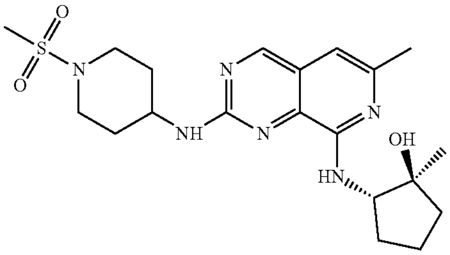
,
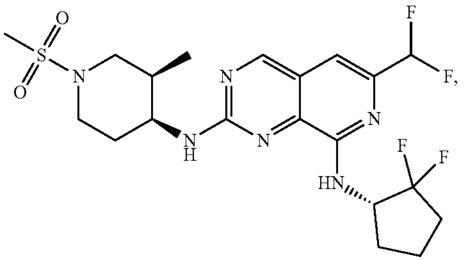

-continued
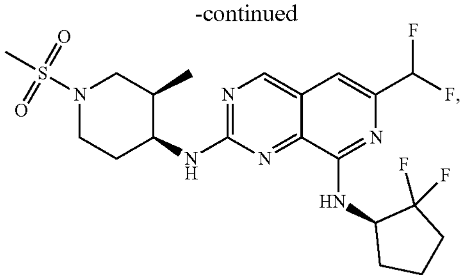
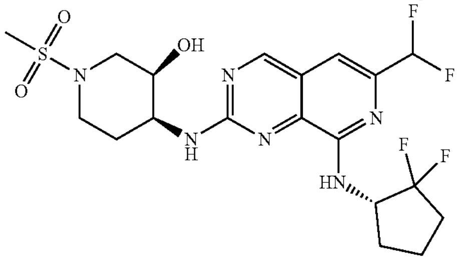
and
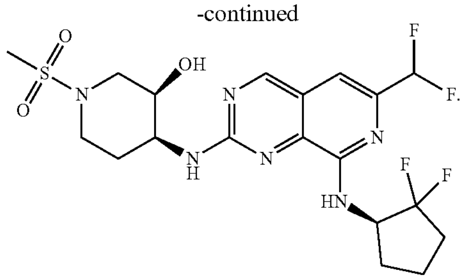
20. A method for treating breast cancer in a subject in need thereof, comprising: administering a therapeutically effective amount of the compound as defined in claim 1 to the subject.
* * * * *